(12) United States Patent
In et al.

(10) Patent No.: US 8,772,632 B2
(45) Date of Patent: *Jul. 8, 2014

(54) COMPOUND FOR ORGANIC PHOTOELECTRIC DEVICE, ORGANIC PHOTOELECTRIC DEVICE INCLUDING THE SAME, AND DISPLAY DEVICE INCLUDING THE SAME

(71) Applicants: Kyu-Yeol In, Uiwang-si (KR); Myeong-Soon Kang, Uiwang-si (KR); Ho-Kuk Jung, Uiwang-si (KR); Nam-Soo Kim, Uiwang-si (KR); Eui-Su Kang, Uiwang-si (KR); Mi-Young Chae, Uiwang-si (KR); Jin-Seong Park, Uiwang-si (KR)

(72) Inventors: Kyu-Yeol In, Uiwang-si (KR); Myeong-Soon Kang, Uiwang-si (KR); Ho-Kuk Jung, Uiwang-si (KR); Nam-Soo Kim, Uiwang-si (KR); Eui-Su Kang, Uiwang-si (KR); Mi-Young Chae, Uiwang-si (KR); Jin-Seong Park, Uiwang-si (KR)

(73) Assignee: Cheil Industries, Inc., Gumi-si, Kyeongsangbuk-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/915,802

(22) Filed: Jun. 12, 2013

(65) Prior Publication Data

US 2013/0274471 A1 Oct. 17, 2013

Related U.S. Application Data

(60) Division of application No. 13/171,986, filed on Jun. 29, 2011, and a continuation of application No. PCT/KR2009/007521, filed on Dec. 16, 2009.

(30) Foreign Application Priority Data

Dec. 30, 2008 (KR) .................. 10-2008-0137222

(51) Int. Cl.
*H01L 31/00* (2006.01)
(52) U.S. Cl.
USPC ..... 136/256; 546/256; 546/270.1; 546/271.7; 548/145

(58) Field of Classification Search
USPC .............. 13/256; 546/256, 270.1, 271.7; 548/145; 136/256
See application file for complete search history.

(56) References Cited

U.S. PATENT DOCUMENTS 5,536,588 A 7/1996 Naito
5,645,948 A 7/1997 Shi et al.
(Continued)

FOREIGN PATENT DOCUMENTS

CN 1366792 A 8/2002
EP 0 825 804 B1 1/2002
(Continued)

OTHER PUBLICATIONS

Baldo, et al., "Very high-efficiency green organic light-emitting devices based on electrophosphorescence", Appl. Phys. Lett., 75(1):4-6 (Jul. 5, 1999).
(Continued)

*Primary Examiner* — Shane Fang
(74) *Attorney, Agent, or Firm* — Lee & Morse, P.C.

(57) ABSTRACT

A compound for an organic photoelectric device, an organic photoelectric device including the same, and a display device including the same the compound being represented by the following Chemical Formula 1:

[Chemical Formula 1]

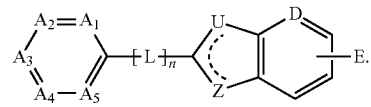

4 Claims, 18 Drawing Sheets

(56) References Cited

U.S. PATENT DOCUMENTS

| | | |
|---|---|---|
| 6,713,192 B2 | 3/2004 | Fukuoka et al. |
| 6,962,755 B2 | 11/2005 | Ise et al. |
| 2002/0037427 A1 | 3/2002 | Taguchi |
| 2003/0165715 A1 | 9/2003 | Yoon et al. |
| 2004/0146745 A1 | 7/2004 | Ise et al. |
| 2005/0164032 A1 | 7/2005 | Ise et al. |
| 2005/0260452 A1 | 11/2005 | Ise et al. |
| 2006/0068223 A1 | 3/2006 | Nariyuki et al. |
| 2006/0110840 A1 | 5/2006 | Araki |
| 2007/0069638 A1 | 3/2007 | Matsuura et al. |
| 2007/0205412 A1 | 9/2007 | Bae et al. |
| 2007/0257600 A1 | 11/2007 | Matsuura et al. |
| 2008/0138656 A1 | 6/2008 | Ohrui et al. |
| 2008/0287583 A1 | 11/2008 | Mataki |
| 2010/0152455 A1 | 6/2010 | Kim et al. |
| 2011/0272676 A1 | 11/2011 | Jung et al. |
| 2013/0256641 A1* | 10/2013 | Jung et al. ................. 257/40 |

FOREIGN PATENT DOCUMENTS

| | | |
|---|---|---|
| EP | 1 734 038 A1 | 12/2006 |
| JP | 07-157473 A | 6/1995 |
| JP | 2001-192653 A | 7/2001 |
| JP | 2002-038141 A | 2/2002 |
| JP | 2002-212181 A | 7/2002 |
| JP | 2003-268362 A | 9/2003 |
| JP | 2005-044790 A | 2/2005 |
| JP | 2006-265515 A | 10/2006 |
| JP | 2008-127315 A | 6/2008 |
| JP | 4879904 B2 | 2/2012 |
| KR | 10-2006-0023046 A | 3/2006 |
| WO | WO 03/060956 A2 | 7/2003 |
| WO | WO 2008/082249 A1 | 7/2008 |
| WO | WO 2009/051454 A2 | 4/2009 |

OTHER PUBLICATIONS

Burroughes, et al., "Light-emitting diodes based on conjugated polymers", Nature, vol. 347, pp. 539-541, (Oct. 11, 1990).
O'Brien, et al., "Improved energy transfer in electrophosphorescent devices", Appl. Phys. Lett., 74(3):442-444 (Jan. 18, 1999).
Tang, et al., "Organic electroluminescent diodes", Appl. Phys. Lett. 51(12):913-915 (Sep. 21, 1987).
Search Report dated Mar. 5, 2013, from Action dated Apr. 2, 2013, in corresponding Chinese Application No. 200980153456.9.
Adachi, Chihaya, et al., Electroluminescence in Organic Films With Three-Layer Structure, Japanese Journal of Applied Physics, vol. 27, No. 2, February, pp. L269-L271 (1988).
Chen; Synthesis and characteristics of cyclometalated iridium(III) complexes containing benzoxazole derivatives and different ancillary ligands; Journal of Organometallic Chemistry; pp. 3117-3130; 693; Elsevier B.V.; USA, (2008).
International Search Report issued in PCT/KR2009/007521 having a mailing date of Jul. 21, 2010.
European Search Report in EP 09836312.0-1218; 2377907, dated Jun. 18, 2012 (In, et al.).

\* cited by examiner

COMPOUND FOR ORGANIC PHOTOELECTRIC DEVICE, ORGANIC PHOTOELECTRIC DEVICE INCLUDING THE SAME, AND DISPLAY DEVICE INCLUDING THE SAME

CROSS-REFERENCE TO RELATED APPLICATIONS

This application is a division based on pending application Ser. No. 13/171,986, filed Jun. 29, 2011, which in turn is a continuation of International Application No. PCT/KR2009/007521, entitled "Novel Compound for Organic Photoelectric Device and Organic Photoelectric Device Including the Same," which was filed on Dec. 16, 2009, the entire content of both of which is incorporated herein by reference in its entirety.

BACKGROUND

1. Field

Embodiments relate to a compound for an organic photoelectric device, an organic photoelectric device including the same, and a display device including the same.

2. Description of the Related Art

An organic photoelectric device transforms electrical energy into light by applying current to an organic light emitting material. It has a structure in which a functional organic material layer is interposed between an anode and a cathode.

The organic light emitting diode has similar electrical characteristics to those of light emitting diodes (LEDs) in which holes are injected from an anode and electrons are injected from a cathode, then the holes and electrons move to opposite electrodes and are recombined to form excitons having high energy. The excitons generate light having a certain wavelength while shifting to a ground state.

Light emission of an anthracene organic material was first discovered in 1960, but was found have a high driving voltage. A polymer light emitting diode may use poly(p-phenylenevinylene) (PPV). Research has been conducted on a low molecular weight light emitting element (SMOLED) and a polymer organic light emitting diode (POLED). The low molecular organic light emitting diode may be manufactured as a thin film in a vacuum deposition method, and may have good efficiency and life-span performance. A polymer organic light emitting diode may be manufactured by an Inkjet or spin coating method and may have an advantage of low initial cost and being large-sized.

SUMMARY

Embodiments are directed to a compound for an organic photoelectric device, an organic photoelectric device including the same, and a display device including the same.

The embodiments may be realized by providing a compound for an organic photoelectric device, the compound being represented by the following Chemical Formula 1:

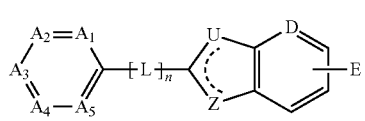

[Chemical Formula 1]

wherein, in Chemical Formula 1, $A_1$ to $A_5$ are each independently selected from the group of $CR_1$ to $CR_5$ and N, provided that three or less of $A_1$ to $A_5$ are N, $R_1$ to $R_5$ are each independently selected from the group of hydrogen, a halogen, a nitrile, a cyano, a nitro, an amide, a carbonyl, an ester, a substituted or unsubstituted alkyl, a substituted or unsubstituted alkoxy, a substituted or unsubstituted alkenyl, a substituted or unsubstituted cycloalkyl, a substituted or unsubstituted aryl, a substituted or unsubstituted arylamine, a substituted or unsubstituted heteroarylamine, a substituted or unsubstituted heterocycle, a substituted or unsubstituted amino, $BR_6R_7$, and $SiR_6R_7R_8$, $R_6$ to $R_8$ are each independently selected from the group of a substituted or unsubstituted alkyl and a substituted or unsubstituted aryl, when only one of $A_1$ to $A_5$ is N, the remaining four of $A_1$ to $A_5$ are respectively selected from the group of $CR_1$ to $CR_5$, provided that at least two of $R_1$ to $R_5$ are not hydrogen, when $A_1$ to $A_5$ are respectively $CR_1$ to $CR_5$, at least two of $R_1$ to $R_5$ are not hydrogen, Z is selected from the group of O, S, Se, and NR", U and D are each independently selected from the group of CR' and N, provided that when Z is O, S, or Se, U is N, R' and R" are each independently selected from the group of hydrogen, a halogen, a nitrile, a cyano, a nitro, an amide, a carbonyl, an ester, a substituted or unsubstituted alkyl, a substituted or unsubstituted alkoxy, a substituted or unsubstituted alkenyl, a substituted or unsubstituted cycloalkyl, a substituted or unsubstituted aryl, a substituted or unsubstituted arylamine, a substituted or unsubstituted heteroarylamine, a substituted or unsubstituted heterocycle, a substituted or unsubstituted amino, $BR_6R_7$, and $SiR_6R_7R_8$, E is selected from the group of hydrogen, a nitrile, a cyano, a nitro, an amide, a carbonyl, a substituted or unsubstituted alkyl, a substituted or unsubstituted fluoroalkyl, a substituted or unsubstituted cycloalkyl, a substituted or unsubstituted aryl, a substituted or unsubstituted heterocycle, and $SO_2R_9$, $R_9$ is selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle, L is selected from the group of a substituted or unsubstituted arylene and a substituted or unsubstituted heteroarylene, and n is 0 or 1.

The compound may be represented by the following Chemical Formula 112:

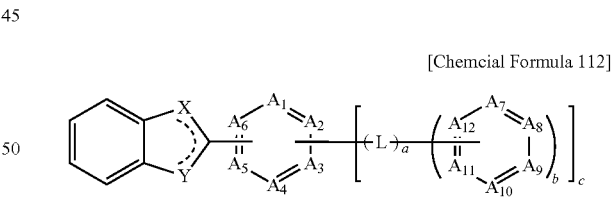

[Chemcial Formula 112]

wherein, in Chemical Formula 112, $A_1$ to $A_{12}$ are each independently selected from the group of $CR_1$ to $CR_{12}$ and N, provided that at least one of $A_7$ to $A_{12}$ is N, and $R_1$ to $R_6$ adjacent to each other optionally form a fused ring, and $R_7$ to $R_{12}$ adjacent to each other optionally form a fused ring, X is selected from the group of O, S, Se, and $NR_{13}$, and Y is $CR_{14}$ or N, provided that when X is selected from the group of O, S, and Se, Y is N, L is a substituted or unsubstituted C6 to C50 arylene, a is 0 or 1, provided that when a is 0, $A_1$ to $A_6$ are each independently $CR_1$ to $CR_6$, and when a is 1, at least one of $A_1$ to $A_6$ is N, b and c are each independently an integer of 1 to 3, and $R_1$ to $R_{14}$ are each independently selected from the group of hydrogen, a halogen, a nitrile, a cyano, a nitro, an amide, a carbonyl, an ester, a substituted or unsubstituted alkyl, a substituted or unsubstituted alkylene, a substituted or unsubstituted alkoxy, a substituted or unsubstituted alkenyl, a substituted or unsubstituted alkenylene, a substituted or unsubstituted alkynyl, a substituted or unsubstituted alkynylene, a substituted or unsubstituted cycloalkyl, a substituted or unsubstituted cycloalkylene, a substituted or unsubstituted aryl, a substituted or unsubstituted arylene, a substituted or unsubstituted arylamine, a substituted or unsubstituted heteroarylamine, a substituted or unsubstituted heterocycle, a substituted or unsubstituted amino, BRR', or SiRR'R", wherein R, R' and R" are the same or different, and each independently a substituted or unsubstituted alkyl, or a substituted or unsubstituted aryl.

In Chemical Formula 112 one of $R_7$ to $R_{12}$ may be substituted with a substituent selected from the group of an amine-substituted alkyl, an amine-substituted cycloalkyl, an amine substituted aryl, and an amine-substituted heterocycle, and one of $R_1$ to $R_6$ may be substituted with a substituent selected from the group of a nitrile, a nitro, an amide, a carbonyl, and a substituted or unsubstituted heterocycle.

The compound may be represented by the following Chemical Formula 113:

[Chemical Formula 113]

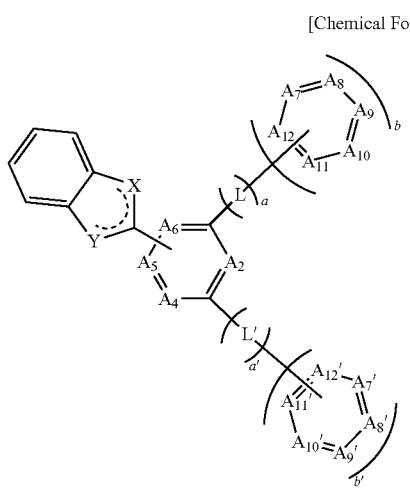

wherein, in Chemical Formula 113, $A_2$, $A_4$ to $A_{12}$ and $A_7'$ to $A_{12}'$ are each independently selected from the group of $CR_2$, $CR_4$ to $CR_{12}$, $CR_7'$ to $CR_{12}'$ and N, provided at least one of $A_7$ to $A_{12}$ is N, and at least one of $A_7'$ to $A_{12}'$ is N, wherein $R_4$ to $R_6$ adjacent to each other optionally form a fused ring, $R_7$ to $R_{12}$ adjacent to each other optionally form a fused ring, and $R_7'$ to $R_{12}'$ adjacent to each other optionally form a fused ring, X is selected from the group of O, S, Se, and $NR_{13}$, and Y is $CR_{14}$ or N, provided that when X is selected from the group of O, S, and Se, Y is N, L and L' are each independently a substituted or unsubstituted C6 to C50 arylene, a and a' are each independently 0 or 1, provided that when a and a' are each independently 0, $A_2$, $A_4$ to $A_6$ are each independently $CR_2$ and $CR_4$ to $CR_6$, and when a and a' are each independently 1, at least one of A, and $A_4$ to $A_6$ is N, b and b' are each independently an integer of 1 to 3, and $R_2$, $R_4$ to $R_{14}$, and $R_7'$ to $R_{12}'$ are each independently hydrogen, a halogen, a nitrile, a cyano, a nitro, an amide, a carbonyl, an ester, a substituted or unsubstituted alkyl, a substituted or unsubstituted alkylene, a substituted or unsubstituted alkoxy, a substituted or unsubstituted alkenyl, a substituted or unsubstituted alkenylene, a substituted or unsubstituted alkynyl, a substituted or unsubstituted alkynylene, a substituted or unsubstituted cycloalkyl, a substituted or unsubstituted cycloalkylene, a substituted or unsubstituted aryl, a substituted or unsubstituted arylene, a substituted or unsubstituted arylamine, a substituted or unsubstituted heteroarylamine, a substituted or unsubstituted heterocycle, a substituted or unsubstituted amino, BRR', or SiRR'R", wherein R, R' and R" are the same or different, and each independently a substituted or unsubstituted alkyl, or a substituted or unsubstituted aryl.

The compound may have an asymmetric structure such that upper and lower substituents are different from each other with respect to an axis including $A_3$.

$A_1$ and $A_5$ may be different from each other, and $A_2$ and $A_4$ may be different from each other.

In Chemical Formula 1, $R_1$, $R_1'$, and $R_1''$ may each independently be a substituted or unsubstituted C6 to C40 aryl.

In Chemical Formula 1, $R_1$, $R_1'$, and $R_1''$ may each independently be an arylamine, the arylamine including one of a diphenyl amine, a dinaphthyl amine, a dibiphenyl amine, a phenyl naphthyl amine, a phenyl diphenyl amine, a ditolyl amine, a phenyl tolyl amine, a carbazolyl, and a triphenyl amine.

In Chemical Formula 1, $R_1$, $R_1'$, and $R_1''$ may each independently be a substituted or unsubstituted heterocycle, the substituted or unsubstituted heterocycle including one of a thiophenyl, a furanyl, a pyrrolyl, an imidazolyl, a thiazolyl, an oxazolyl, an oxadiazolyl, a triazolyl, a pyridinyl, a pyridazinyl, a quinolinyl, an isoquinolinine, an acridyl, an imidazopyridinyl, and an imidazopyrimidinyl.

In Chemical Formula 1, $R_1$, $R_1'$, and $R_1''$ may each independently be a substituted imidazolyl or a substituted triazolyl, the substituent thereof being linked to nitrogen (N) of the imidazolyl or triazolyl, and including one of a substituted or unsubstituted alkyl, a substituted or unsubstituted cycloalkyl, a substituted or unsubstituted aryl, and a substituted or unsubstituted heterocycle.

In Chemical Formula 1, one of $R_1$, $R_1'$, and $R_1''$ may be substituted with a substituent, the substituent including one of an amine-substituted alkyl, an amine-substituted cycloalkyl, an amine-substituted aryl, and an amine-substituted heterocycle, and another of $R_1$, $R_1'$, and $R_1''$ may be substituted with a substituent, the substituent including one of a nitrile, a nitrile, a nitro, an amide, a carbonyl, and a heterocycle.

The embodiments may also be realized by providing an organic photoelectric device including an anode, a cathode, and at least one organic thin layer between the anode and cathode, wherein the at least one organic thin layer includes the compound according to an embodiment.

The compound may be a host material or a charge transport material.

The at least one organic thin layer may include one of an emission layer, an electron transport layer (ETL), an electron injection layer (EIL), a hole transport layer (HTL), a hole injection layer (HIL), and a hole blocking layer.

The at least one organic thin layer may further include a reducing dopant.

The reducing dopant may include one of an alkaline metal, an alkaline earth metal, a rare earth element metal, an oxide of an alkaline metal, a halide of an alkaline metal, an organic complex of an alkaline metal, an oxide of an alkaline earth metal, a halide of an alkaline earth metal, an organic complex of an alkaline earth metal, an oxide of an alkaline earth metal, a halide of an alkaline earth metal, an organic complex of an alkaline earth metal, an oxide of a rare earth element metal, a halide of a rare earth element metal, and an organic complex of a rare earth element metal.

The embodiments may also be realized by providing a display device including an organic photoelectric device according to an embodiment.

BRIEF DESCRIPTION OF THE DRAWINGS

The embodiments will become more apparent to those of ordinary skill in the art by describing in detail exemplary embodiments with reference to the attached drawings, in which.

DETAILED DESCRIPTION

Figure 1:
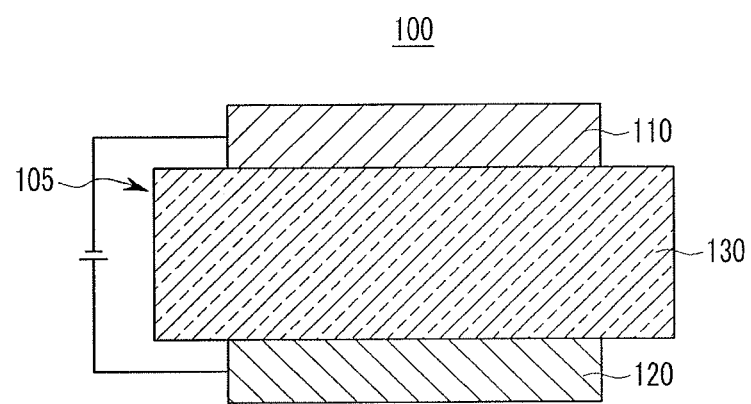
FIGS. 1 to 5 illustrate cross-sectional views of organic photoelectric devices including organic compounds according to various embodiments.

This application claims the benefits of priority of Korean Patent Application No. 10-2008-0137222, filed on Dec. 30, 2008, in the Korean Intellectual Property Office, which is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, when specific definition is not provided, the term "alkyl" may refer to a C1 to C30 alkyl, and preferably a C1 to C15 alkyl; the term "alkoxy" may refer to a C1 to 30 alkoxy, and preferably a C1 to C15 alkoxy; the term "alkenyl" may refer to a C2 to C30 alkenyl, and preferably a C2 to C15 alkenyl; the term "cycloalkyl" may refer to a C3 to C30 cycloalkyl, and preferably a C3 to C15 cycloalkyl; the term "aryl" may refer to a C6 to C50 aryl, and preferably a C6 to C25 aryl; the term "arylamine" may refer to a C7 to C50 arylamine, and preferably a C7 to C25 arylamine; the term "heteroarylamine" may refer to a C7 to C50 heteroarylamine, and preferably a C7 to C25 hetero arylamine; the term "heterocycle" may refer to a C5 to C50 heterocycle, and preferably a C5 to C25 heterocycle; and the term "fluoroalkyl" may refer to a C1 to C10 fluoroalkyl.

As used herein, when a definition is not otherwise provided, the term "ester" may refer to —COOR; and the term "carbonyl" may refer to —COR'. Herein R and R' may each independently be hydrogen, a C1 to C10 alkyl, a C6 to C20 aryl, a C3 to C20 cycloalkyl, a C2 to C10 alkenyl, a C2 to C10 alkynyl, or a combination thereof.

As used herein, when specific definition is not otherwise provided, the term "substituted" may refer to one substituted with at least a substituent selected from the group of a halogen, a nitrile, a cyano, a nitro, an amide, a carbonyl, an acetylene, a C1 to C10 alkyl, a C2 to C10 alkenyl, a C1 to C10alkoxy, a C6 to C20arylamine, a C6 to C20aryl, a C6 to C20arylalkyl, a C6 to C20arylalkenyl, a C2 to C20heterocycle, a C1 to C20amine, a C3 to C20 cycloalkyl, $BR_6R_7$, and $SiR_6R_7R_8$, where $R_6$ to $R_8$ are each independently selected from the group of a C1 to C30 alkyl and a C6 to C50 aryl.

As used herein, when a definition is not otherwise provided, the prefix "hetero" may refer to one including 1 to 3, including N, O, S, or P, in one ring.

As used herein, when specific definition is not provided, the term "heterocycle" may refer to one selected from the group of a C5 to C50 heteroaryl, a C5 to C50 heterocycloalkyl, a C5 to C50 heterocycloalkenyl, a C5 to C50 heterocycloalkynyl, and fused rings thereof. The heterocycle preferably includes 1 to 20 heteroatoms, and more preferably 1 to 15 heteroatoms.

An embodiment provides a compound for an organic photoelectric device, the compound being represented by the following Formula 1:

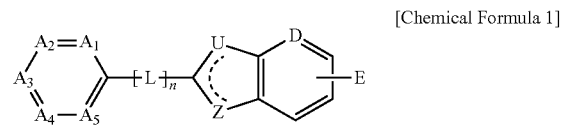

[Chemical Formula 1]

In Chemical Formula 1, $A_1$ to $A_5$ may each independently be selected from the group of $CR_1$ to $CR_5$ and N, provided that three or less of $A_1$ to $A_5$ are N. $R_1$ to $R_5$, R', and R" (R' and R" being described in greater detail below) may each independently be selected from the group of hydrogen, a halogen, a nitrile, a cyano, a nitro, an amide, a carbonyl, an ester, a substituted or unsubstituted alkyl, a substituted or unsubstituted alkoxy, a substituted or unsubstituted alkenyl, a substituted or unsubstituted cycloalkyl, a substituted or unsubstituted aryl, a substituted or unsubstituted arylamine, a substituted or unsubstituted heteroarylamine, a substituted or unsubstituted heterocycle, a substituted or unsubstituted amino, $BR_6R_7$, and $SiR_6R_7R_8$. $R_6$ to $R_8$ may each independently be selected from the group of a substituted or unsubstituted alkyl and a substituted or unsubstituted aryl.

When only one of $A_1$ to $A_5$ is N, the remaining four of $A_1$ to $A_5$ may be respectively selected from the group of $CR_1$ to $CR_5$, provided that at least two of $R_1$ to $R_5$ are not hydrogen, and when $A_1$ to $A_5$ are respectively $CR_1$ to $CR_5$, at least two of $R_1$ to $R_5$ are not hydrogen.

Z may be selected from the group of O, S, Se, and NR".

U and D may each independently be selected from the group of CR' and N, provided that when Z is O, S, or Se, U is N.

E may be selected from the group of hydrogen, a nitrile, a cyano, a nitro, an amide, a carbonyl, a substituted or unsubstituted alkyl, a substituted or unsubstituted fluoroalkyl, a substituted or unsubstituted cycloalkyl, a substituted or unsubstituted aryl, a substituted or unsubstituted heterocycle, and $SO_2R_9$, and $R_9$ may be selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle.

L may be selected from the group of a substituted or unsubstituted arylene and a substituted or unsubstituted heteroarylene, and n may be 0 or 1.

The compound for an organic photoelectric device of the above Chemical Formula 1 may include a part including $A_1$ to $A_5$, a linking group of L including an arylene group or a heteroarylene group, and a functional substituent including a five-member ring.

As noted above, $A_1$ to $A_5$ may each independently be $CR_1$ to $CR_5$ or N, provided that three or fewer of $A_1$ to $A_5$ are N. When any one among $A_1$ to $A_5$ is N, the LUMO (lowest unoccupied molecular orbital) energy level may be lowered and electron affinity of a molecule may be increased. Accordingly, injection and transport characteristics of electrons may be improved. Thus, voltage required for driving an organic light emitting diode may be reduced and electrical power efficiency may be improved. However, when more than four among $A_1$ to $A_5$ are N, too low a LUMO energy level may occur such that it may be difficult to inject electrons.

For example, when any one among $A_1$ to $A_5$ is N, four among $A_1$ to $A_5$ may respectively be selected from the group of $CR_1$ to $CR_5$. Here, at least two of the $R_1$ to $R_5$ may not be hydrogen. When at least one of the $R_1$ to $R_5$ is not hydrogen but is a substituent, rigidity of the compound may be increased and crystallization may easily occur. When the $R_1$ to $R_5$ are all hydrogen, thermal stability may be decreased and injection of electrons may be difficult.

When $A_1$ to $A_5$ are all substituted with N, $A_1$ to $A_5$ may be selected from the group of $CR_1$ to $CR_5$. Here, at least two of the $R_1$ to $R_5$ may not be hydrogen. When at least one of the $R_1$ to $R_5$ is not hydrogen but is a substituent, rigidity of the compound may be increased. When the $R_1$ to $R_5$ are all hydrogen, thermal stability may be decreased, and it may also be difficult to inject electrons.

For example, when at least two of the $R_1$ to $R_5$ are not hydrogen (but rather are a substituent), an amorphous characteristic may be increased by introducing a different substituent into a position of the substituent. Accordingly, crystallization (caused by the Joule heat generated from a device during the operation) may be suppressed and life-span characteristic of an organic light emitting diode may be improved.

In an implementation, $A_1$ and $A_5$ may be different from each other, and $A_2$ and $A_4$ may be different from each other. For example, the compound according to an embodiment may have an asymmetric structure where upper and lower substituents are different from each other with respect to an axis including $A_3$. This asymmetric structure may fortify the amorphous characteristic and may suppress crystallization. Thus, life-span characteristics may be improved when an organic photoelectric device is driven. In addition, driving voltage of the organic photoelectric device may be decreased and an organic photoelectric device having excellent effects in terms of efficiency and thermal stability may be provided.

The linking group, L (including an arylene group or a heteroarylene group) may increase intermolecular interaction, and thereby improve thermal stability. In addition, L may adjust the π-conjugation length and also light emitting in a visual region. Accordingly, the compound according to an embodiment may be usefully applied to an emission layer.

In addition, Z (in the functional substituent including a five-member ring) may be selected from the group of O, S, Se, and NR", and U and D are different or the same. U and D may be independently selected from the group of CR' and N. However, when Z is not NR", e.g., when Z is O, S, or Se, then U is N. The functional substituent including a five-member ring may make the structure of the compound generally asymmetric and may thereby provide the compound with thermal stability.

In Chemical Formula 1, $R_1$ to $R_5$, R', and R" may each independently be aryls, and it is preferable that the aryls are substituted or unsubstituted C6 to C40 aryls. When the aryls are monocyclic aryls, e.g., phenyl, biphenyl, terphenyl, styrene, and so on, or polycyclic aryls, e.g., naphthyl, anthracenyl, phenanthrenyl, pyrenyl, peryenyl, and so on, the compound may be useful for a material of an emission layer.

In an implementation, $R_1$ to $R_5$, R', and R" may each independently be an arylamine. The arylamine is preferably selected from the group of diphenyl amine, dinaphthyl amine, dibiphenyl amine, phenyl naphthyl amine, phenyl diphenyl amine, ditolyl amine, phenyl tolyl amine, carbazolyl, and triphenyl amine.

In an implementation, $R_1$ to $R_5$, R', and R" may each independently be a substituted or unsubstituted heterocycle, and the heterocycle may be selected from the group of thiophenyl, furanyl, pyrrolyl, imidazolyl, thiazolyl, oxazolyl, oxadiazolyl, triazolyl, pyridinyl, pyridazinyl, quinolinyl, isoquinolinine, acridyl, imidazopyridinyl, and imidazopyrimidinyl.

When the substituted or unsubstituted heterocycle is an imidazolyl or a triazolyl, the substituent linked to nitrogen (N) of the imidazolyl or triazolyl may be selected from the group of a substituted or unsubstituted alkyl such as a substituted or unsubstituted methyl, a substituted or unsubstituted ethyl, a substituted or unsubstituted propyl, a substituted or unsubstituted isopropyl, a substituted or unsubstituted butyl, a substituted or unsubstituted t-butyl, a substituted or unsubstituted pentyl, a substituted or unsubstituted hexyl, and a substituted or unsubstituted heptyl; a substituted or unsubstituted cycloalkyl such as a substituted or unsubstituted cyclopentyl, a substituted or unsubstituted cyclohexyl, and so on; a substituted or unsubstituted aryl such as a substituted or unsubstituted phenyl, a substituted or unsubstituted biphenyl, a substituted or unsubstituted naphthyl, and so on; and a substituted or unsubstituted heterocycle. The heterocycle is preferably a heteroaryl, e.g., pyridyl, bipyridyl, quinolyl, isoquinolyl, and so on.

In an implementation, $R_1$ to $R_5$, R', and R" may be functional groups having excellent electron injection characteristics or functional groups being capable of improving thermal stability. The functional groups may selectively provide the compounds with hole injection/transport capabilities and electron injection/transport capabilities, and thus may enable efficient hole-electron combination in an emission layer.

For example, when one of $R_1$ to $R_5$, R', and R" includes a substituent selected from the group of an amine-substituted alkyl, an amine-substituted cycloalkyl, an amine-substituted aryl, and an amine-substituted heterocycle, the compound may be useful for a material of a hole injection layer (HIL) and a hole transport layer (HTL).

When one of $R_1$ to $R_5$, R', and R" includes a substituent having excellent electron affinity selected from the group of a nitrile, a nitro, an amide, a carbonyl, and a heterocycle, the compound may be useful for a material of an electron injection layer (EIL) or an electron transport layer (ETL).

In an implementation, when one of $R_1$ to $R_5$, R', and R" includes a substituent selected from the group of an amine-substituted alkyl, an amine-substituted cycloalkyl, an amine-substituted aryl, and an amine-substituted heterocycle, another of $R_1$ to $R_5$, R', and R" may include a substituent having excellent electron affinity selected from the group of a nitrile, a nitro, an amide, a carbonyl, and a heterocycle, the compound has both hole transport and electron transport capabilities. A preferable amine-substituted heterocycle is an amine-substituted heteroaryl, and a preferable heterocycle is a heteroaryl.

In an implementation, when one of E and R" includes a substituent selected from the group of an amine-substituted alkyl, an amine-substituted cycloalkyl, an amine-substituted aryl, and an amine-substituted heterocycle, and the other of E and R" includes a nitrile, a nitro, an amide, a carbonyl, and a heterocycle, amorphous characteristics may be more improved and hole and electron transport characteristics may be finely controlled. A preferable amine-substituted heterocycle is an amine-substituted heteroaryl, and a preferable heterocycle is a heteroaryl.

L is preferably selected from the group of a substituted or unsubstituted C6 to C30 arylene and a substituted or unsubstituted C5 to C30 heteroarylene.

The various substituents of the above-described compound represented by the above Chemical Formula 1 may not change principal properties of the compound for an organic photoelectric device according to an embodiment.

Examples of compounds for an organic photoelectric device according to an embodiment may include compounds represented by the following Chemical Formulae 2 to 111, but are not limited thereto.

2

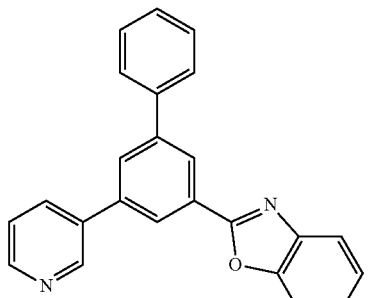

3

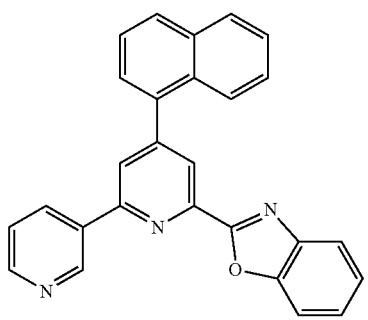

4

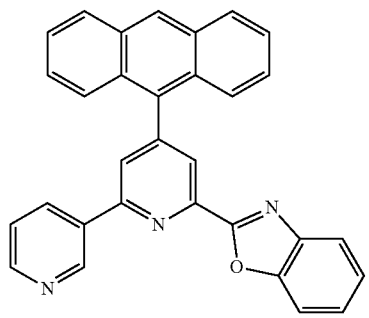

5

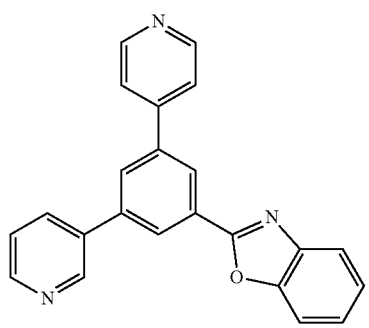

6

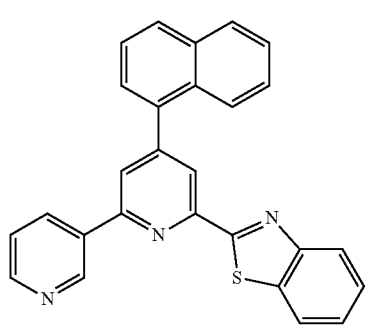

7

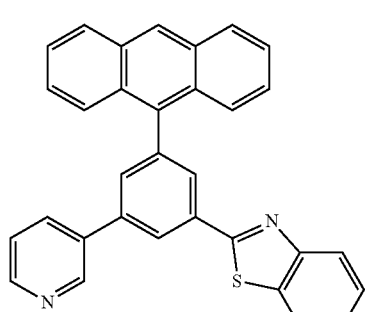

8

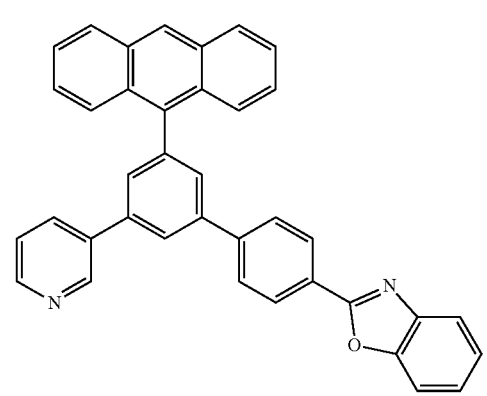

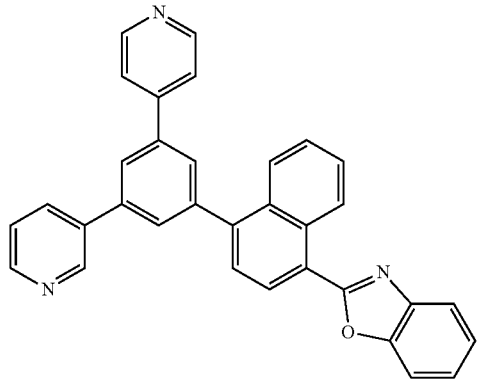
9
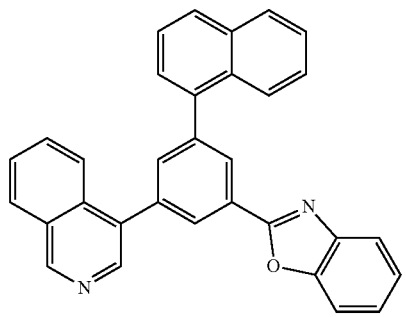
10
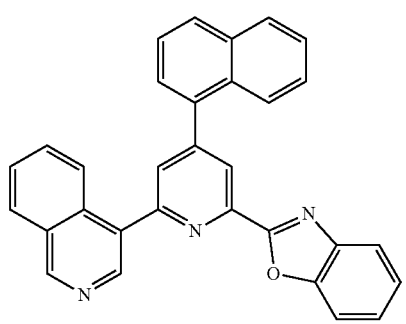
11
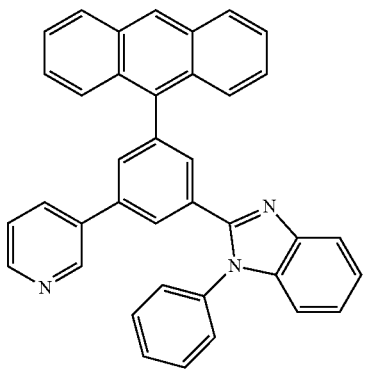
13
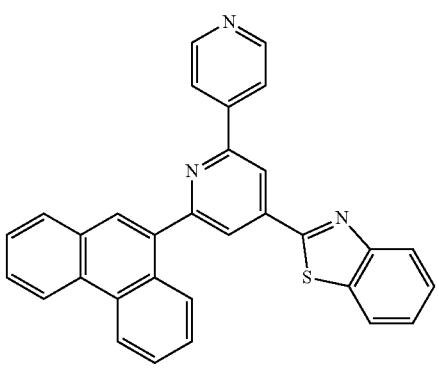
14
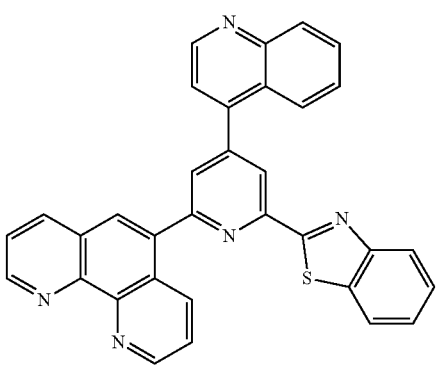
15

17
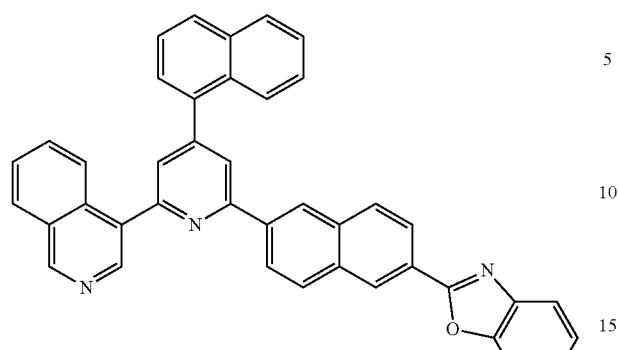
18
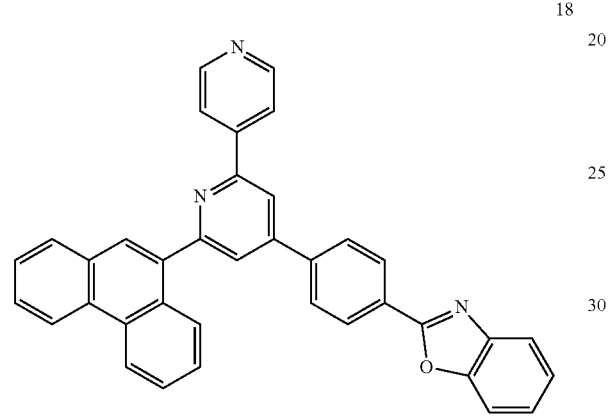
19
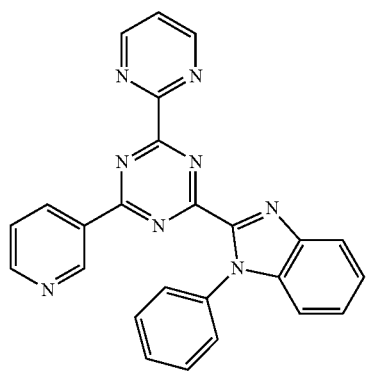
20
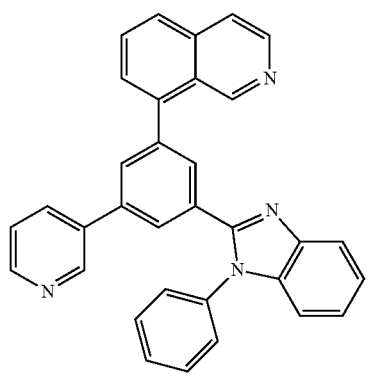
21
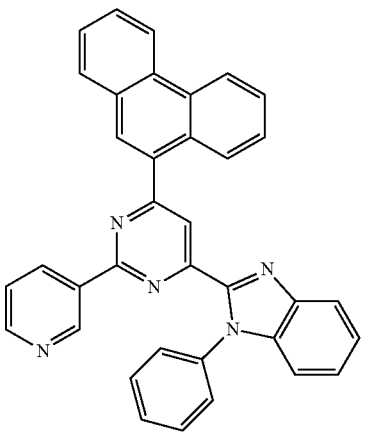
22
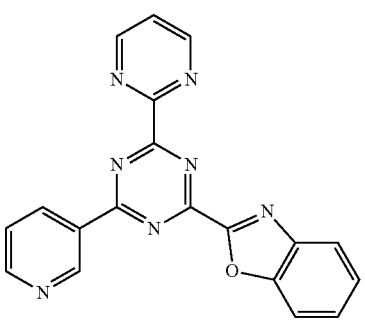
23
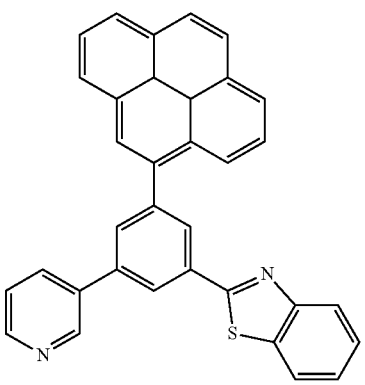
24
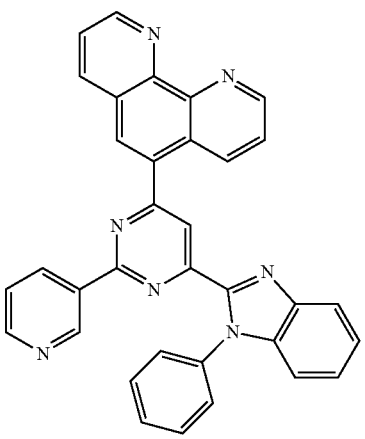

25
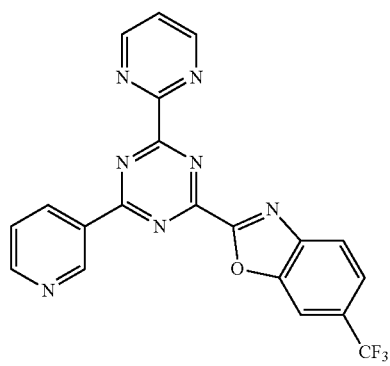
26
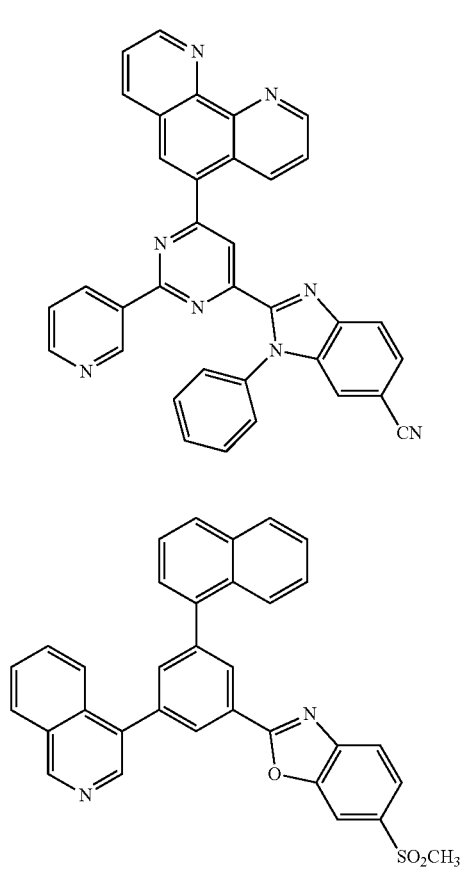
27
28
29
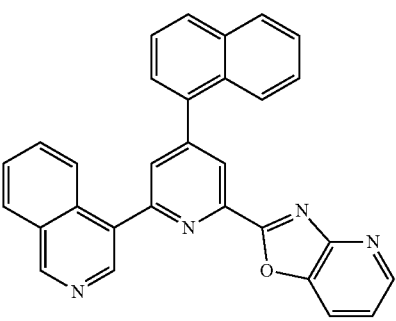
30
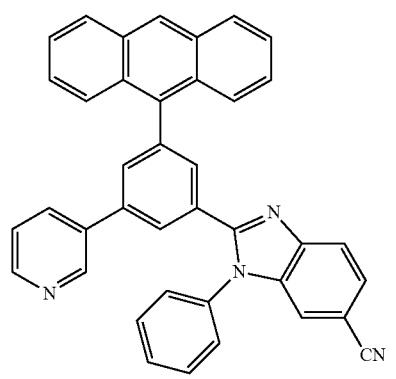
31
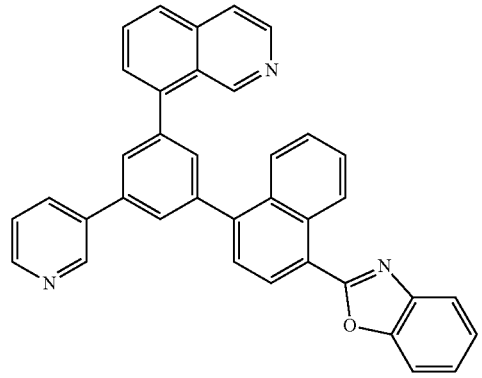
32
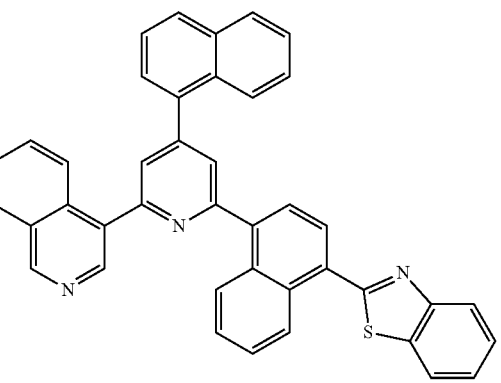

33
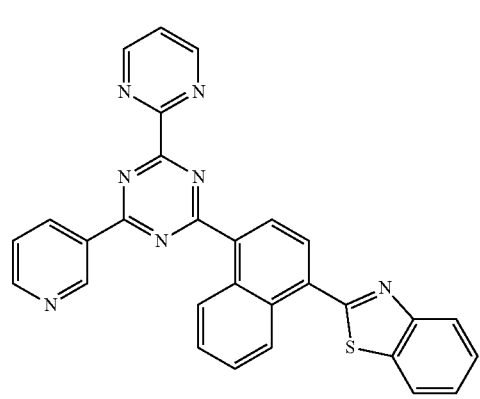
34
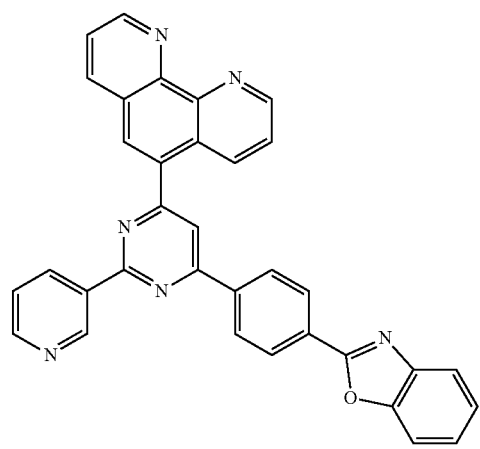
35
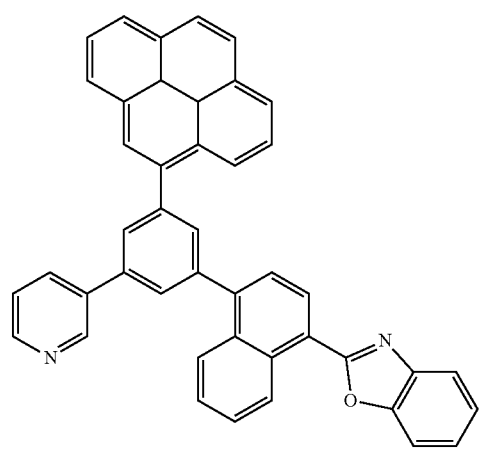
36
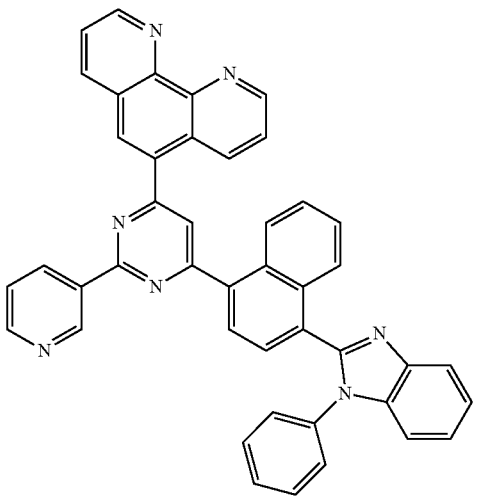
37
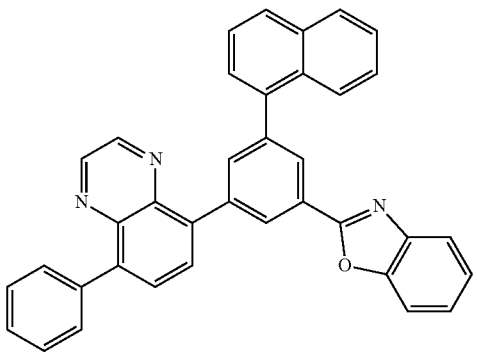
38
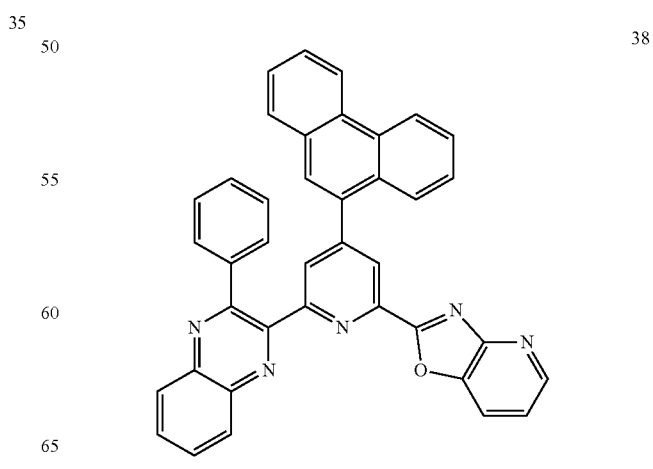

39
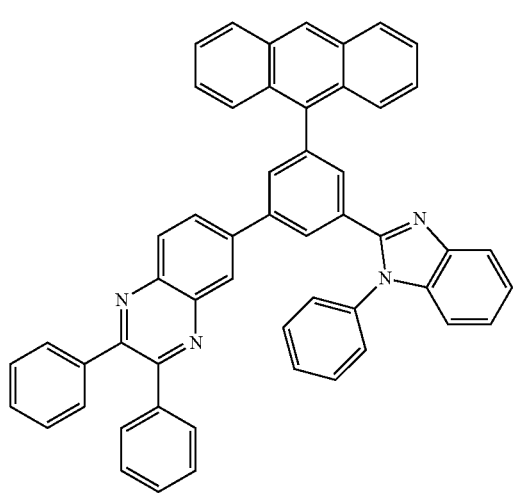
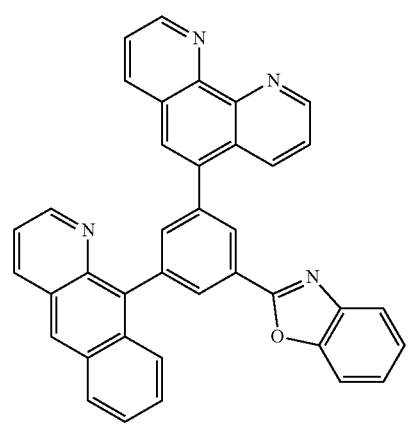
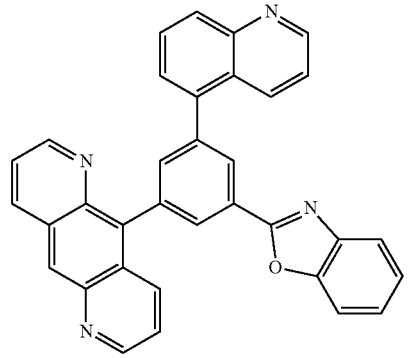
40
42
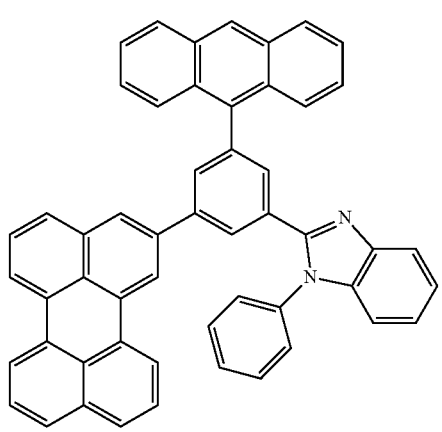
43
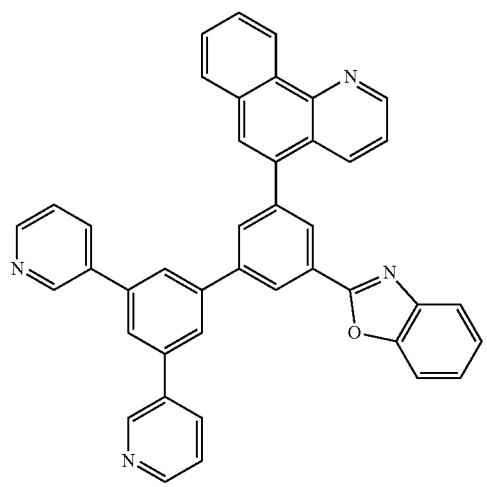
44
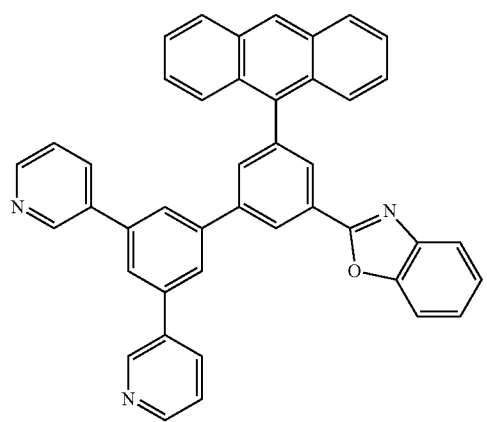

45
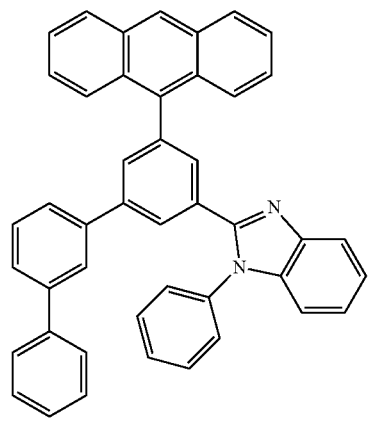
46
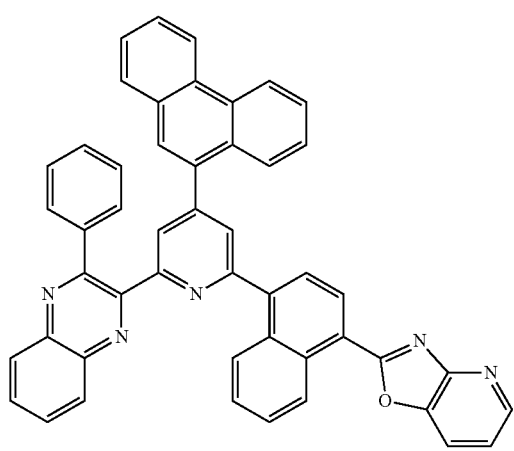
47
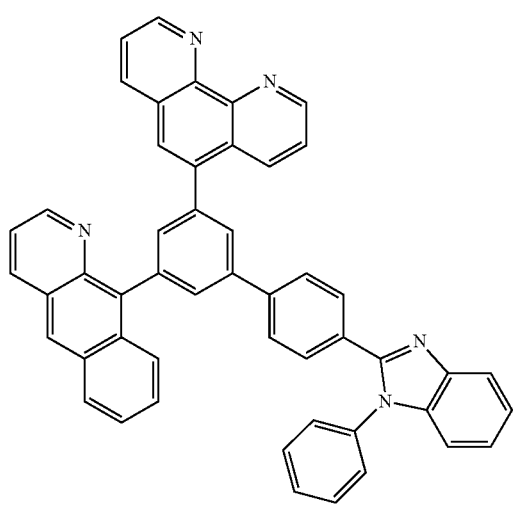
48
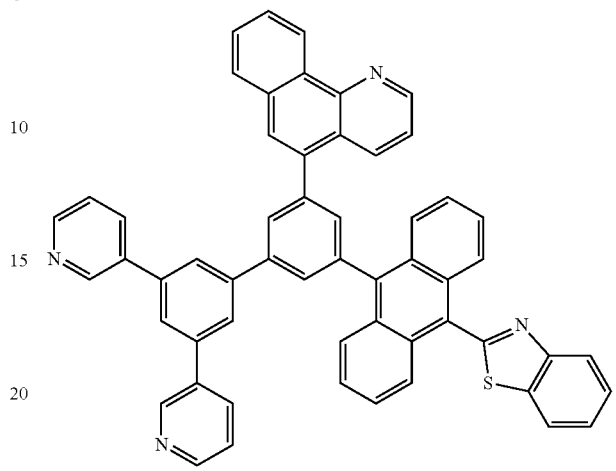
49
50
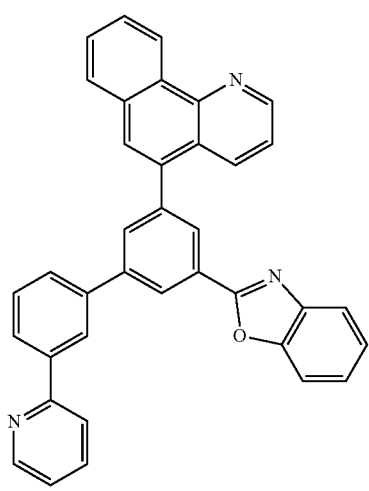

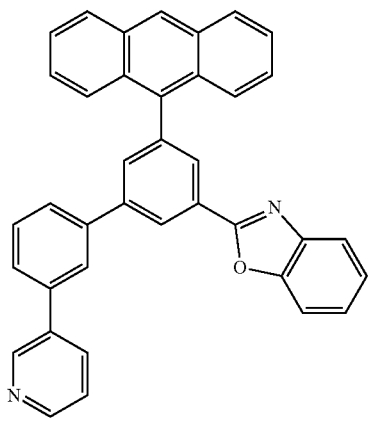
51
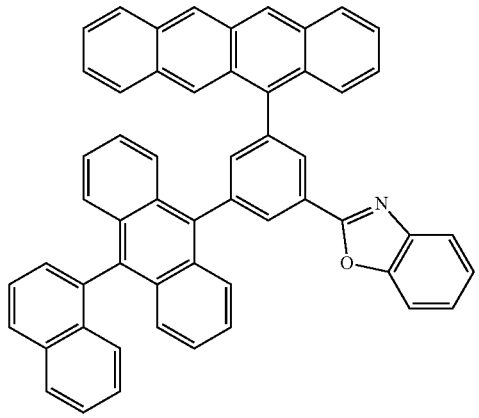
54
52
55
53
56

57
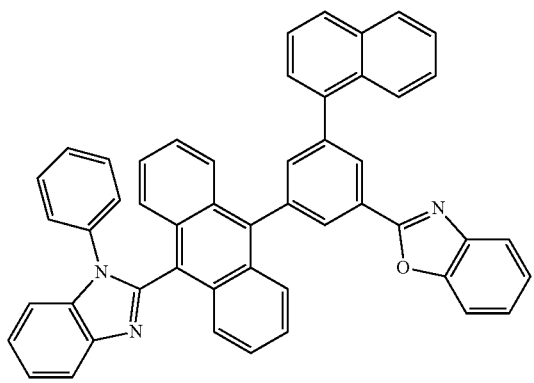
58
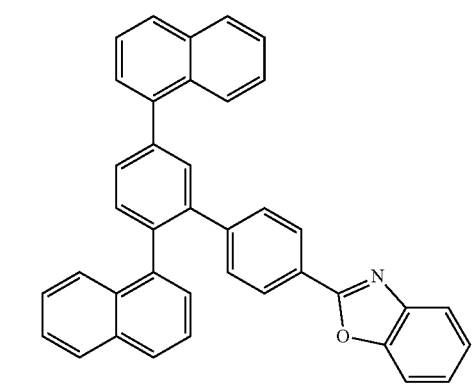
59
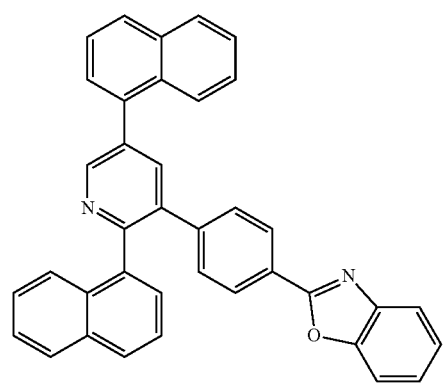
60
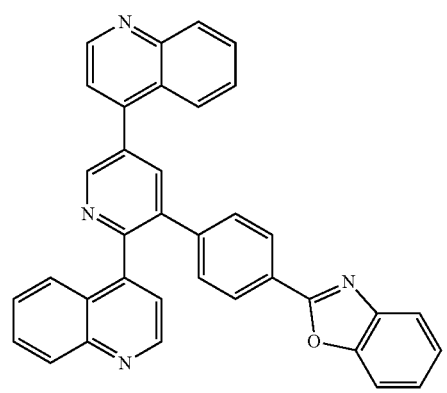
61
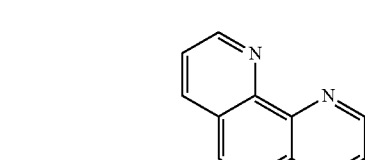
62
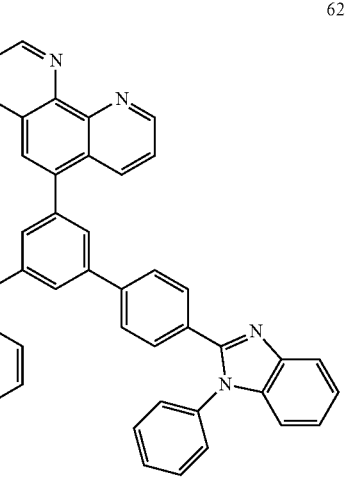
63
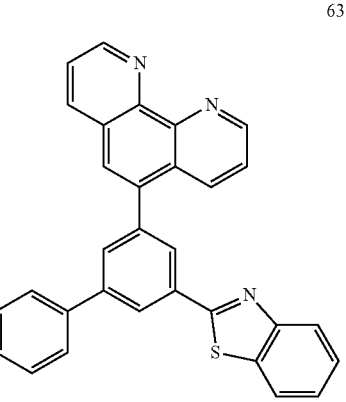

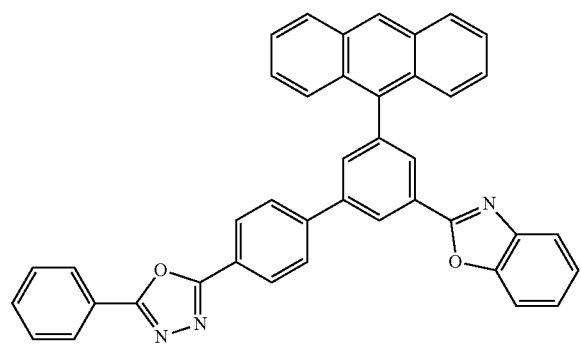
64
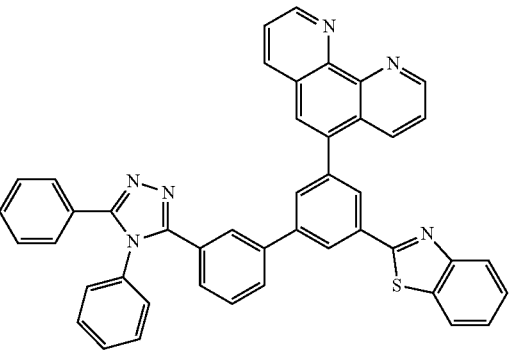
68
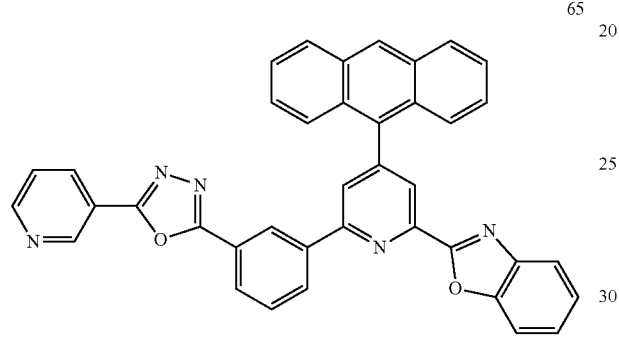
65
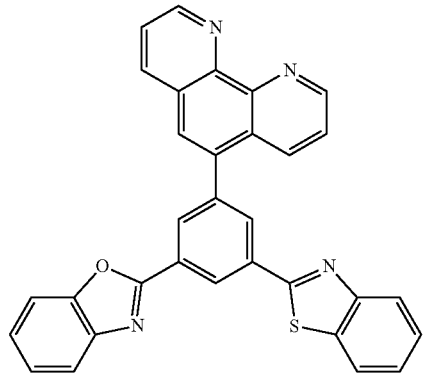
69
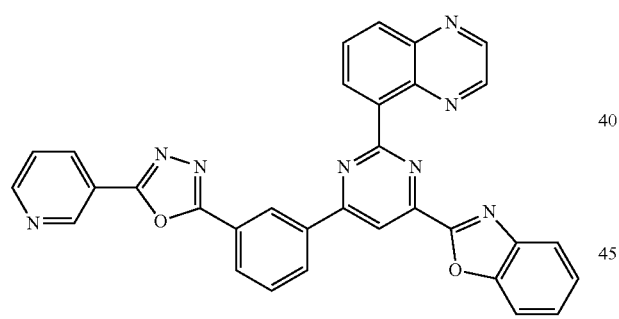
66
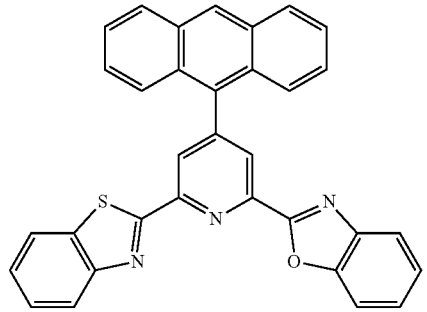
70
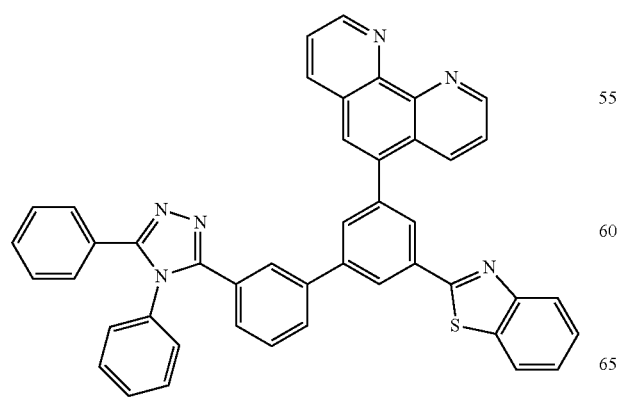
67
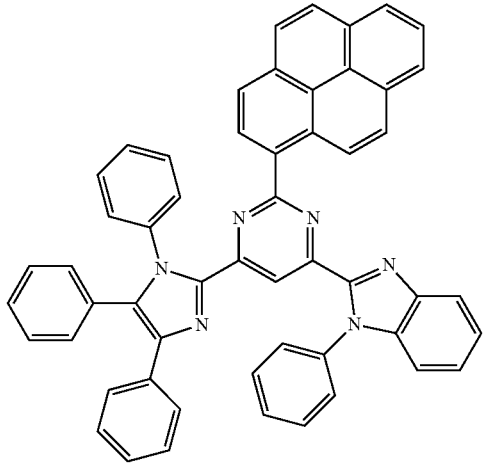
71

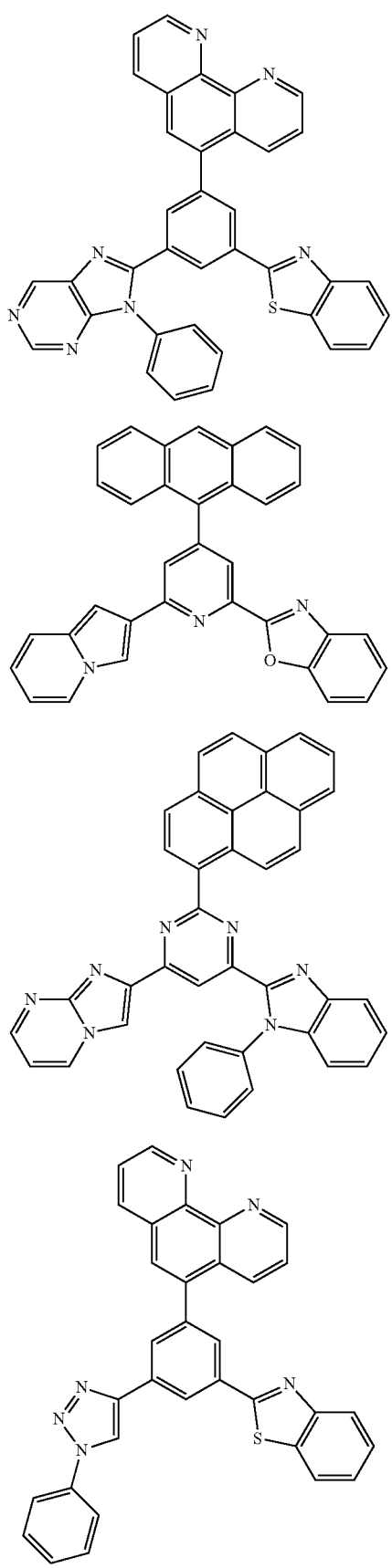
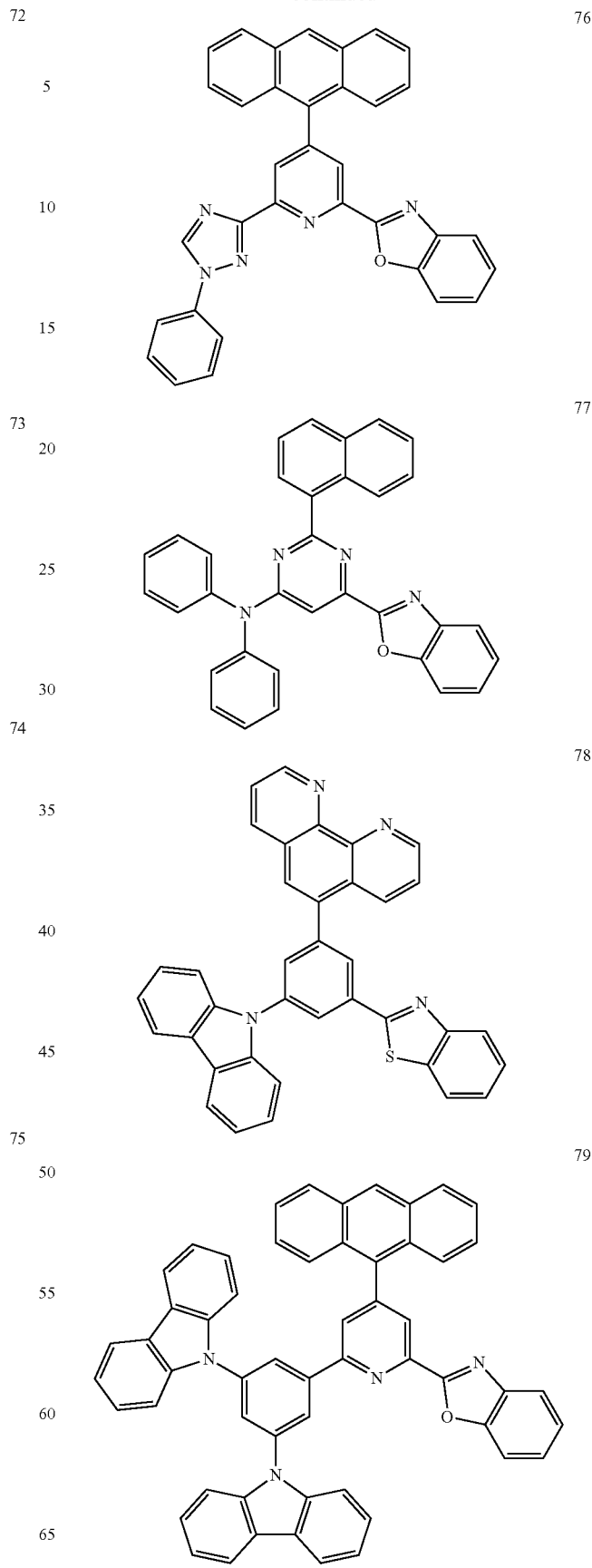

80
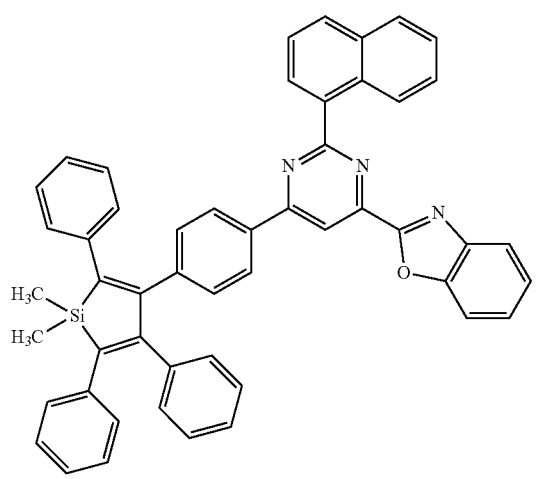
81
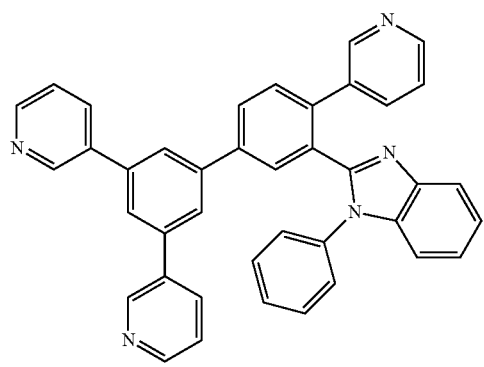
82
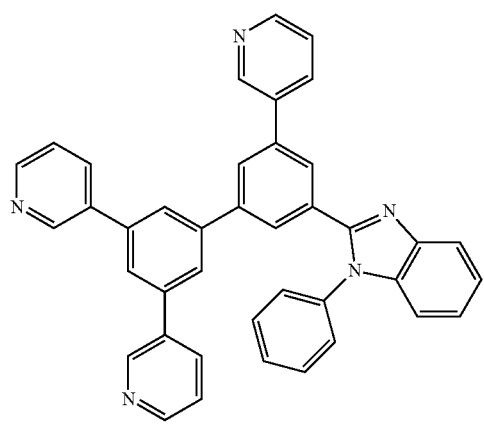
83
84
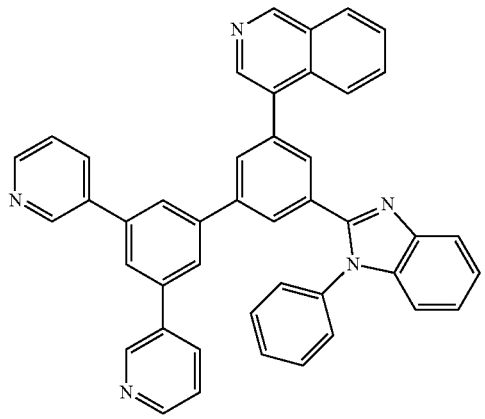
85
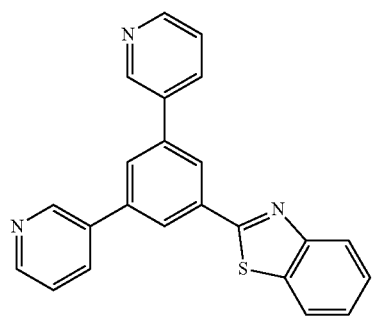
86
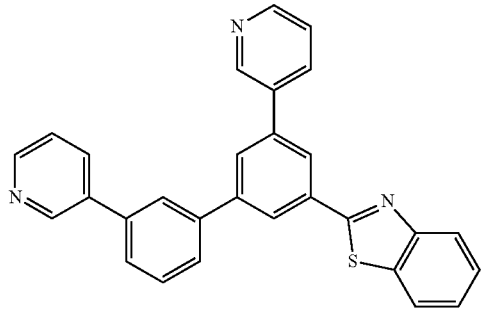
87
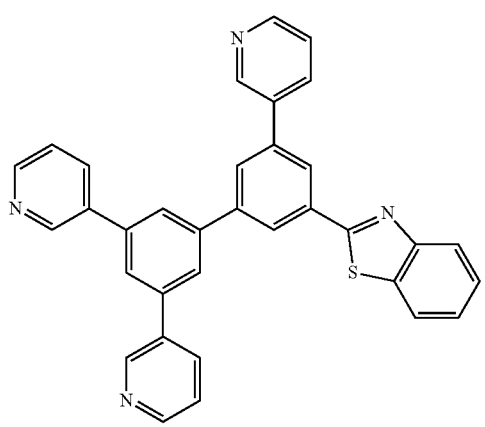

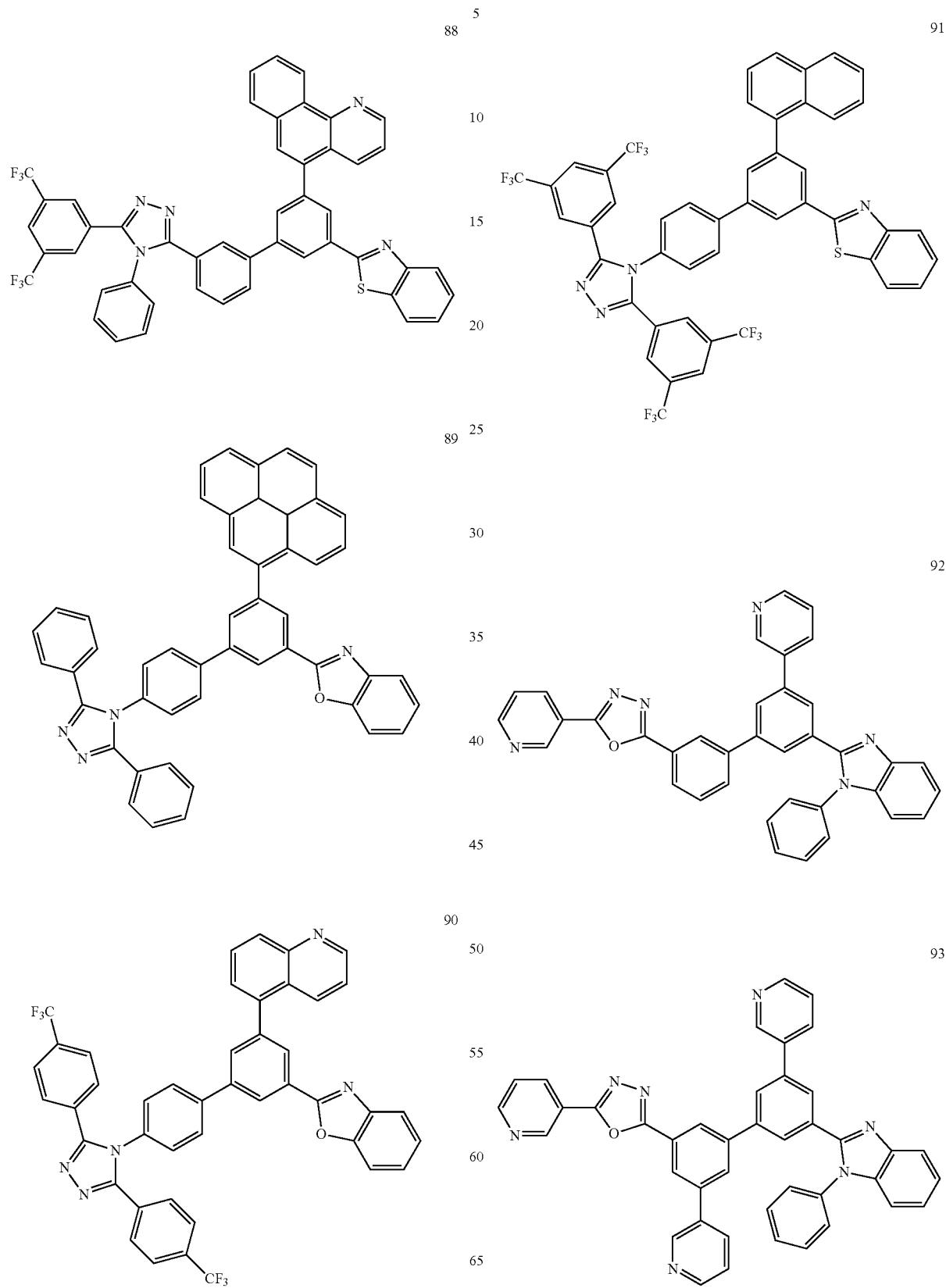

35
-continued
94
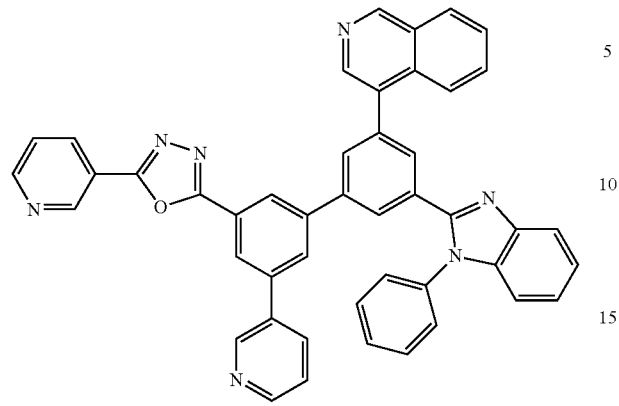
95
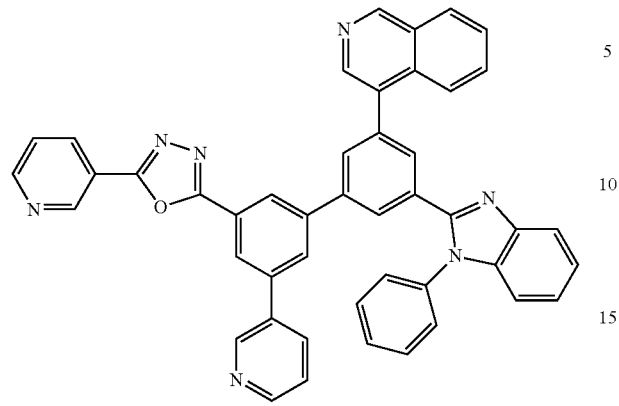
96
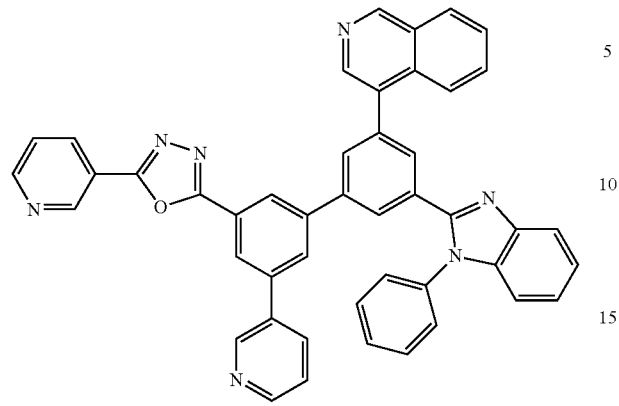
97
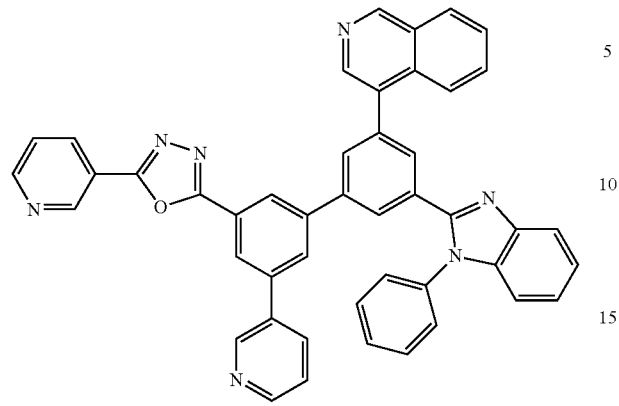
36
-continued
98
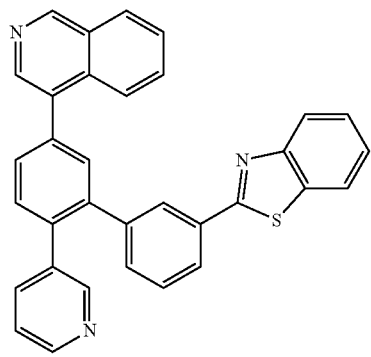
99
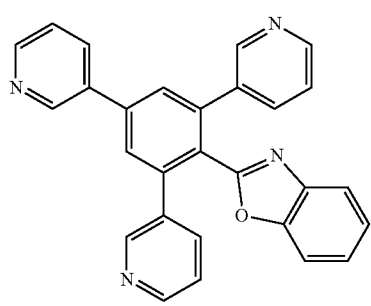
100
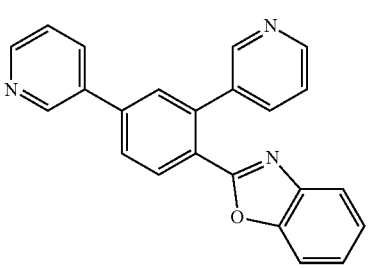
101
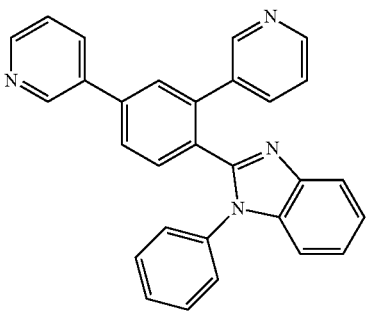
102
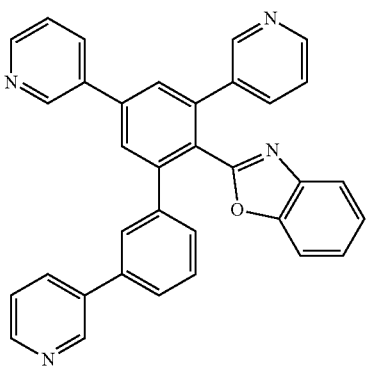

103
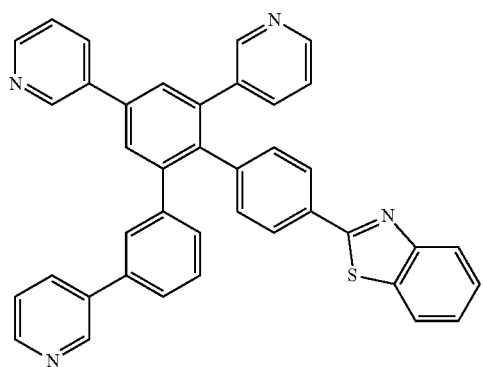
104
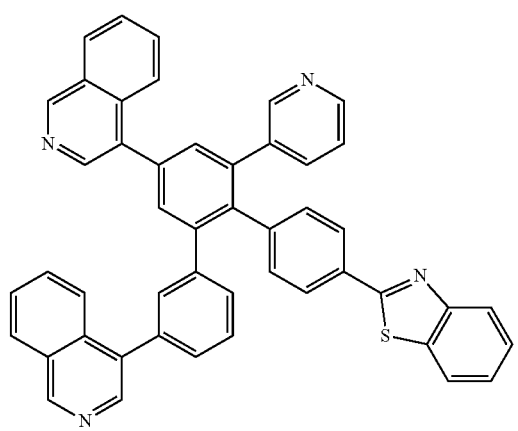
105
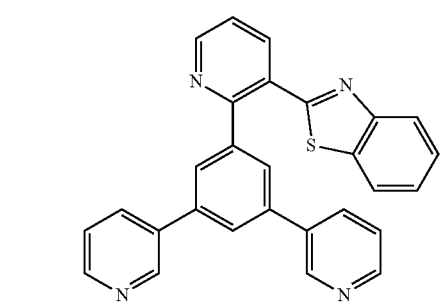
106
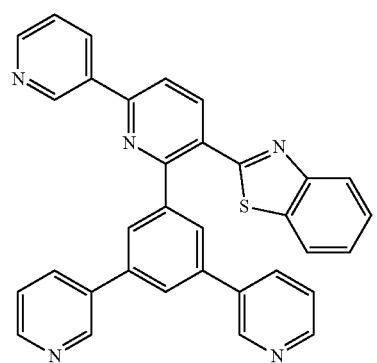
107
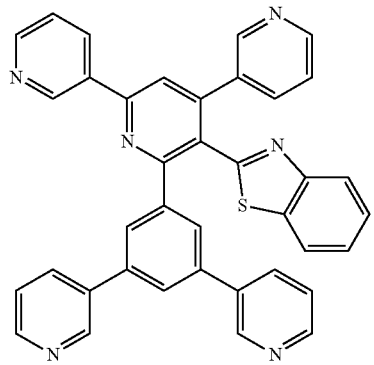
108
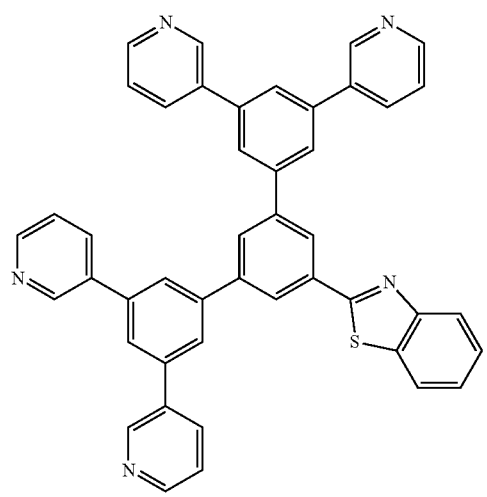
109
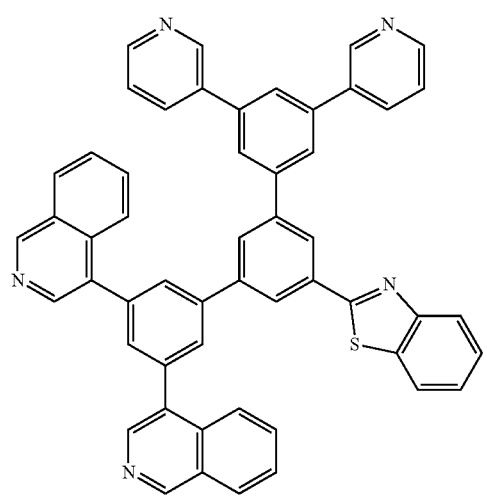

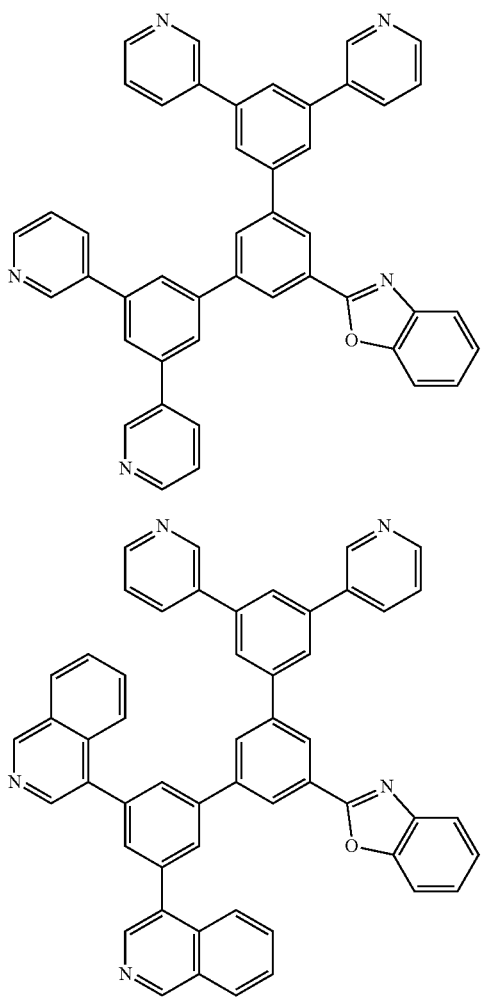

In an implementation, the compound for an organic photoelectric device may be represented by the following Chemical Formula 112 and may include sequentially repeated aryls and heterocycles.

[Chemcial Formula 112]

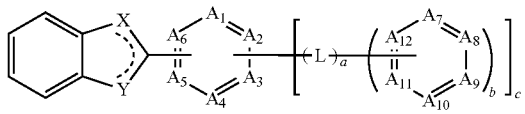

In Chemical Formula 112, $A_1$ to $A_{12}$ may each independently be selected from the group of $CR_1$ to $CR_{12}$ and N, provided that at least one of $A_7$ to $A_{12}$ is N. $R_1$ to $R_6$ adjacent to each other can form a fused ring, and $R_7$ to $R_{12}$ adjacent to each other can form a fused ring.

X may be selected from the group of O, S, Se, and $NR_{13}$. Y may be $CR_{14}$ or N, provided that when X is selected from the group of O, S, and Se, Y is N, L may be a substituted or unsubstituted C6 to C50 arylene, a may be 0 or 1, provided that when a is 0, $A_1$ to $A_6$ are each independently $CR_1$ to $CR_6$, and when a is 1, at least one of $A_1$ to $A_6$ is N, b and c may each independently be an integer of 1 to 3, and $R_1$ to $R_{14}$ may each independently be selected from the group of hydrogen, a halogen, a nitrile, a cyano, a nitro, an amide, a carbonyl, an ester, a substituted or unsubstituted alkyl, a substituted or unsubstituted alkylene, a substituted or unsubstituted alkoxy, a substituted or unsubstituted alkenyl, a substituted or unsubstituted alkenylene, a substituted or unsubstituted alkynyl, a substituted or unsubstituted alkynylene, a substituted or unsubstituted cycloalkyl, a substituted or unsubstituted cycloalkylene, a substituted or unsubstituted aryl, a substituted or unsubstituted arylene, a substituted or unsubstituted arylamine, a substituted or unsubstituted heteroarylamine, a substituted or unsubstituted heterocycle, a substituted or unsubstituted amino, BRR', or SiRR'R", wherein R, R' and R" are each independently a substituted or unsubstituted alkyl or a substituted or unsubstituted aryl.

When an adjacent two of $R_1$ to $R_6$ form a fused ring, or an adjacent two of $R_7$ to $R_{12}$ form a fused ring, a fused ring including $A_1$ to $A_6$ and a fused ring including $A_7$ to $A_{12}$ may be polycyclic aryls, e.g., naphthyl, anthracenyl, phenanthrenyl, pyrenyl, peryenyl, pyrenyl, fluorenyl, and the like. For example, when at least one of $A_7$ to $A_{12}$ is N, one or more carbons of the polycyclic aryls may be substituted with N.

When $R_7$ to $R_{12}$ are each independently substituted or unsubstituted aryl or substituted or unsubstituted arylene, the compound may be usefully applicable to an emission layer.

When X is selected from the group of O, S, and Se, Y may be N, such that at least one of X and Y is N. In this case, the LUMO (lowest unoccupied molecular orbital) energy level may be lowered and electron affinity of a molecule may be increased, thereby improving injection and transport characteristics of electrons. Accordingly, voltage required for driving an organic light emitting diode may be decreased and electrical power efficiency may be improved.

The functional substituents including X and Y may provide the compound with a predetermined rigidity and thus may increase intermolecular interaction. The compound for an organic photoelectric device according to an embodiment may have thermal stability due to a high glass transition temperature, and may thereby improve life-span of an organic light emitting diode.

L may be a substituted or unsubstituted C6 to C50 arylene. For example, aryls of $R_7$ to $R_{12}$ and L is a C6 to C50 aryl, and the aryl may be monocyclic aryls such as phenyl; or polycyclic aryls such as naphthyl, anthracenyl, phenanthrenyl, pyrenyl, peryenyl, and so on. The compound may be useful for a material of an emission layer.

The linking group L may increase intermolecular interaction, and may thereby improve thermal stability. In addition, L may adjust the π-conjugation length and also light emitting in a visual region. Accordingly, a compound for an organic photoelectric device according to an embodiment may be usefully applied to an emission layer.

b and c may be integers of 1 to 3. When b and c are 2 or more, each repeating unit may be different.

For example, when c is 2, two repeating units may be linked to each other at a meta position of the benzene ring including $A_1$ to $A_6$.

In another implementation, the compound for an organic photoelectric device according to an embodiment may include a compound represented by the following Chemical Formula 113:

[Chemical Formula 113]

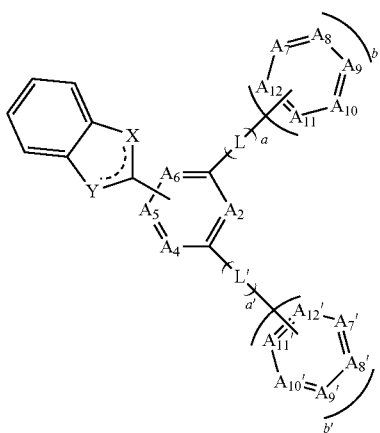

In Chemical Formula 113, $A_2$, $A_4$ to $A_{12}$ and $A_7'$ to $A_{12}'$ may each independently be selected from the group of $CR_2$, $CR_4$ to $CR_{12}$, $CR_7'$ to $CR_{12}'$, and N, provided at least one of $A_7$ to $A_{12}$ is N, and at least one of $A_7'$ to $A_{12}'$ is N. $R_4$ to $R_6$ adjacent to each other can form a fused ring, $R_7$ to $R_{12}$ adjacent to each other can form a fused ring, and $R_7'$ to $R_{12}'$ adjacent to each other can form a fused ring, X may be selected from the group of O, S, Se, and $NR_{13}$. Y may be $CR_{14}$ or N, provided that when X is selected from the group of O, S, and Se, Y is N, L and L' may each independently be a substituted or unsubstituted C6 to C50 arylene, a and a' may each independently be 0 or 1, provided that when a and a' are each independently 0, $A_2$, $A_4$ to $A_6$ are each independently $CR_2$, and $CR_4$ to $CR_6$, and when a and a' are each independently 1, at least one of $A_2$, and $A_4$ to $A_6$ is N, b and b' may each independently be an integer ranging from 1 to 3, and $R_2$, $R_4$ to $R_{14}$, and $R_7'$ to $R_{12}'$ may each independently be hydrogen, a halogen, a nitrile, a cyano, a nitro, an amide, a carbonyl, an ester, a substituted or unsubstituted alkyl, a substituted or unsubstituted alkylene, a substituted or unsubstituted alkoxy, a substituted or unsubstituted alkenyl, a substituted or unsubstituted alkenylene, a substituted or unsubstituted alkynyl, a substituted or unsubstituted alkynylene, a substituted or unsubstituted cycloalkyl, a substituted or unsubstituted cycloalkylene, a substituted or unsubstituted aryl, a substituted or unsubstituted arylene, a substituted or unsubstituted arylamine, a substituted or unsubstituted hetero arylamine, a substituted or unsubstituted heterocycle, a substituted or unsubstituted amino, BRR', or SiRR'R", wherein R, R', and R" may each independently be a substituted or unsubstituted alkyl, or a substituted or unsubstituted aryl.

An adjacent two of $R_4$ to $R_6$ can form a fused ring, an adjacent two of $R_7$ to $R_{12}$ can form a fused ring, and an adjacent two of $R_7'$ to $R_{12}'$ can form a fused ring. The fused ring may be polycyclic aryls such as naphthyl, anthracenyl, phenanthrenyl, pyrenyl, peryenyl, pyrenyl, fluorenyl, and the like. For example, when at least one of $A_7$ to $A_{12}$ is N, and at least one of $A_7'$ to $A_{12}'$ is N, one or more carbons of the polycyclic aryls may be substituted with N.

L and L' may each independently be a substituted or unsubstituted C6 to C50 arylene. For example, the aryl may be a C6 to C50 aryl, and the aryl may be monocyclic aryls such as phenyl; or polycyclic aryls such as naphthyl, anthracenyl, phenanthrenyl, pyrenyl, peryenyl, and so on. The compound may be useful for a material of an emission layer.

b and b' may each independently integers of 1 to 3, and when b and b' are 2 or more, each repeating unit may be different.

When $R_1$ to $R_{14}$ in Chemical Formula 112 and $R_2$, $R_4$ to $R_{14}$, and $R_7'$ to $R_{12}'$ in Chemical Formula 113 are a substituted or unsubstituted aryl, a substituted or unsubstituted arylene, or a substituted or unsubstituted arylamine, the aryl may be a C6 to C50 aryl. For example, when the aryls are monocyclic aryls such as phenyl, biphenyl, terphenyl, styrene, and so on, or polycyclic aryls such as naphthyl, anthracenyl, phenanthrenyl, pyrenyl, peryenyl, and so on, the compound may be useful for a material of an emission layer.

When $R_1$ to $R_{14}$ in Chemical Formula 112 and $R_2$, $R_4$ to $R_{14}$, and $R_7'$ to $R_{12}'$ in Chemical Formula 113 are a substituted or unsubstituted heteroarylamine, or a substituted or unsubstituted heteroaryl, the aryl may be the same as described above. The heteroaryl may refer to an aryl including 1 to 3 heteroatoms of N, O, S, or P, and remaining carbons.

$R_1$ to $R_{14}$ in Chemical Formula 112 and $R_2$, $R_4$ to $R_{14}$, and $R_7'$ to $R_{12}'$ in Chemical Formula 113 may be a substituted or unsubstituted arylamine, and the arylamine may be selected from the group of diphenyl amine, dinaphthyl amine, dibiphenyl amine, phenyl naphthyl amine, phenyl diphenyl amine, ditolyl amine, phenyl tolyl amine, carbazolyl, and triphenyl amine, which provides balance between electron and hole mobility characteristics.

When $R_1$ to $R_{14}$ in Chemical Formula 112 and $R_2$, $R_4$ to $R_{14}$, and $R_7'$ to $R_{12}'$ in Chemical Formula 113 are a substituted or unsubstituted heterocycle, the heterocycle may be selected from the group of thiophenyl, furanyl, pyrrolyl, imidazolyl, thiazolyl, oxazolyl, oxadiazolyl, triazolyl, pyridinyl, pyridazinyl, quinolinyl, isoquinolinine, acridyl, imidazopyridinyl, and imidazopyrimidinyl.

For example, a substituent linked to nitrogen (N) of the imidazolyl or triazolyl may be selected from the group of a substituted or unsubstituted alkyl such as a substituted or unsubstituted methyl, a substituted or unsubstituted ethyl, a substituted or unsubstituted propyl, a substituted or unsubstituted isopropyl, a substituted or unsubstituted butyl, a substituted or unsubstituted t-butyl, a substituted or unsubstituted pentyl, a substituted or unsubstituted hexyl, and a substituted or unsubstituted heptyl; a substituted or unsubstituted cycloalkyl such as a substituted or unsubstituted cyclopentyl, a substituted or unsubstituted cyclohexyl, and so on; a substituted or unsubstituted aryl such as a substituted or unsubstituted phenyl, a substituted or unsubstituted biphenyl, a substituted or unsubstituted naphthyl, and so on; and a substituted or unsubstituted heterocycle. The heterocycle is preferably a heteroaryl such as pyridyl, bipyridyl, quinolyl, isoquinolyl, and so on.

At least one of $R_1$ to $R_{12}$ in Chemical Formula 112 and at least one of $R_2$, $R_4$ to $R_{12}$, and $R_7'$ to $R_{12}'$ in Chemical Formula 113 may be substituted with at least one of substituent selected from an amine-substituted alkyl, an amine-substituted cycloalkyl, an amine-substituted aryl, and an amine-substituted heterocycle, which makes the compound be applicable to a hole injection layer (HIL) or a hole transport layer (HTL).

At least one of $R_1$ to $R_{12}$ in Chemical Formula 112 and at least one of $R_2$, $R_4$ to $R_{12}$, $R_7'$ to $R_{12}'$ in Chemical Formula 113 may be substituted with a substituent selected from the group consisting of a nitrile, a nitro, an amide, a carbonyl, and a substituted or unsubstituted heterocycle, which reinforces an electron injection or transport capability and thereby makes the compound be applicable to an electron injection layer (EIL) or an electron transport layer (ETL). Accordingly, hole transport and electron transport capabilities may be simultaneously improved.

The various substituents of the above-described compound represented by the above Chemical Formulae 112 and 113 may not change principal properties of the compound for an organic photoelectric device according to one embodiment.

Examples of the compounds for an organic photoelectric device according to an embodiment may include compounds represented by the following Chemical Formulae 114 to 183, but are not limited thereto.

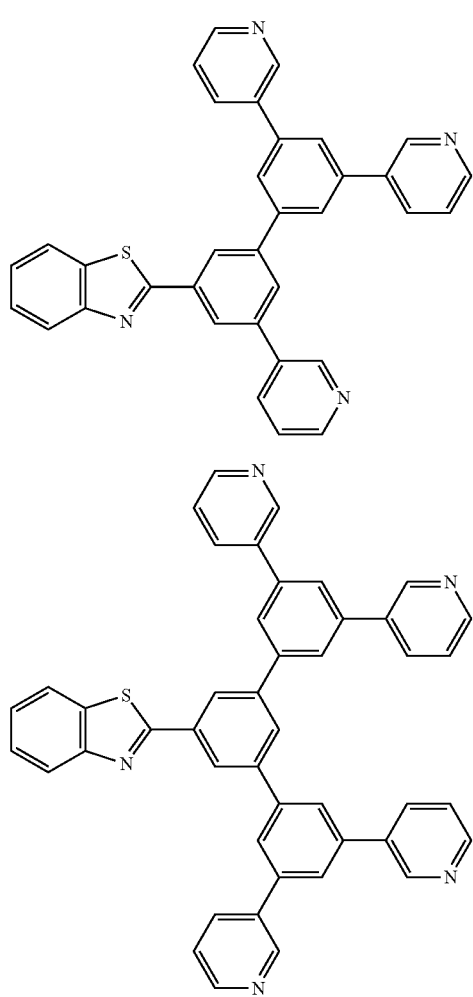

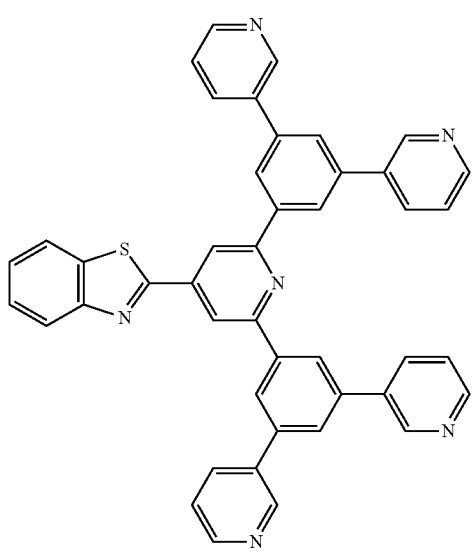

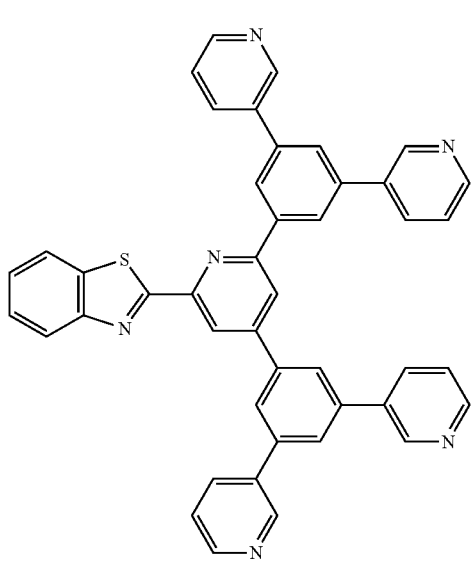

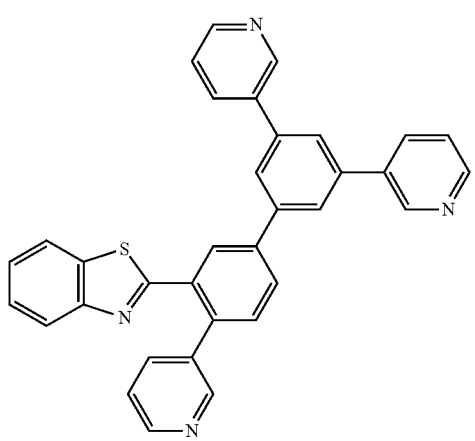

119
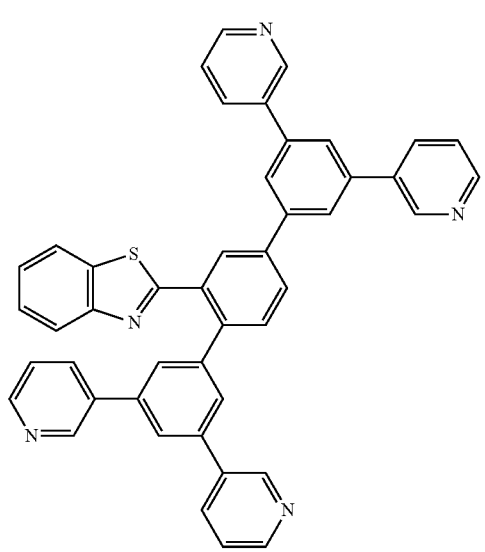
120
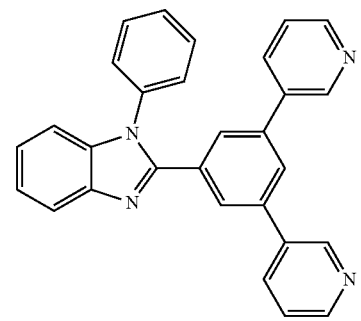
121
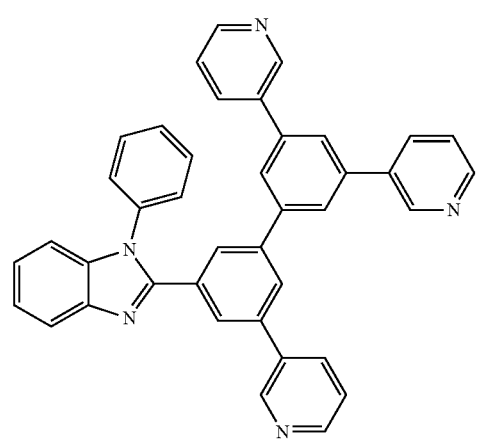
122
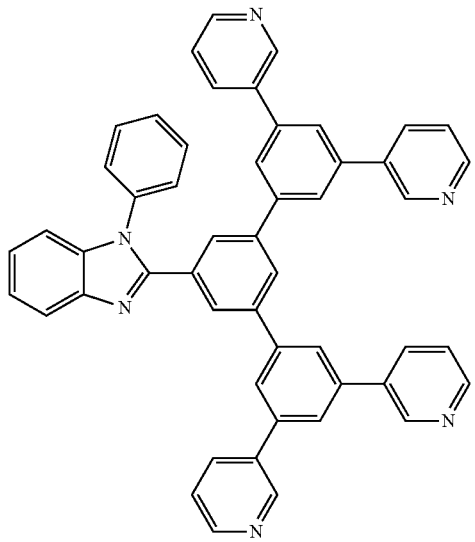
123
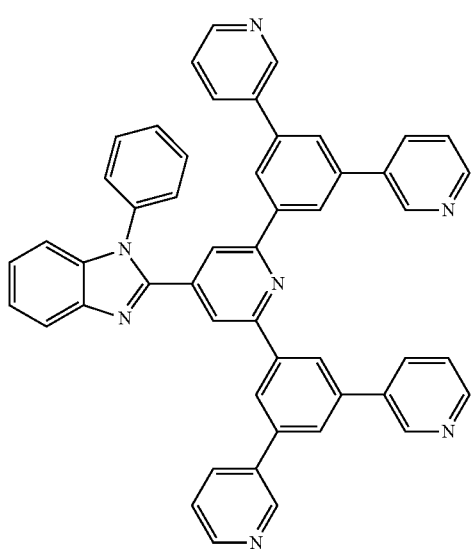
124
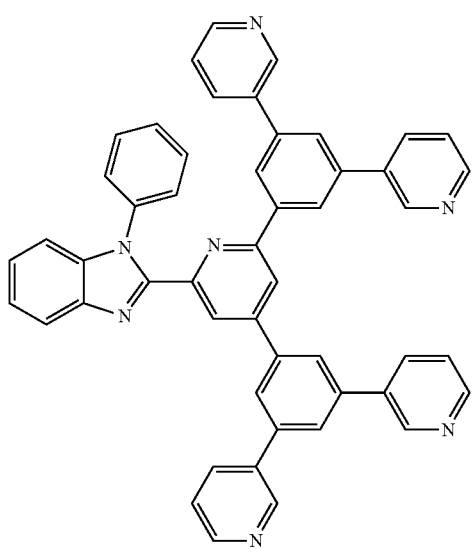

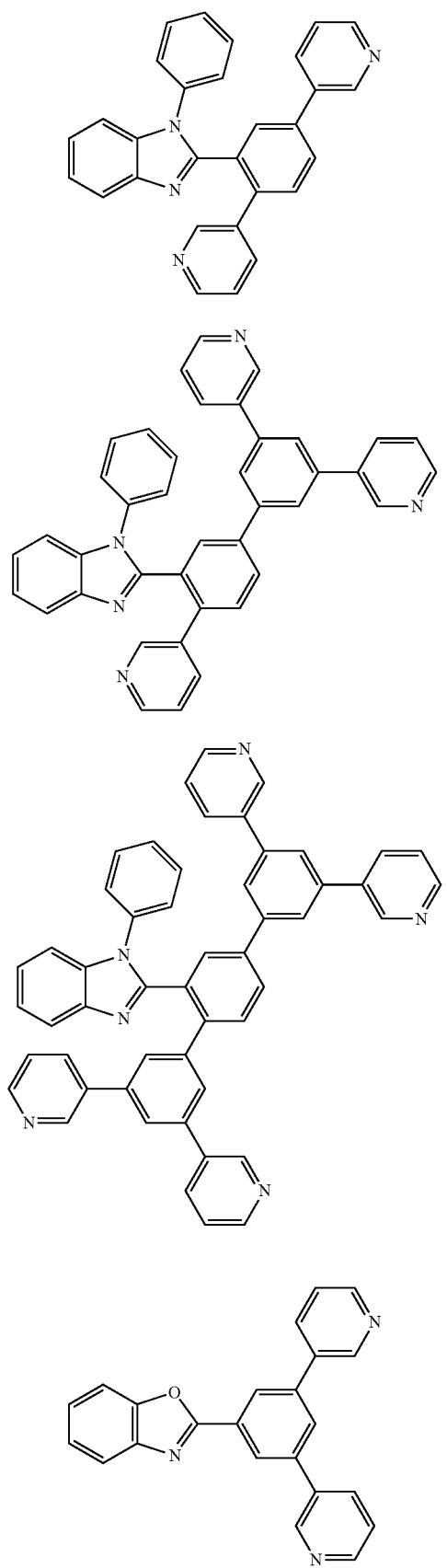

132
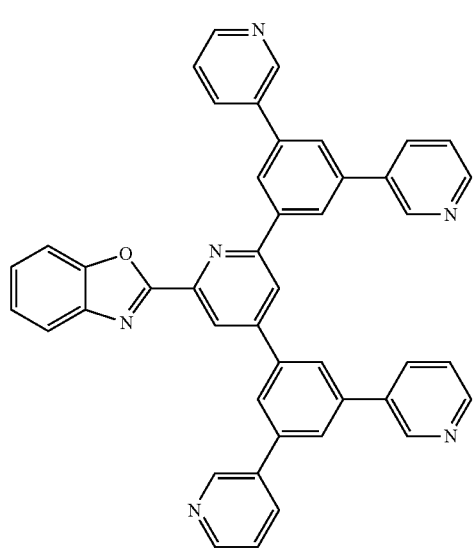
135
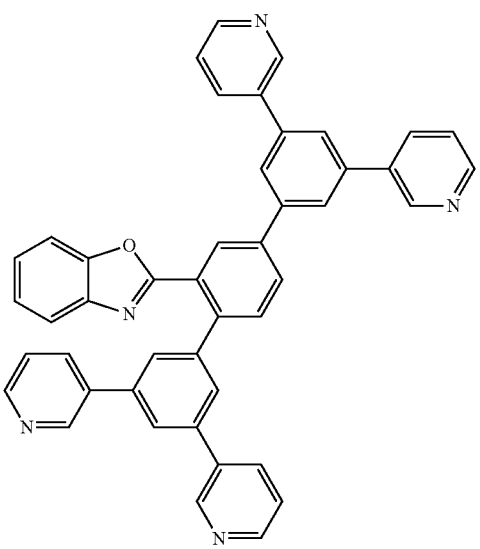
133
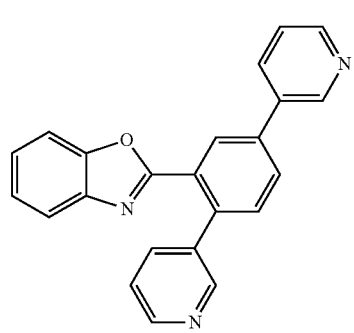
136
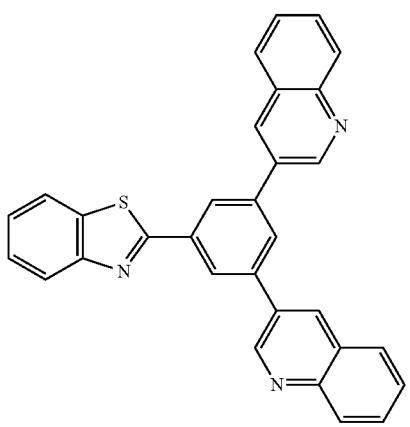
134
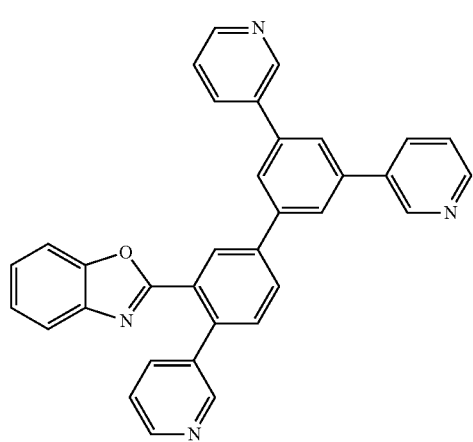
137
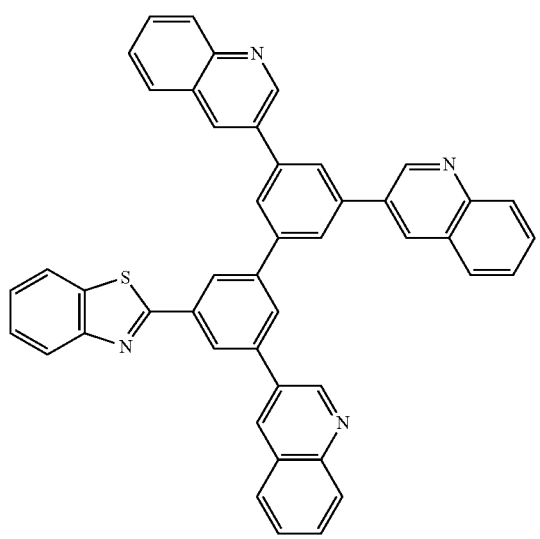

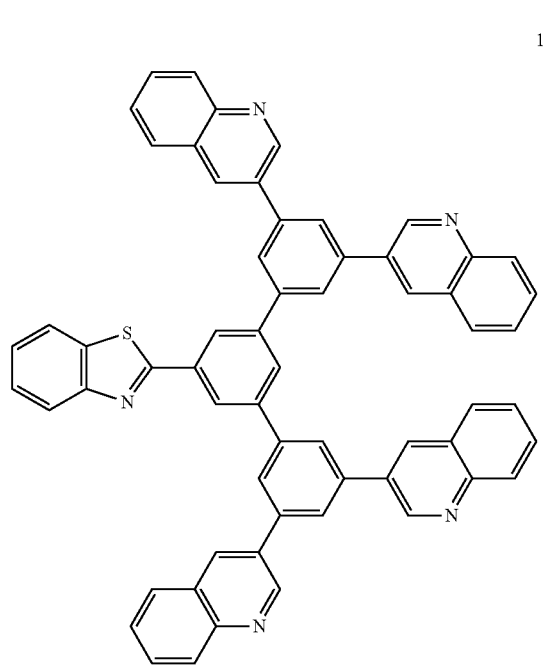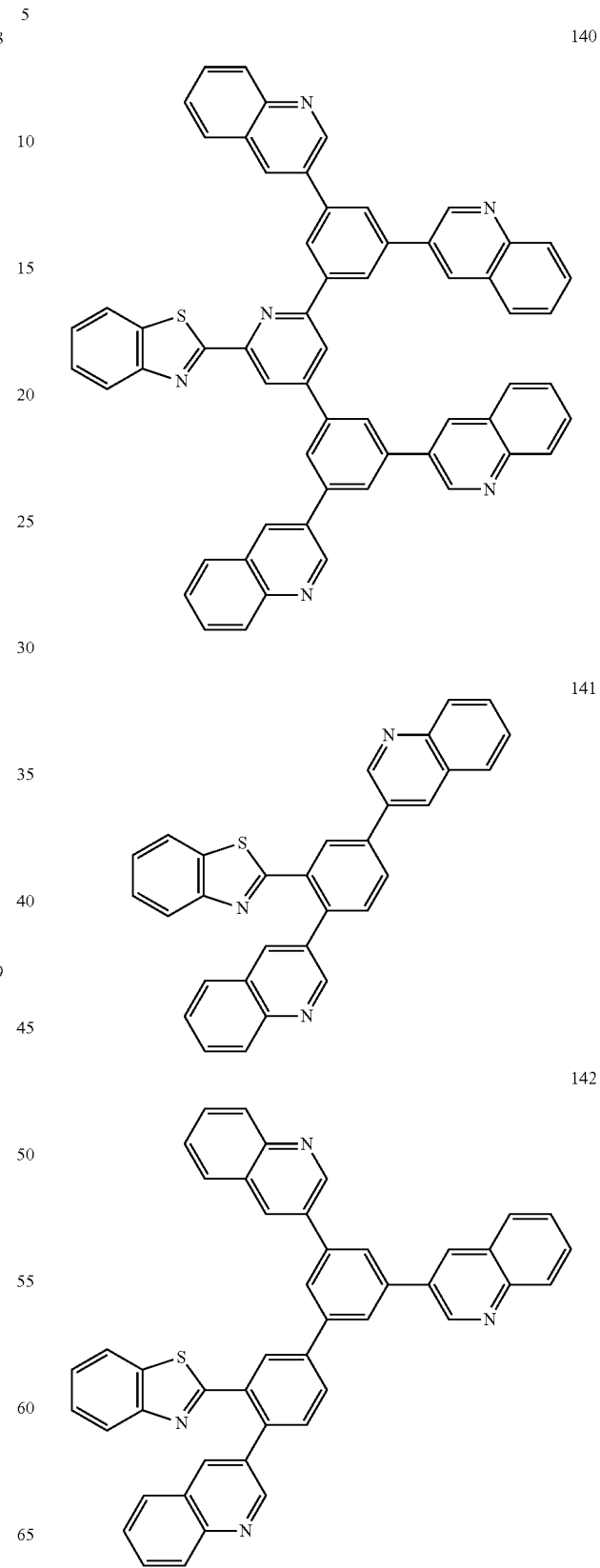

143
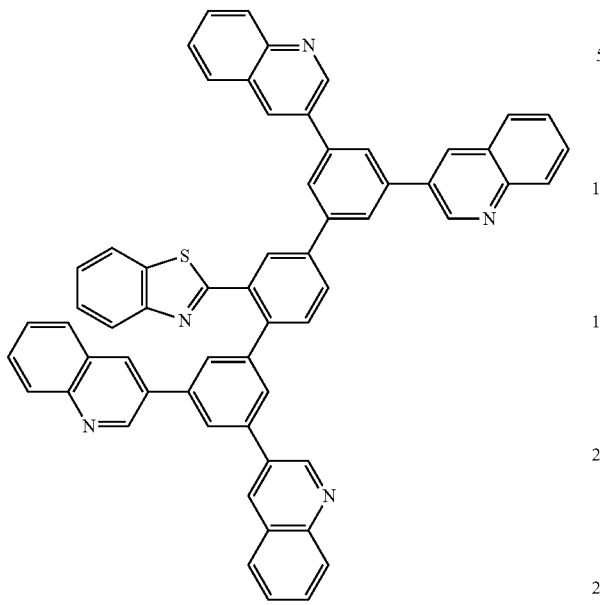
144
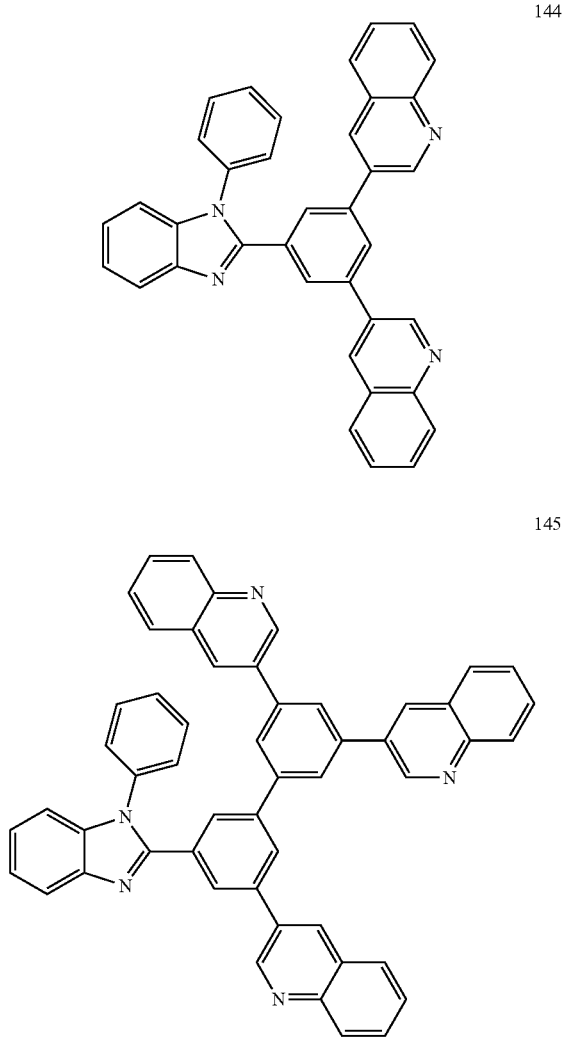
145
146
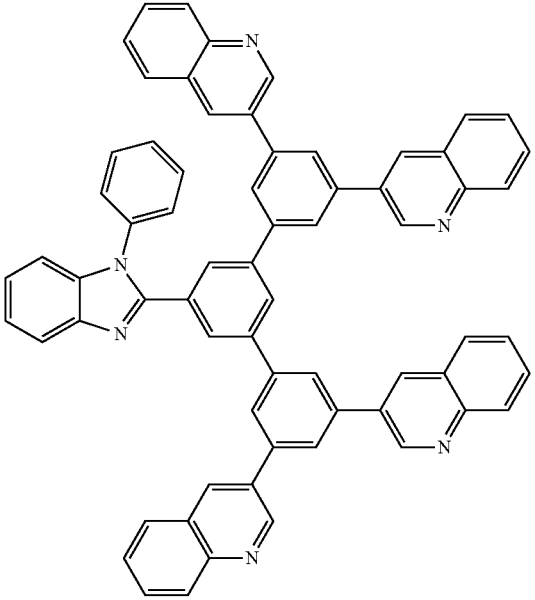
147
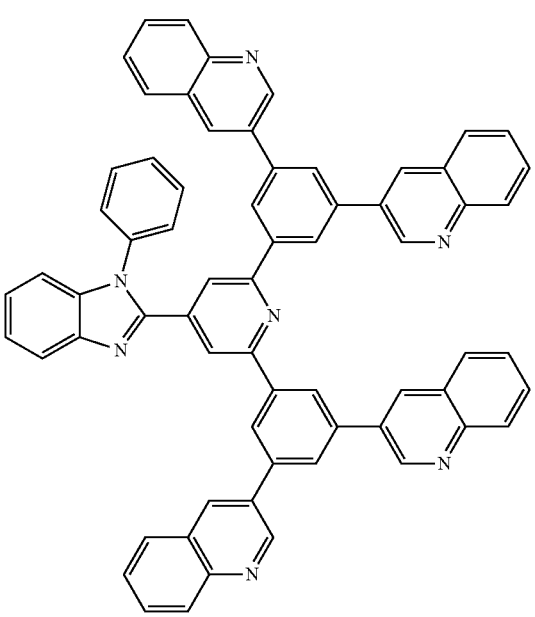

148
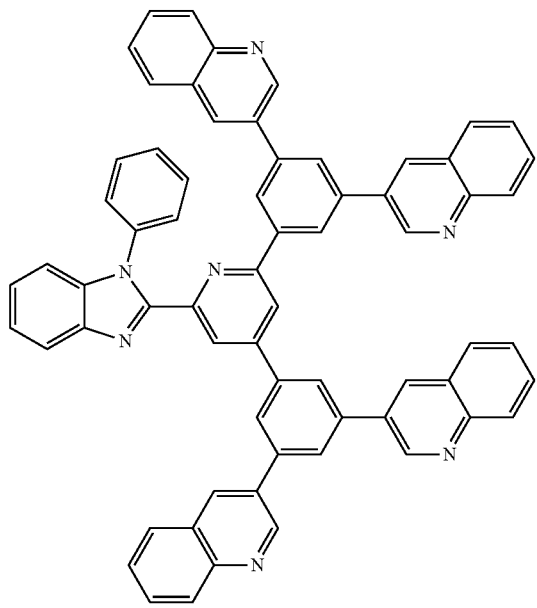
149
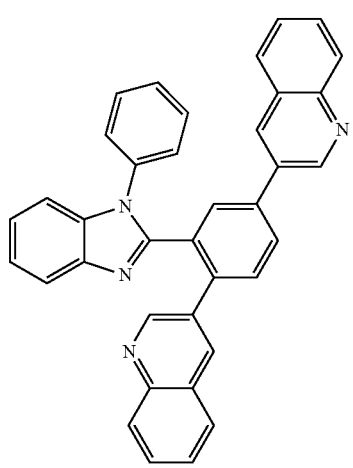
150
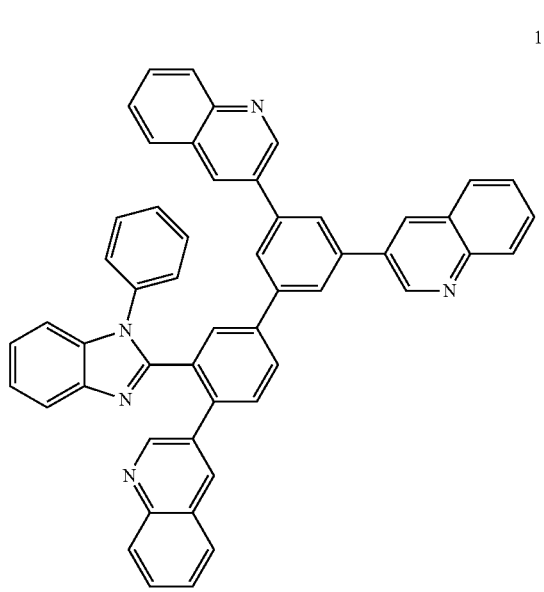
151
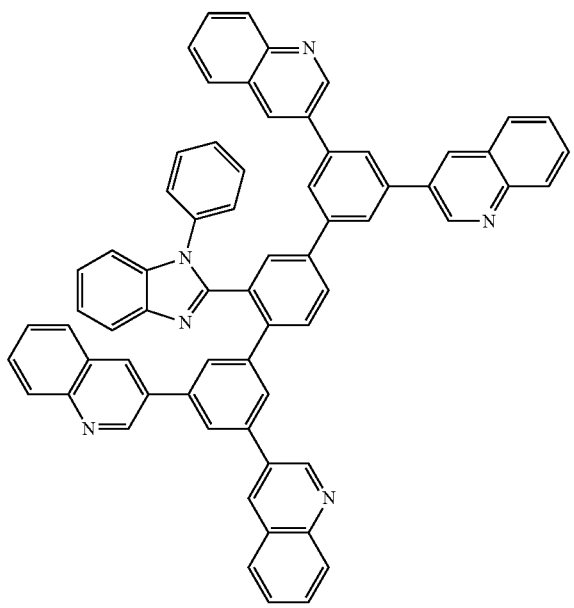
152
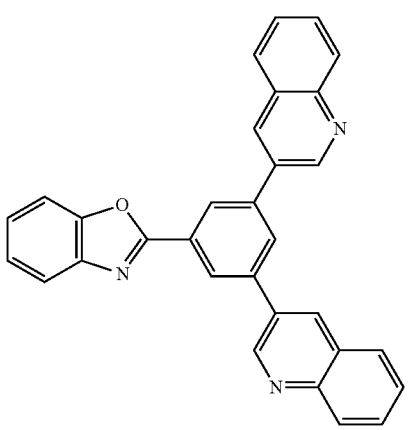
153
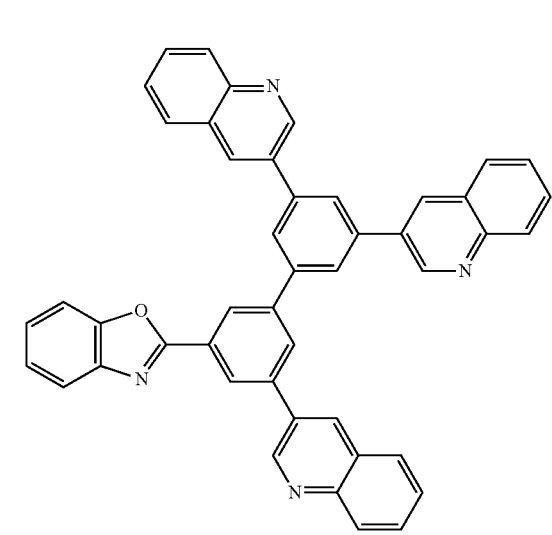

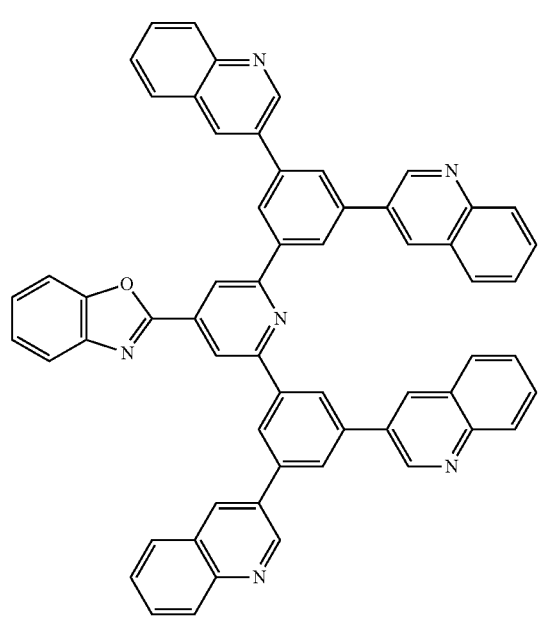
154
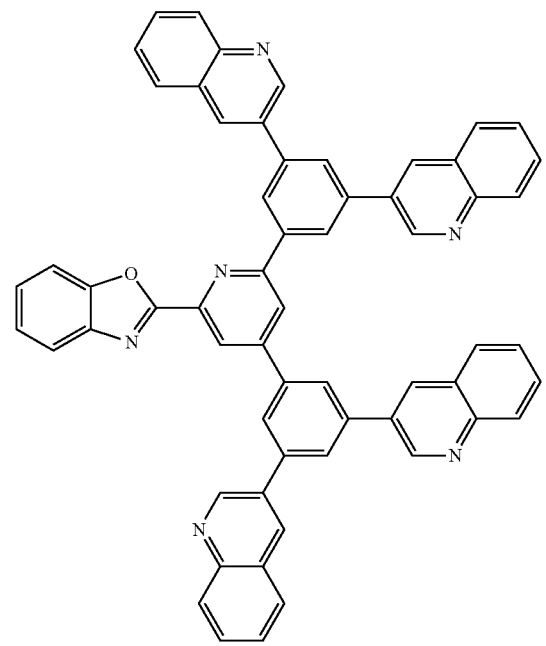
156
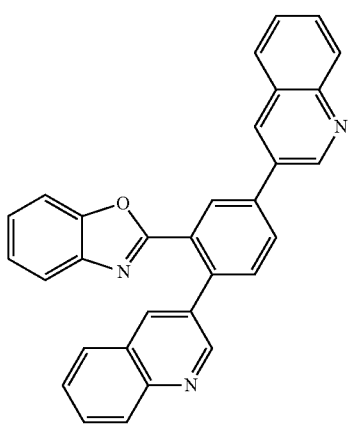
157
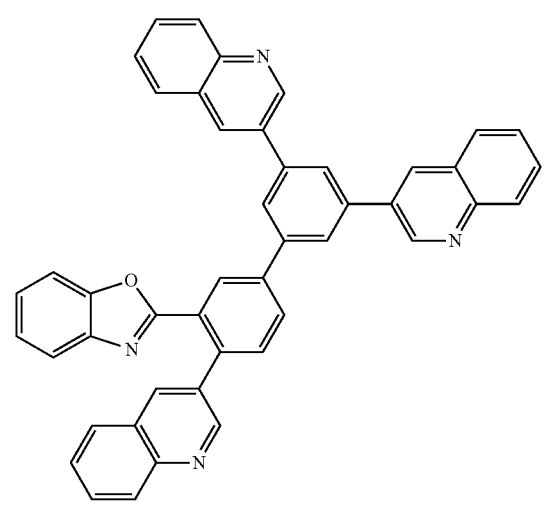
155
158

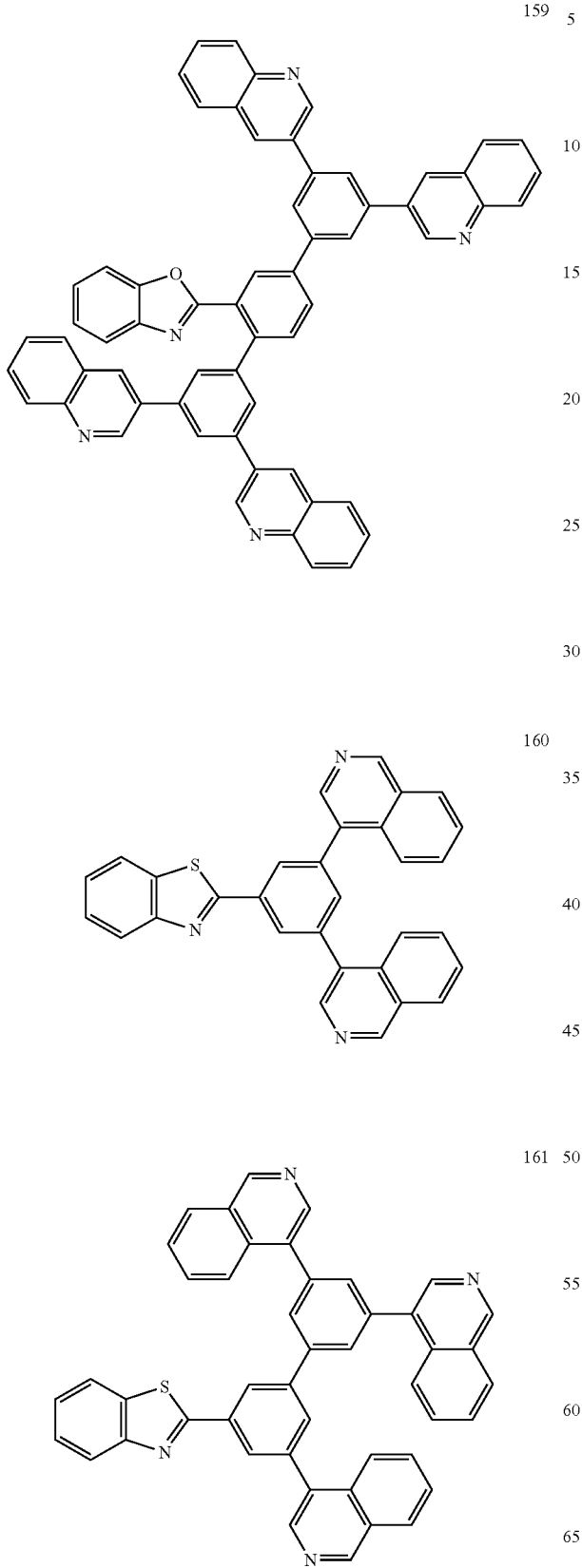

-continued
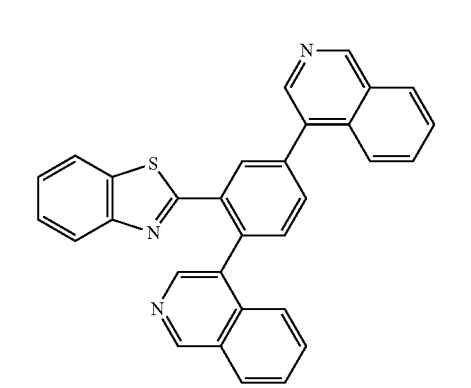
165
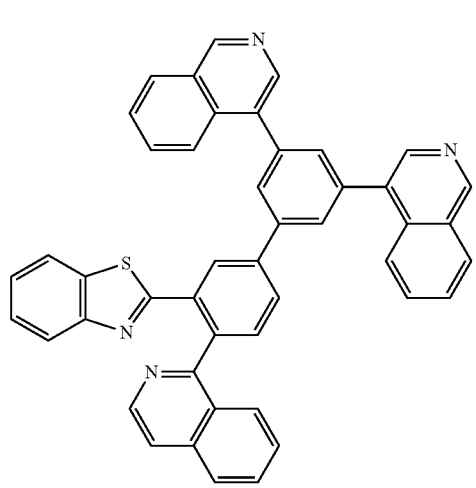
166
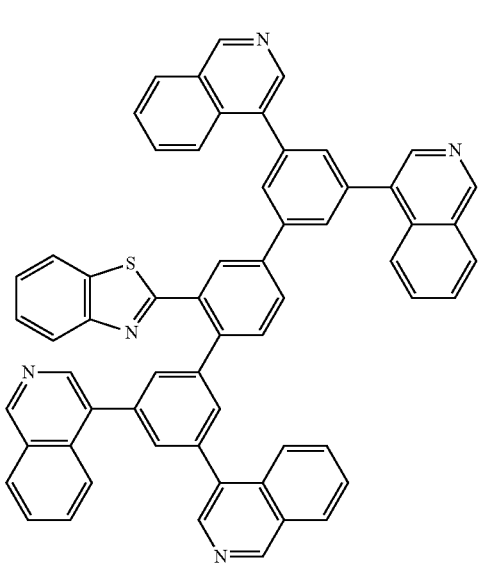
167
-continued
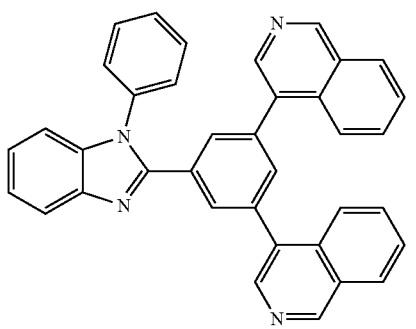
168
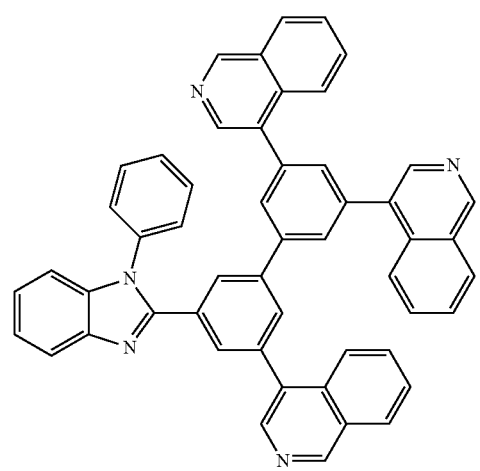
169
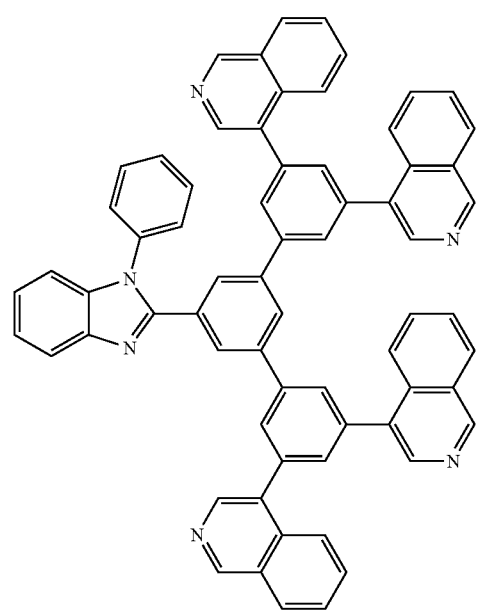
170

171
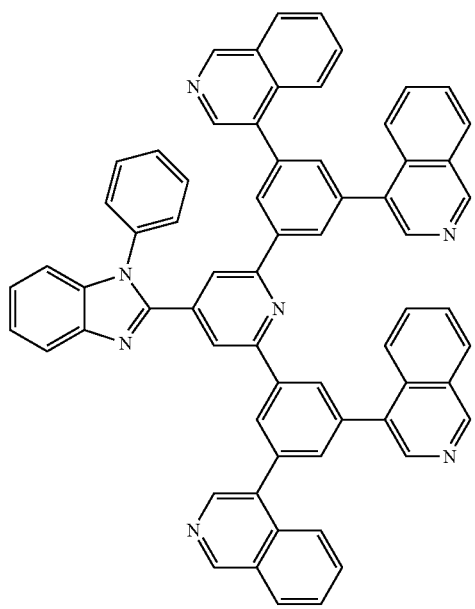
172
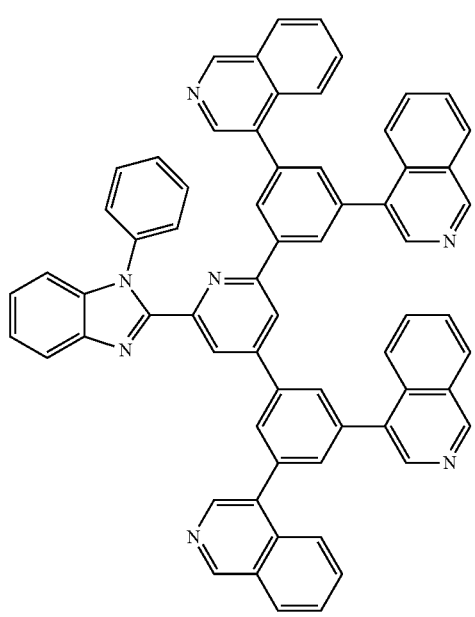
173
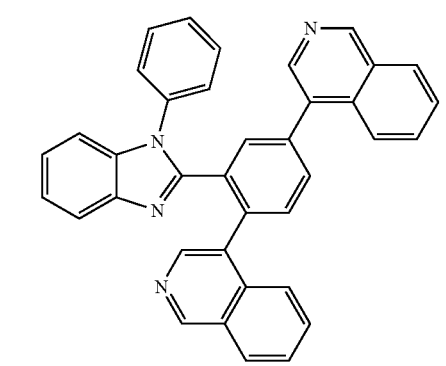
174
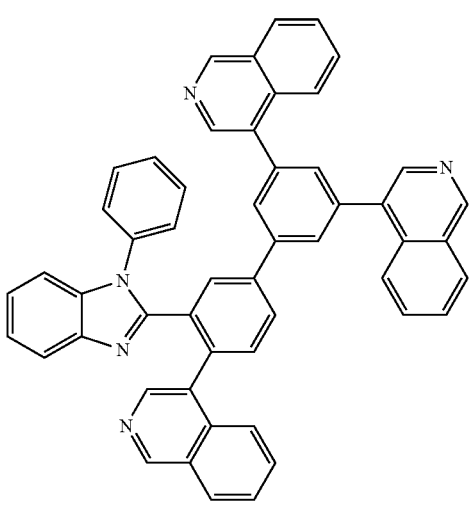
175
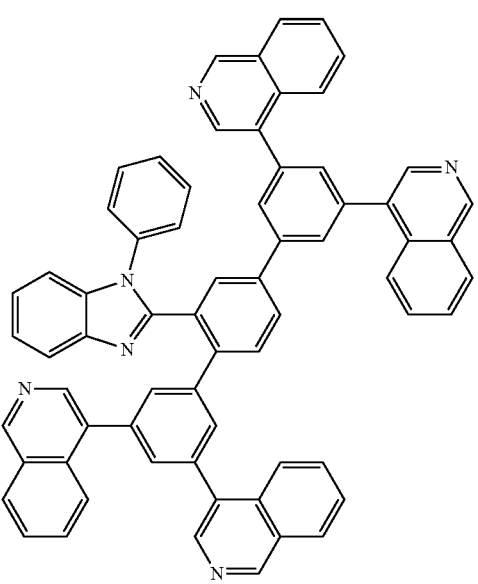
176
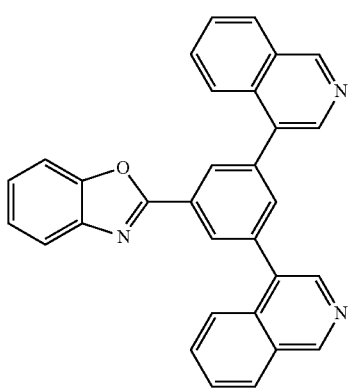

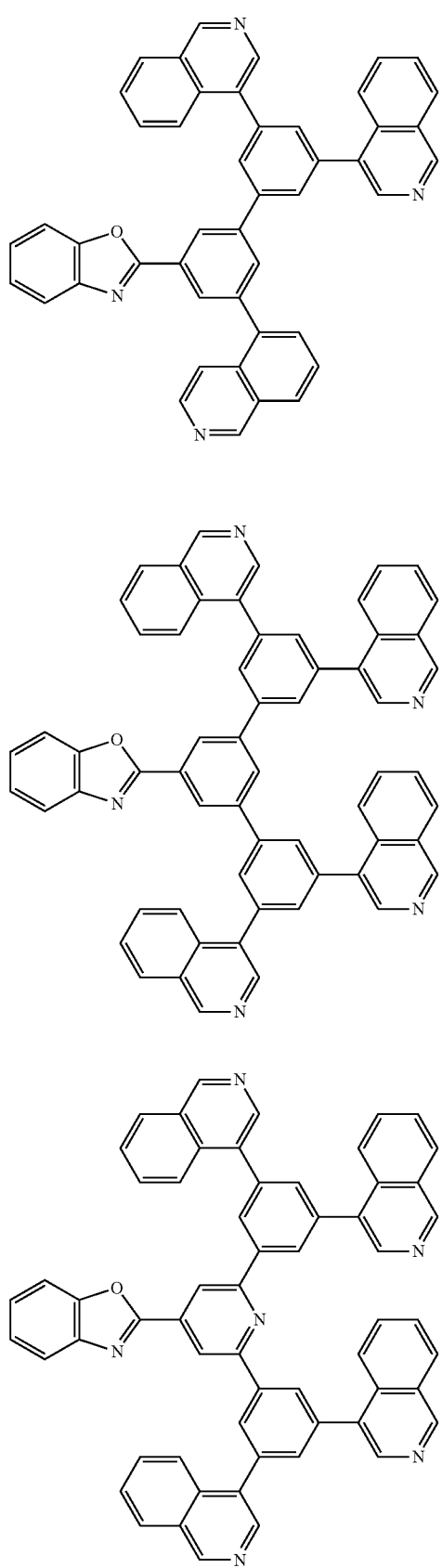
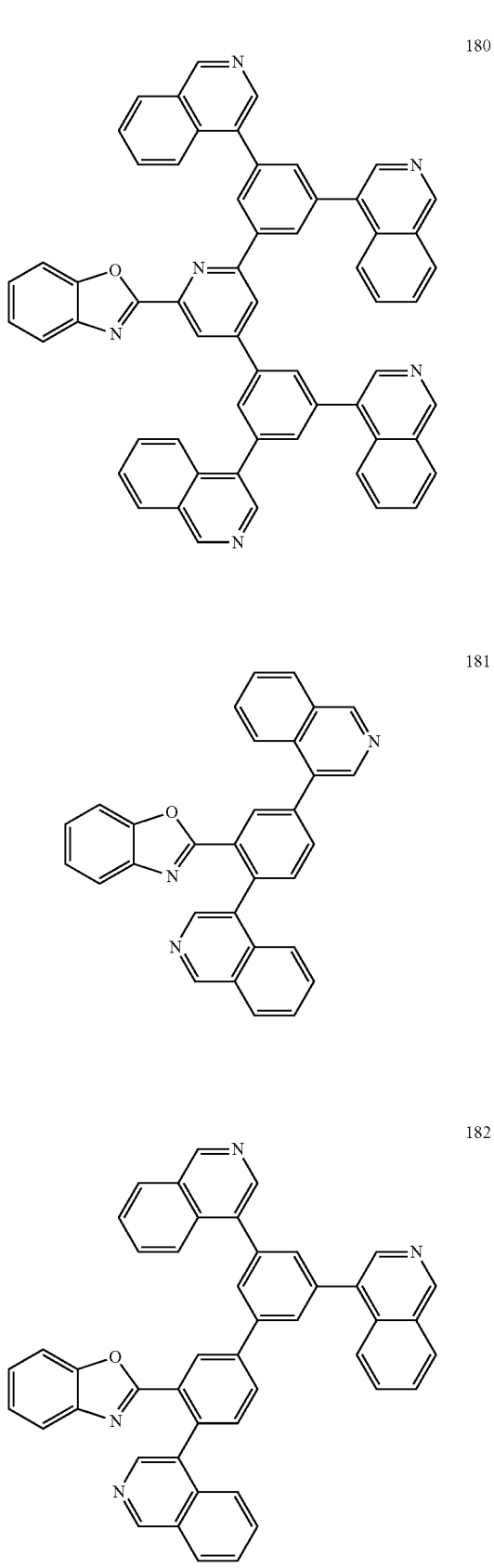 [SMILES: c1ccc2c(-c3cc(-c4cc(-c5cc(-c6cncc7ccccc67)cc(-c6cncc7ccccc67)c5)nc(-c5nc6ccccc6o5)c4)cc(-c4cncc5ccccc45)c3)cncc2c1 ; c1ccc2c(-c3ccc(-c4cncc5ccccc45)c(-c4nc5ccccc5o4)c3)cncc2c1 ; c1ccc2c(-c3cc(-c4ccc(-c5cncc6ccccc56)c(-c5nc6ccccc6o5)c4)cc(-c4cncc5ccccc45)c3)cncc2c1]

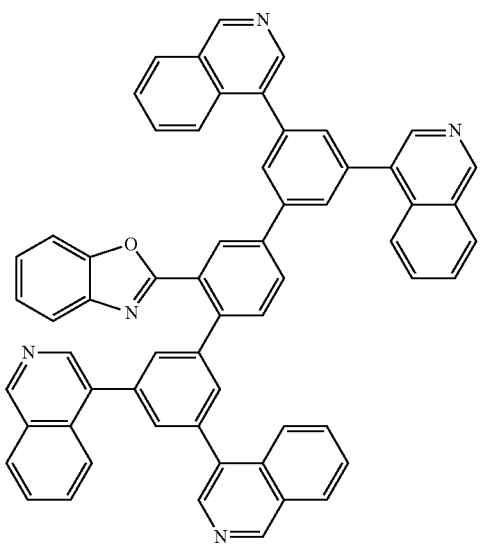

183

The compound for an organic photoelectric device including one of the above compounds may play a role of hole injection, hole transport, light emitting, or electron injection and/or transport, and also as a light emitting host with an appropriate dopant. The compound for an organic photoelectric device may improve thermal stability and may decrease a driving voltage, thereby improving life-span and efficiency characteristics of an organic photoelectric device when included in an organic thin layer.

The compound for an organic photoelectric device including the above compound may play a role of hole and electron transport, and also as a light emitting host with an appropriate dopant. For example, the dopant may be a reducing dopant. The reducing dopant may be selected from the group of an alkaline metal, an alkaline earth metal, a rare earth element metal, an oxide of an alkaline metal, a halide of an alkaline metal, an organic complex of an alkaline metal, an oxide of an alkaline earth metal, a halide of an alkaline earth metal, an organic complex of an alkaline earth metal, an oxide of an alkaline earth metal, a halide of an alkaline earth metal, an organic complex of an alkaline earth metal, an oxide of a rare earth element metal, a halide of a rare earth element metal, and an organic complex of a rare earth element metal.

The compound for an organic photoelectric device may be usefully used for a host material or a charge transfer material. In an implementation, the organic photoelectric device may include an organic light emitting diode, an organic solar cell, an organic transistor, an organic memory device, and the like.

As for an organic solar cell, the compound of an embodiment may be included in an electrode or an electrode buffer layer and may thereby improve quantum efficiency. As for an organic transistor, the compound can be used as an electrode material in a gate, a source-drain electrode, and the like.

Hereinafter, an organic light emitting diode is illustrated in more detail. An organic photoelectric device according to an embodiment may include the compound for an organic photoelectric device in at least one layer among organic thin layers, when an organic photoelectric device in general includes an anode, a cathode, and at least one organic thin layer disposed between the anode and cathode.

An organic light emitting diode may include a compound having various energy band gaps, and may thereby satisfy various conditions desirable for a hole injection layer (HIL), a hole transport layer (HTL), an emission layer, an electron injection layer (EIL), an electron transport layer (ETL), and the like. Accordingly, the organic light emitting diode may realize a low driving voltage and high luminous efficiency.

The organic thin layer may include one selected from the group of an emission layer, an electron transport layer (ETL), an electron injection layer (EIL), a hole transport layer (HTL), a hole injection layer (HIL), and a hole blocking layer. At least one layer may include the compound for an organic photoelectric device according to an embodiment.

FIGS. 1 to 5 illustrate cross-sectional views showing organic photoelectric devices including the organic compounds according to various embodiments.

Referring to FIGS. 1 to 5, the organic photoelectric devices 100, 200, 300, 400, and 500 according to an embodiment may include at least one organic thin layer 105 interposed between an anode 120 and a cathode 110.

The anode 120 may include an anode material having a large work function to help hole injection into an organic thin layer. The anode material may include a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as $ZnO:Al$ or $SnO_2:Sb$; or a conductive polymer such as poly(3-methylthiophene), poly[3,4-(ethylene-1,2-dioxy)thiophene] (PEDT), polypyrrole, and polyaniline, but is not limited thereto.

The cathode 110 may include a cathode material having a small work function to help electron injection into an organic thin layer. The cathode material may include a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca, but is not limited thereto.

Referring to FIG. 1, the organic photoelectric device 100 may include an organic thin layer 105 including only an emission layer 130.

Figure 2:
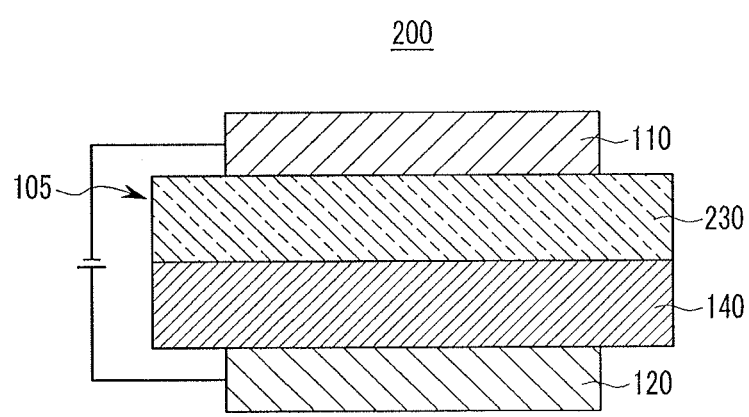

Referring to FIG. 2, a double-layered organic photoelectric device 200 may include an organic thin layer 105 including an emission layer 230 including an electron transport layer (ETL), and a hole transport layer (HTL) 140. The emission layer 130 also functions as an electron transport layer (ETL), and the hole transport layer (HTL) 140 layer has an excellent binding property with a transparent electrode such as ITO or an excellent hole transporting property.

Figure 3:
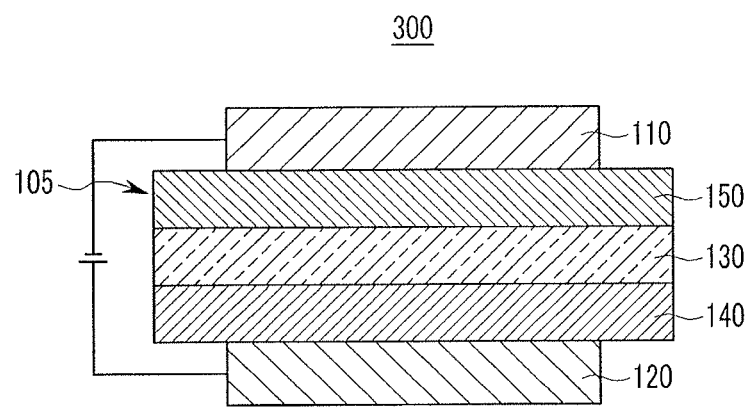

Referring to FIG. 3, a three-layered organic photoelectric device 300 may include an organic thin layer 105 including an electron transport layer (ETL) 150, an emission layer 130, and a hole transport layer (HTL) 140. The emission layer 130 is independently installed, and layers having an excellent electron transporting property or an excellent hole transporting property are separately stacked.

Figure 4:
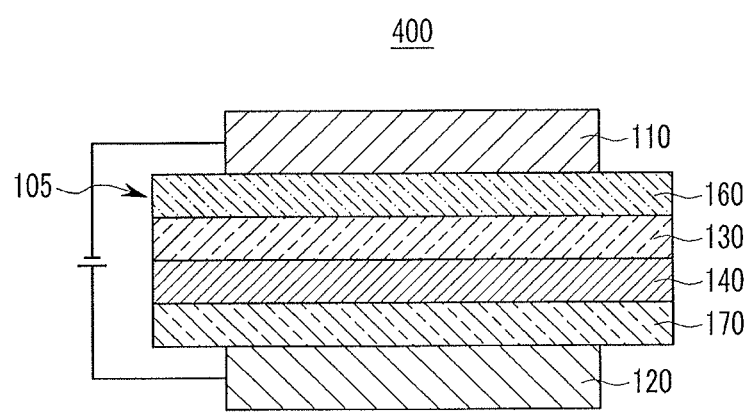

As shown in FIG. 4, a four-layered organic photoelectric device 400 may include an organic thin layer 105 including an electron injection layer (EIL) 160, an emission layer 130, a hole transport layer (HTL) 140, and a hole injection layer (HIL) 170 for binding with the anode 120 of, e.g., ITO.

Figure 5:
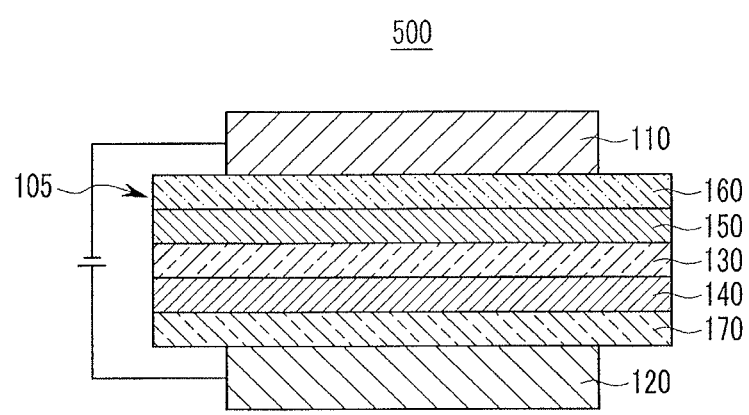
Figure 6:
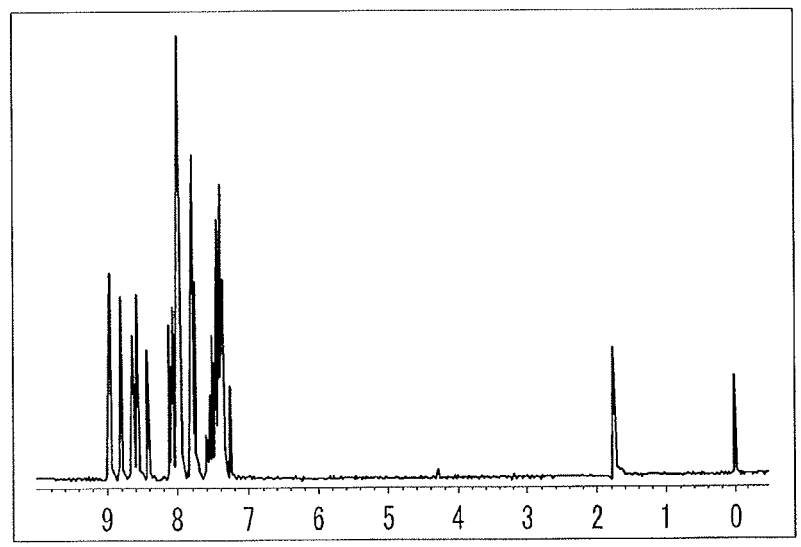
FIGS. 6-14 illustrate $^1$H NMR spectra of compounds according to Examples 1 to 9, respectively.
Figure 7:
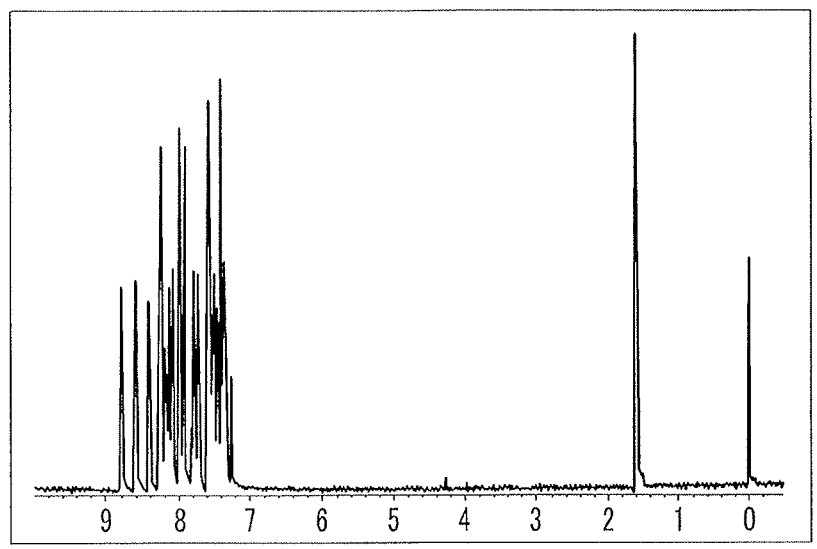
Figure 8:
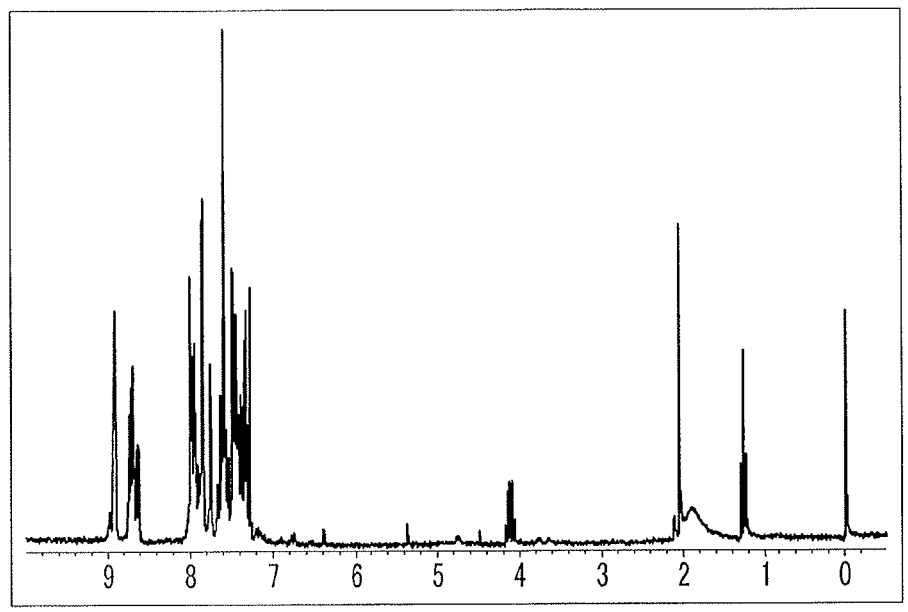
Figure 9:
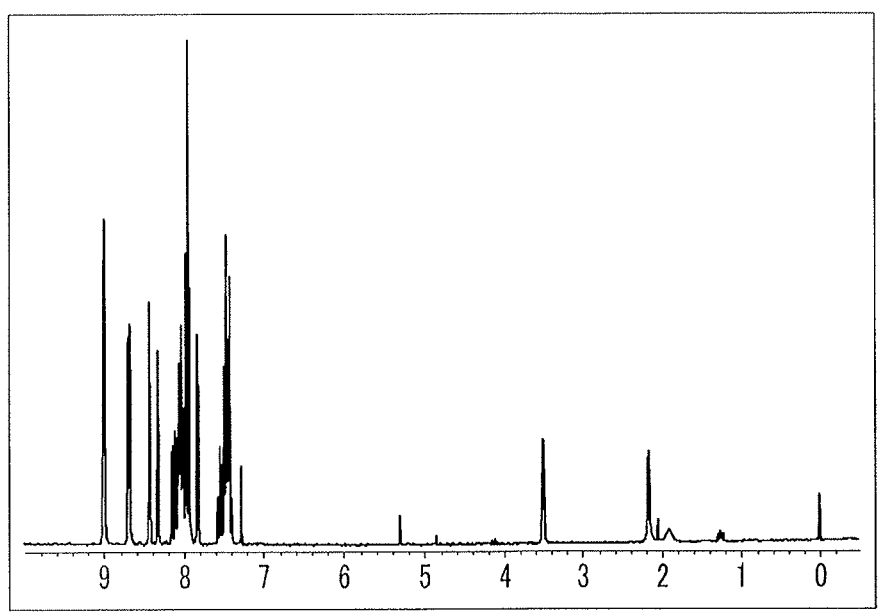
Figure 10:
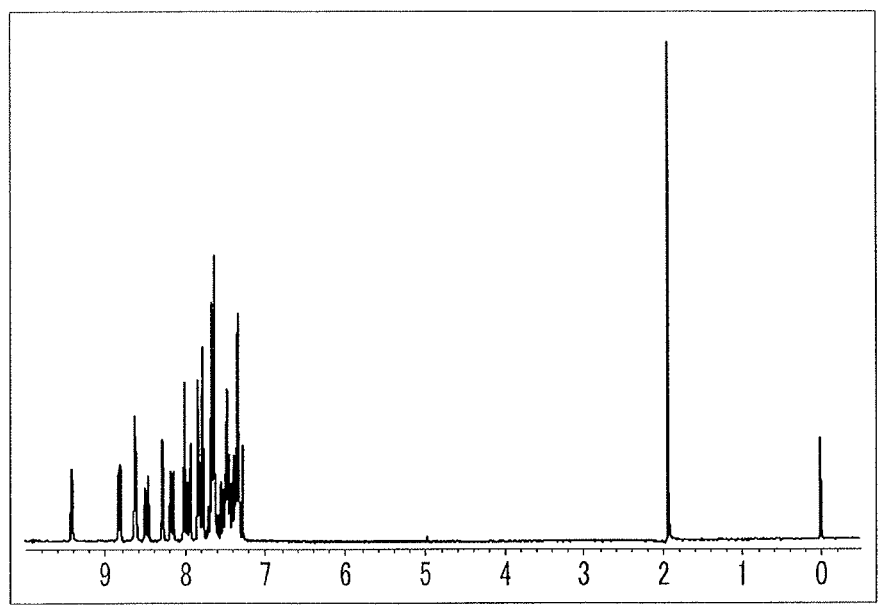
Figure 11:
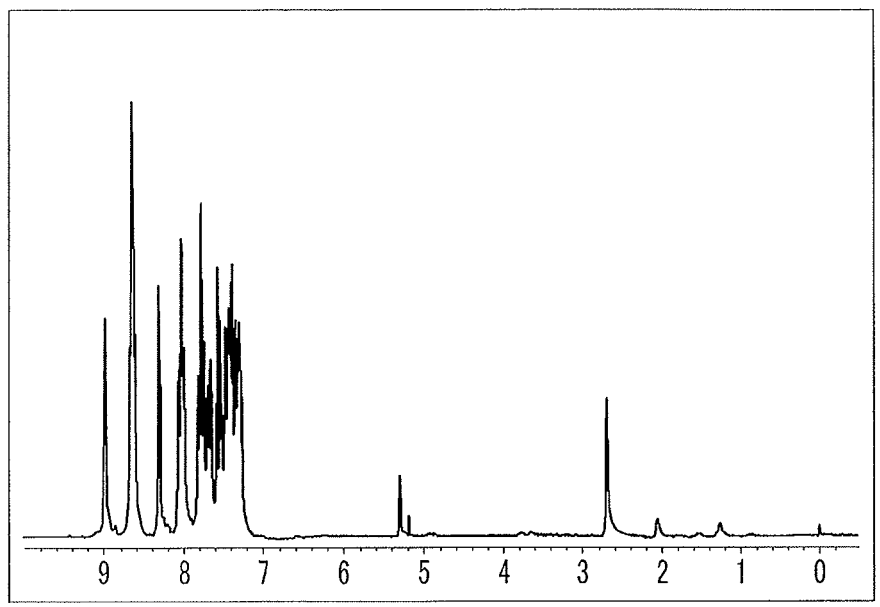
Figure 12:
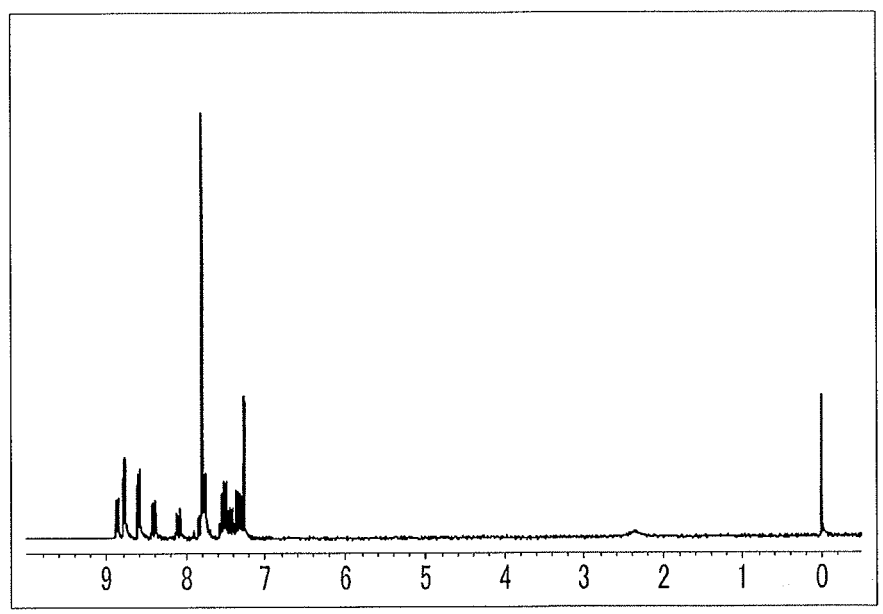
Figure 13:
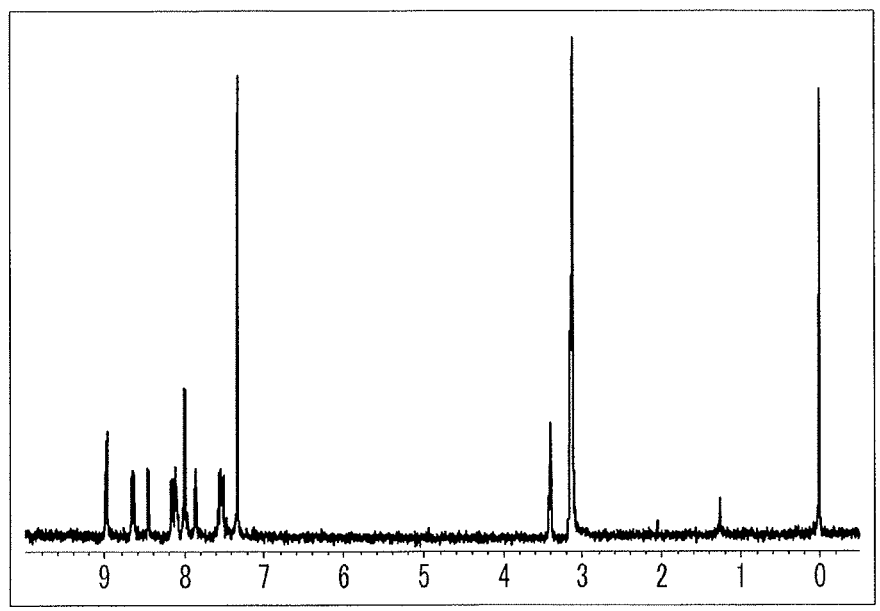
Figure 14:
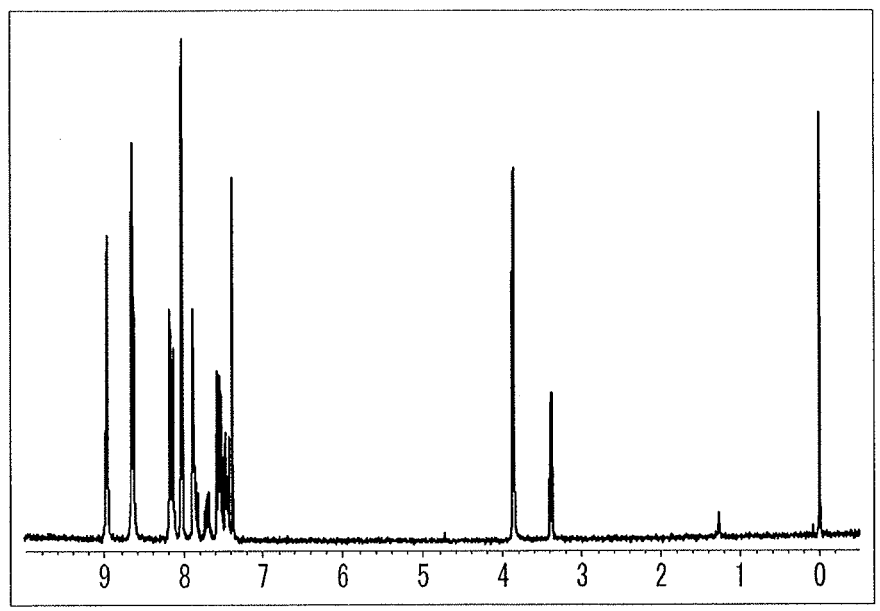

As shown in FIG. 5, a five layered organic photoelectric device 500 may include an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

The light emitting diode may be fabricated by forming an anode on a substrate, forming an organic thin layer, and forming a cathode thereon. The organic thin layer may be formed by a dry coating method such as evaporation, sputtering, plasma plating, and ion plating, or a wet coating method such as spin coating, dipping, and flow coating.

Another embodiment provides a display device including the organic photoelectric device according to the above-described embodiment.

The following Examples and Comparative Examples are provided in order to set forth particular details of one or more embodiments. However, it will be understood that the embodiments are not limited to the particular details described. Further, the Comparative Examples are set forth to highlight certain characteristics of certain embodiments, and are not to be construed as either limiting the scope of the invention as exemplified in the Examples or as necessarily being outside the scope of the invention in every respect.

Synthesis Example 1

Synthesis of 2-(3-(anthracen-9-yl)-5-bromophenyl)benzo[d]oxazole

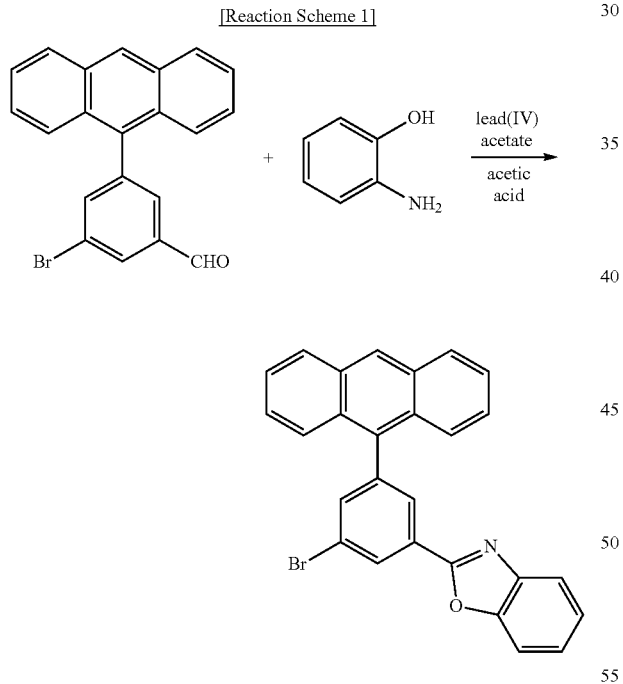

[Reaction Scheme 1]

10 g (27.7 mmol) of 3-(anthracen-9-yl)-5-bromobenzaldehyde and 3.6 g (33.2 mmol) of 2-aminophenol were dissolved in 100 ml of acetic acid, and then agitated at room temperature for 30 minutes. Next, 14.7 g (33.2 mmol) of lead (IV) acetate was added thereto. The resulting mixture was agitated at 50° C. for 1 hour. Then, water was poured therein. The resulting product was treated with ethyl acetate to perform extraction, and then the solvent was removed under a reduced pressure. The extract was separated through a column and dried, obtaining 4.5 g (Y=33%) of a white solid.

Synthesis Example 2

Synthesis of 2-(4-(4,4,5,5-tetramethyl-1,3,2-dioxaborolan-2-yl)phenyl)-5-phenyl-1,3,4-oxadiazole

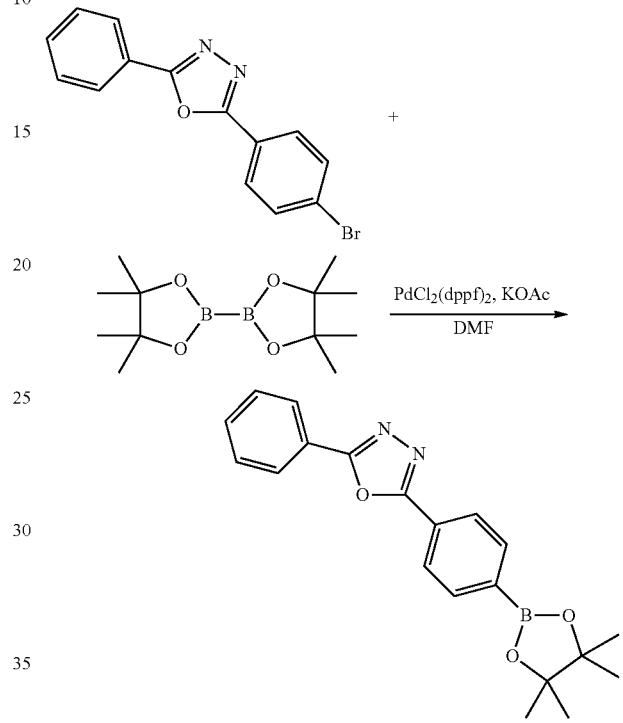

[Reaction Scheme 2]

5 g (16.6 mmol) of 2-(4-bromophenyl)-5-phenyl-1,3,4-oxadiazole, 5.1 g (19.9 mmol) of bis(pinacolato)diboron, 0.41 g (3 mol %) of a complex of [1,1′-bis(diphenylphosphino)ferrocene]dichloro-palladium (II) with dichloromethane, and 4.9 g (49.8 mmol) of potassium acetate were dissolved in 100 ml of dimethylformamide (DMF). The solution was reacted at 80° C. for 12 hours. The reactant was extracted with ethyl acetate. The extract was treated under a reduced pressure to remove the solvent and separated through a column, obtaining 3.1 g (Y=53%) of a light yellow solid.

Synthesis Example 3

Synthesis of 2-(3,5-dibromophenyl)-1-phenyl-1H-benzo[d]imidazole

[Reaction Scheme 3]

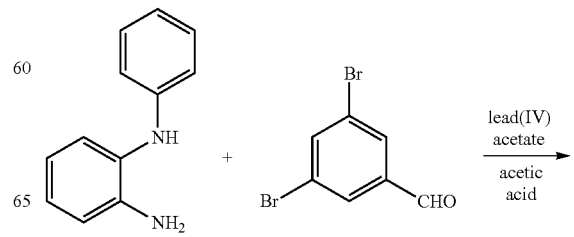

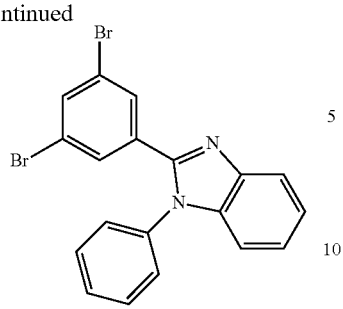

20 g (75.8 mmol) of 3,5-dibromobenzaldehyde and 16.8 g (90.9 mmol) of N-phenyl-o-phenylenediamine were dissolved in 150 mL of acetic acid. The solution was agitated at room temperature for 30 minutes. Next, 37 g (83.4 mmol) of lead(IV) acetate was added thereto. The resulting product was agitated at 50° C. for 1 hour. Then, water was poured into the obtained reactant. The resulting product was treated with ethyl acetate to perform extraction and the solvent was removed under a reduced pressure. The extract was separated through a column and dried, obtaining 9.5 g (Y=29%) of a yellow solid.

Synthesis Example 4

Synthesis of 2-(3-bromo-5-(pyridin-3-yl)phenyl)-1-phenyl-M-benzo[d]imidazole

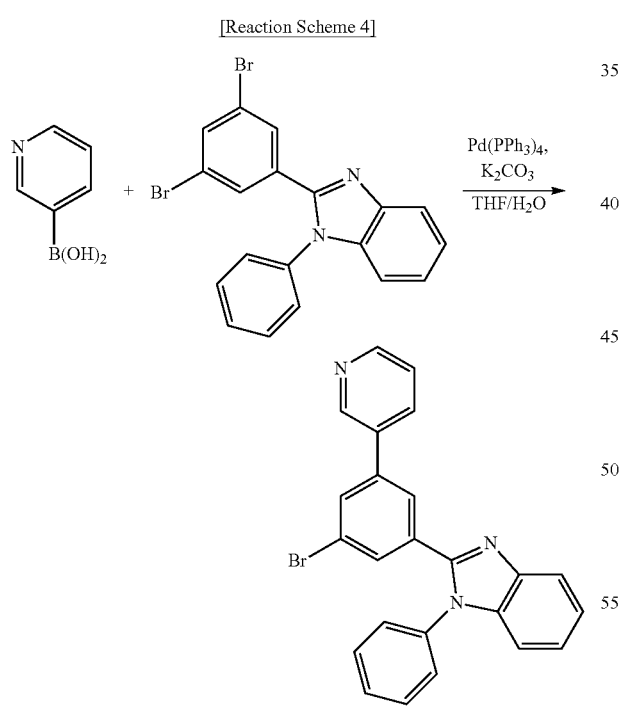

9.4 g (22.0 mmol) of 2-(3,5-dibromophenyl)-1-phenyl-1H-benzo[d]imidazole according to Synthesis Example 3, 2.7 g (22.0 mmol) of pyridine-3-boronic acid, 0.76 g (3 mol %) of tetrakis(triphenylphosphine)palladium (0), and 6.1 g (44.0 mmol) of potassium carbonate were dissolved in 300 ml of tetrahydrofuran/H₂O mixed in a volume ratio of 2/1. The solution was reacted at 80° C. for 12 hours. The obtained reactant was extracted with ethyl acetate and treated under a reduced pressure to remove the solvent therein. The reactant was separated through a column and dried, obtaining 5.15 g (Y=54%) of a yellow solid.

Synthesis Example 5

Synthesis of 2-(3,5-dibromophenyl)benzo[d]thiazole

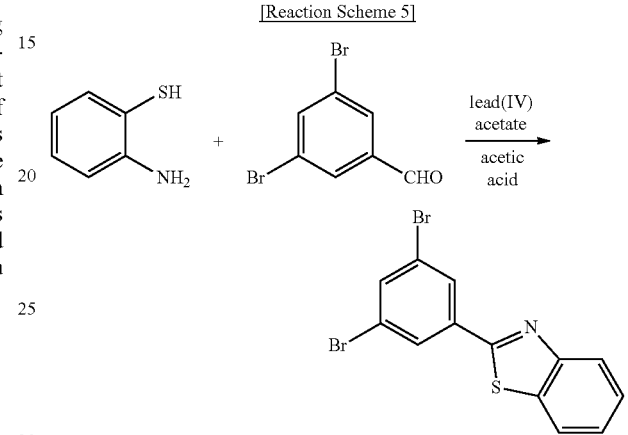

5.03 g (19.1 mmol) of 3,5-dibromobenzaldehyde and 3.1 mL (28.6 mmol) of 2-aminothiophenol were dissolved in 60 mL of acetic acid. The solution was agitated at room temperature for 30 minutes. 9.78 g (21.0 mmol) of lead(IV) acetate was added thereto. The resulting mixture was agitated at 50° C. for 1 hour. Then, water was poured into the reactant. It was extracted with ethyl acetate. The extract was separated through a column and dried, obtaining 4.74 g (Y=67%) of a white solid.

Synthesis Example 6

Synthesis of 2-(3-bromo-5-(pyridin-3-yl)phenyl)benzo[d]thiazole

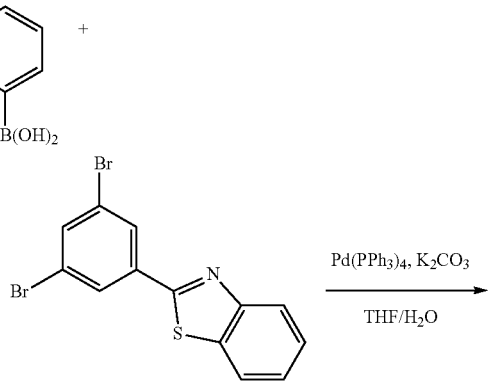

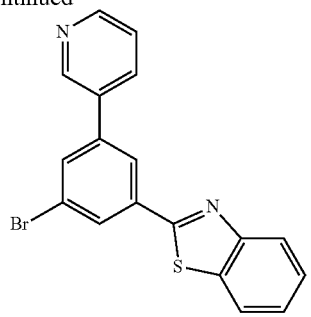

4.74 g (12.8 mmol) of 2-(3,5-dibromophenyl)benzo[d]thiazole) according to Synthesis Example 5, 1.89 g (15.4 mmol) of pyridine-3-boronic acid, 0.44 g (3 mol %) of tetrakis(triphenylphosphine)palladium (0), and 5.31 g (38.4 mmol) of potassium carbonate were dissolved in 50 ml of tetrahydrofuran/$H_2O$ mixed in a volume ratio of 4/1. The solution was reacted at 80° C. for 12 hours. The obtained reactant was extracted with ethyl acetate and treated under a reduced pressure to remove the solvent. The extract was separated through a column and dried, obtaining 2.54 g (Y=54%) of a white solid.

Synthesis Example 7

Synthesis of 3-(2H-tetrazol-5-yl)pyridine

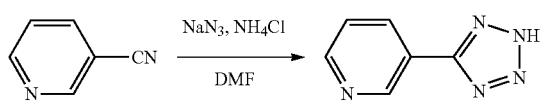

30 g (288 mmol) of 3-pyridinecarbonitrile, 28.1 g (432 mmol) of sodium azide ($NaN_3$), and 23.1 g (432 mmol) of ammonium chloride were dissolved in 200 mL of DMF. The solution was reacted at 100° C. for 24 hours. Then, water was added to the obtained reactant. The resulting product was neutralized with hydrochloric acid and then filtered, obtaining 19.6 g (Y=46%) of a white solid.

Synthesis Example 8

Synthesis of 3-(5-(3-bromophenyl)-1,3,4-oxadiazol-2-yl)pyridine

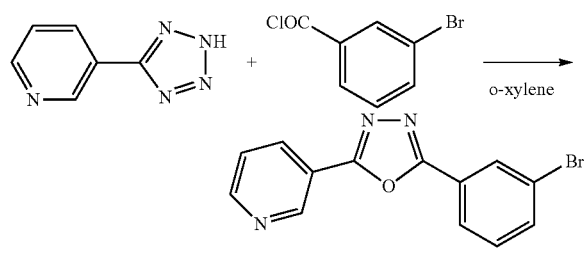

16.8 g (114 mmol) of 3-(2H-tetrazol-5-yl)pyridine) according to Synthesis Example 7 and 25 g (114 mmol) of 3-bromobenzoylchloride were dissolved in 180 mL of o-xylene. The solution was reacted at 150° C. for 8 hours. The obtained reactant was purified under a reduced pressure and washed with methanol, obtaining 30 g (Y=87%) of a white solid.

Synthesis Example 9

Synthesis of 3-(5-(3-(4,4,5,5-tetramethyl-1,3,2-dioxaborolan-2-yl)phenyl)-1,3,4-oxadiazol-2-yl)pyridine

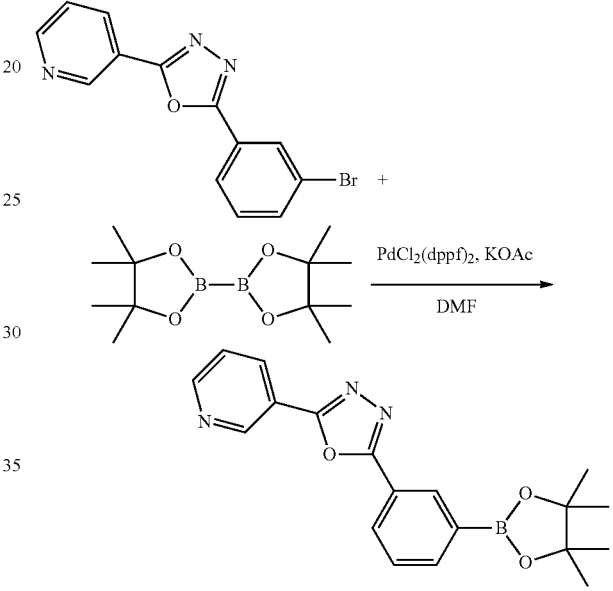

12 g (40 mmol) of 3-(5-(3-bromophenyl)-1,3,4-oxadiazol-2-yl)pyridine according to Synthesis Example 8, 12.2 g (48 mmol) of bis(pinacolato)diboron, 0.98 g (3 mol %) of a complex of [1,1'-bis(diphenylphosphino)ferrocene]dichloro-palladium(II) with dichloromethane, 5.9 g (60 mmol) of potassium acetate were dissolved in 250 ml of dimethylformamide (DMF). The solution was reacted at 80° C. for 12 hours. The obtained reactant was extracted with ethyl acetate and treated under a reduced pressure to remove the solvent. The extract was separated through a column and dried, obtaining 10 g (Y=71%) of a white solid.

Synthesis Example 10

Synthesis of 2-(2,5-dibromophenyl)benzo[d]thiazole

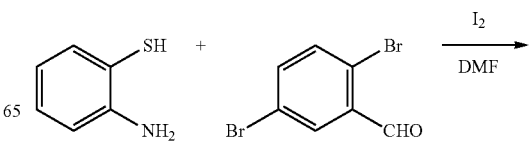

-continued

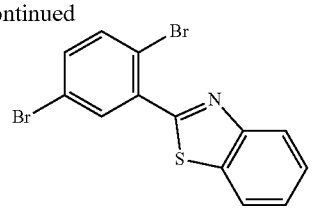

5 g (18.5 mmol) of 2,5-dibromobenzaldehyde, 3 mL (27.7 mmol) of 2-aminothiophenol, and 2.35 g (9.25 mmol) of iodine were dissolved in 100 mL of DMF. The solution was reacted at 100° C. for 1 hour. The obtained reactant was purified through a column, obtaining 4.64 g (Y=68%) of a white solid.

Synthesis Example 11

Synthesis of 2-(2-bromopyridin-3-yl)benzo[d]thiazole

[Reaction Scheme 11]

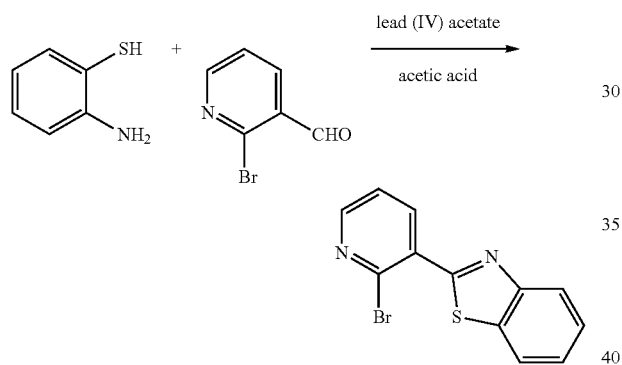

6.58 g (34.0 mmol) of 2-bromo-3-pyrdinecarboxaldehyde and 5.5 mL (50.9 mmol) of 2-aminothiophenol were dissolved in 150 mL of acetic acid. The solution was agitated at room temperature for 30 minutes. Next, 19.0 g (40.8 mmol) of lead (IV) acetate was added thereto. The resulting product was agitated at 50° C. for 1 hour. Then, water was added to the obtained reactant. The mixture was extracted with ethyl acetate and treated under a reduced pressure to remove the solvent, obtaining 5.55 g (Y=55%) of a white solid.

Synthesis Example 12

Synthesis of 2-(3,5-dibromophenyl)benzo[d]oxazole

[Reaction Scheme 12]

-continued

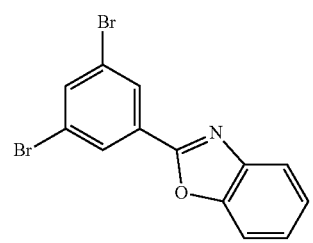

10 g (37.9 mmol) of 3,5-dibromobenzaldehyde and 5 g (45.5 mmol) of 2-aminophenol were dissolved in 200 mL of acetic acid. The solution was agitated at room temperature for 30 minutes. Next, 20.2 g (45.5 mmol) of lead(IV) acetate was added thereto. The resulting product was agitated at 50° C. for 1 hour. Then, water was added to the obtained reactant. The mixture was extracted with ethyl acetate and treated under a reduced pressure to remove the solvent, obtaining 5.7 g (Y=42%) of a white solid.

Example 1

Synthesis of a Compound of Chemical Formula 44

[Reaction Scheme 13]

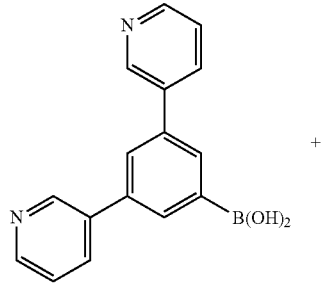

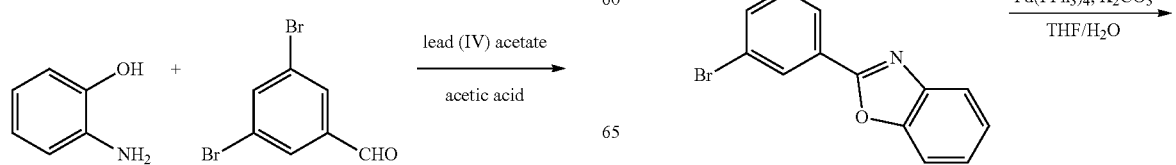

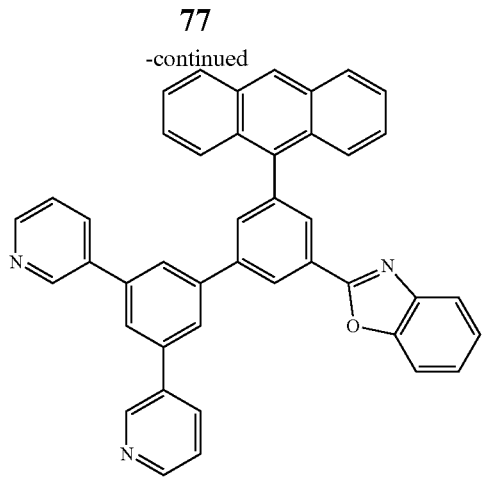

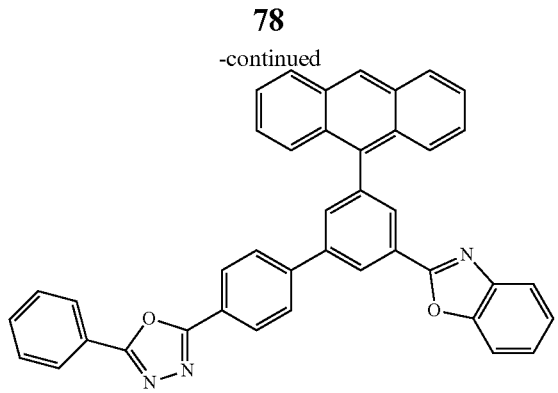

5 g (18.1 mmol) of 3,5-di-(3-pyridinyl)-benzene boronic acid), 8.16 g (18.1 mmol) of 2-(3-(anthracen-9-yl)-5-bromophenyl)benzo[d]oxazole according to Synthesis Example 1, 0.63 g (3 mol %) of tetrakis(triphenylphosphine)palladium (0), and 5 g (36.2 mmol) of potassium carbonate were dissolved in 450 ml of a solvent of tetrahydrofuran/H$_2$O mixed in a volume ratio of 2/1. The solution was reacted at 80° C. for 12 hours. The obtained reactant was extracted with ethyl acetate and treated under a reduced pressure to remove the solvent. The extract was separated through a column and dried, obtaining 6 g (Y=55%) of a white solid.

Example 2

Synthesis of a Compound of Chemical Formula 64

2.32 g (6.7 mmol) of (2-(4-(4,4,5,5-tetramethyl-1,3,2-dioxaborolan-2-yl)phenyl)-5-phenyl-1,3,4-oxadiazole according to Synthesis Example 2, 2.5 g (5.5 mmol) of 2-(3-(anthracen-9-yl)-5-bromophenyl)benzo[d]oxazole according to Synthesis Example 1, 0.19 g (3 mol %) of tetrakis(triphenylphosphine)palladium (0), and 1.2 g (11.1 mmol) of sodium carbonate were dissolved in 90 ml of a solvent of tetrahydrofuran/H$_2$O mixed in a volume ratio of 2/1. The solution was reacted at 80° C. for 12 hours. The obtained reactant was extracted with ethyl acetate and treated under a reduced pressure to remove the solvent. The extract was separated through a column and dried, obtaining 2.6 g (Y=79%) of a white solid.

Example 3

Synthesis of a Compound of Chemical Formula 83

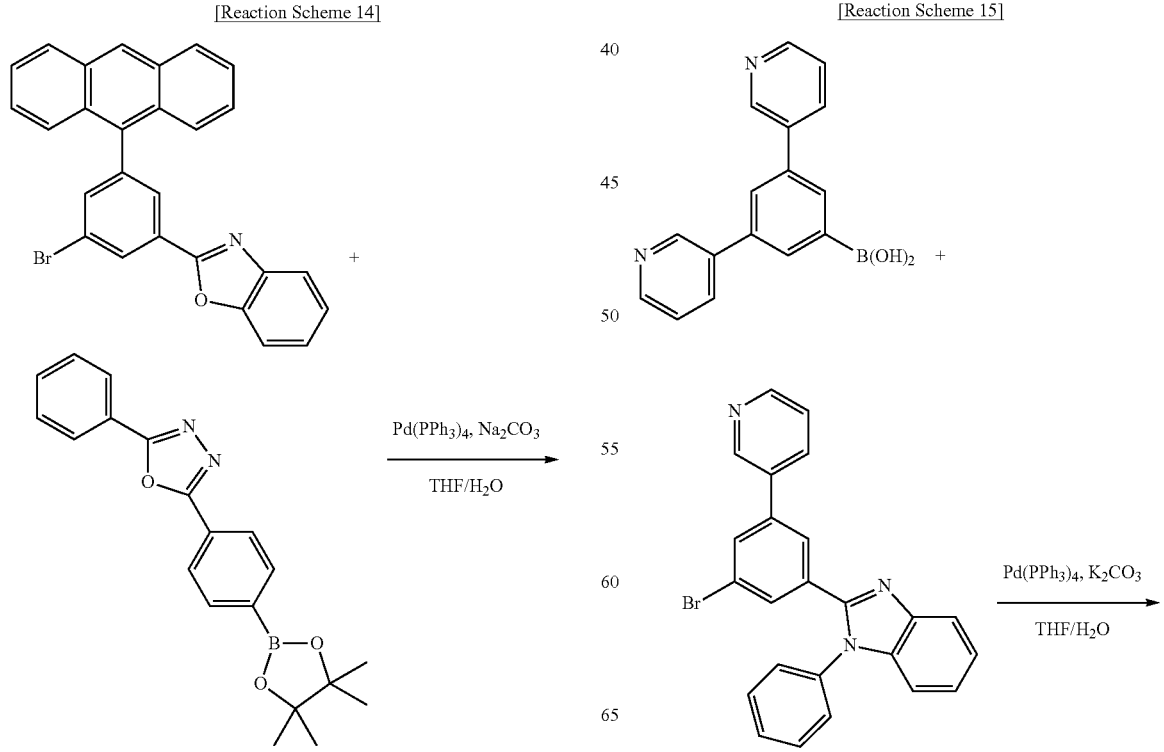

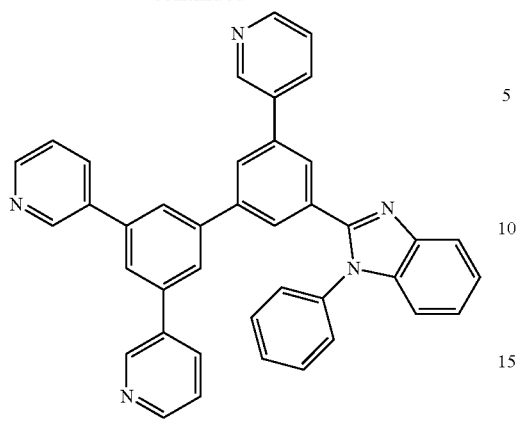

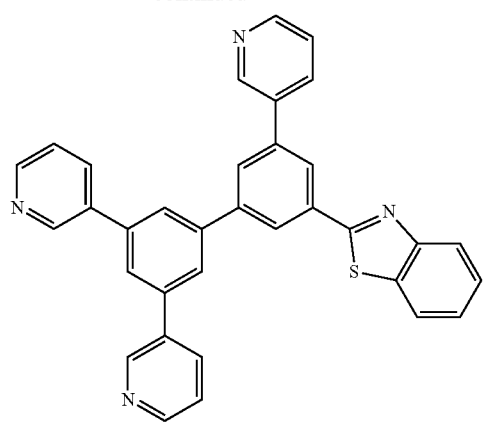

4.14 g (15.0 mmol) of 3,5-di-(3-pyridinyl)-benzene boronic acid, 6.4 g (15.0 mmol) of 2-(3-bromo-5-(pyridin-3-yl)phenyl)-1-phenyl-1H-benzo[d]imidazole according to Synthesis Example 4, 0.52 g (3 mol %) of tetrakis(triphenylphosphine)palladium (0), and 4.15 g (30.0 mmol) of potassium carbonate were dissolved in 300 ml of a solvent of tetrahydrofuran/H$_2$O mixed in a volume ratio of 2/1. The solution was reacted at 80° C. for 12 hours. The obtained reactant was extracted with ethyl acetate and treated under a reduced pressure to remove the solvent. The extract was separated through a column and dried, obtaining 1.2 g (Y=13%) of a white solid.

0.84 g (3.1 mmol) of 3,5-di-(3-pyridinyl)-benzene boronic acid), 1.0 g (2.8 mmol) of 2-(3-bromo-5-(pyridin-3-yl)phenyl)benzo[d]thiazole according to Synthesis Example 6, 0.14 g (5 mol %) of tetrakis(triphenylphosphine)palladium (0), and 1.15 g (8.34 mmol) of potassium carbonate were dissolved in 25 mL of a solvent of tetrahydrofuran/H$_2$O mixed in a volume ratio of 4/1. The solution was reacted at 80° C. for 12 hours. The obtained reactant was extracted with ethyl acetate and treated under a reduced pressure to remove the solvent. The extract was separated through a column and dried, obtaining 1.35 g (Y=92%) of a white solid.

Example 4

Synthesis of a Compound of Chemical Formula 87

Example 5

Synthesis of a Compound of Chemical Formula 92

[Reaction Scheme 16]

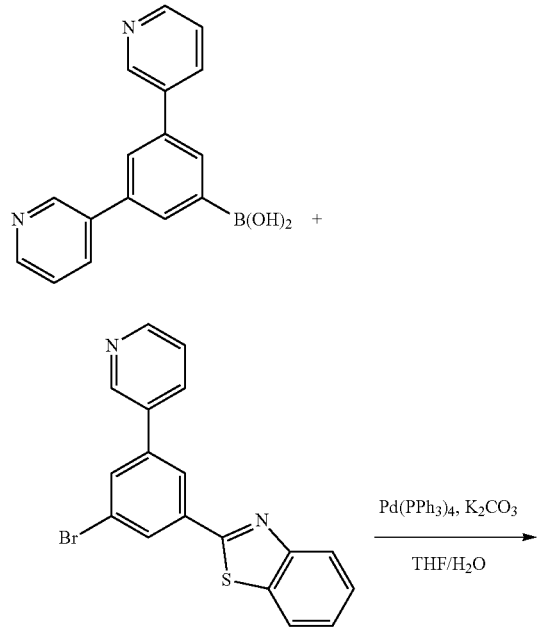

[Reaction Scheme 17]

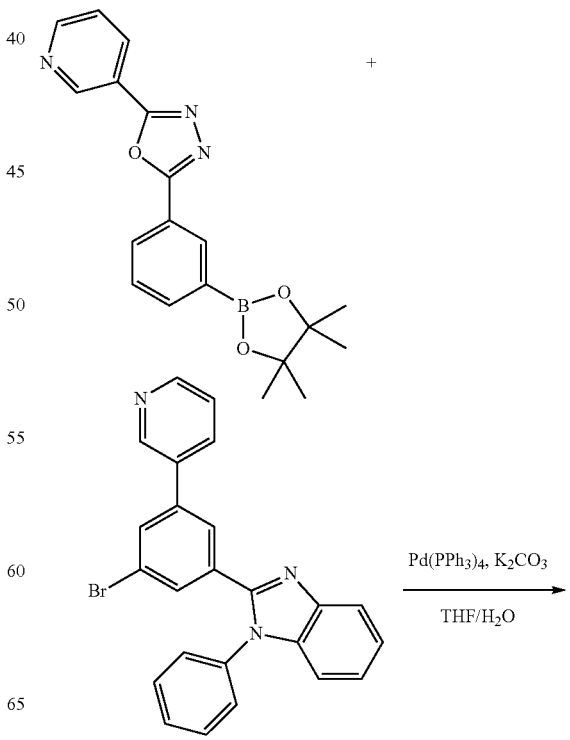

-continued

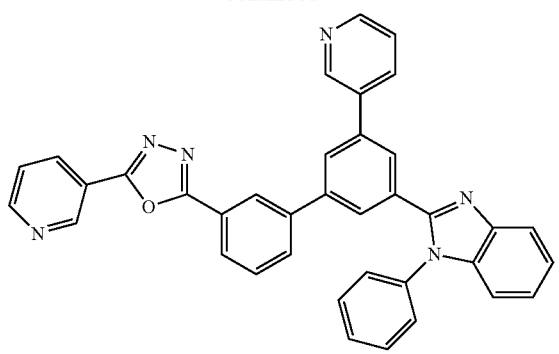

4.63 g (13.3 mmol) of 3-(5-(3-(4,4,5,5-tetramethyl-1,3,2-dioxaborolan-2-yl)phenyl)-1,3,4-oxadiazol-2-yl)pyridine according to Synthesis Example 9, 5.15 g (12.1 mmol) of 2-(3-bromo-5-(pyridin-3-yl)phenyl)-1-phenyl-1H-benzo[d]imidazole) according to Synthesis Example 4, 0.47 g (3 mol %) of tetrakis(triphenylphosphine)palladium (0), and 3.3 g (24.2 mmol) of potassium carbonate were dissolved in 300 mL of a solvent tetrahydrofuran/H$_2$O mixed in a volume ratio of 4/1. The solution was reacted at 80° C. for 12 hours. The obtained reactant was extracted with ethyl acetate and treated under a reduced pressure to remove the solvent. The extract was separated through a column and dried, obtaining 2 g (Y=33%) of a white solid.

Example 6

Synthesis of a Compound of Chemical Formula 96

[Reaction Scheme 18]

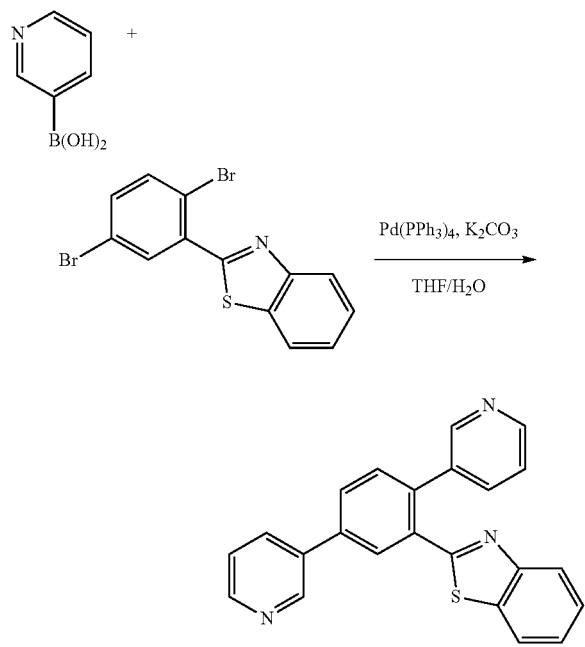

1 g (2.76 mmol) of 2-(2,5-dibromophenyl)benzo[d]thiazole according to Synthesis Example 10, 0.85 g (6.9 mmol) of pyridine-3-boronic acid, 0.28 g (10 mol %) of tetrakis(triphenylphosphine)palladium (0), and 2.3 g (16.6 mmol) of potassium carbonate were dissolved in 25 mL of a solvent of tetrahydrofuran/H$_2$O mixed in a volume ratio of 4/1. The solution was reacted at 80° C. for 12 hours. The obtained reactant was extracted with ethyl acetate and treated under a reduced pressure to remove the solvent. The extract was separated through a column and dried, obtaining 0.8 g (Y=79%) of a white solid.

Example 7

Synthesis of a Compound of Chemical Formula 105

[Reaction Scheme 19]

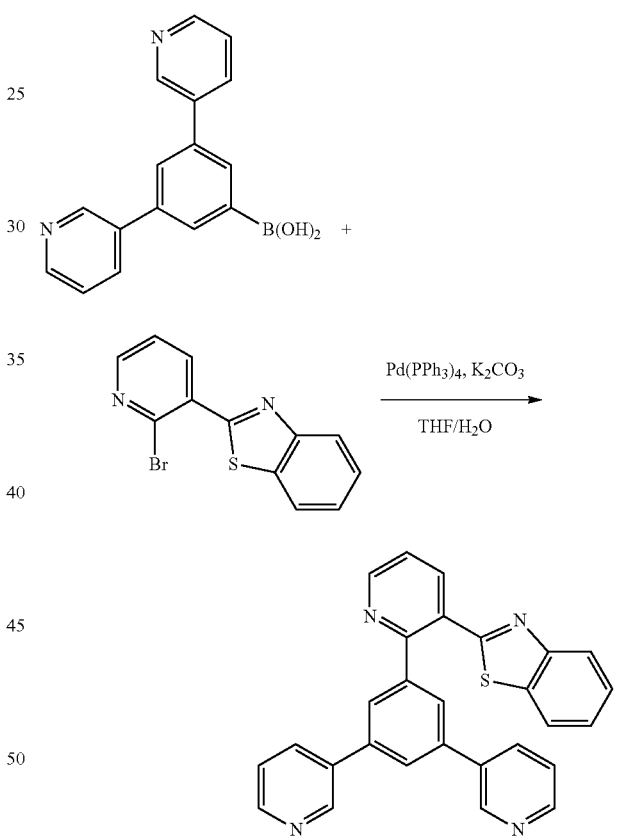

1.33 g (4.8 mmol) of 3,5-di-(3-pyridinyl)-benzene boronic acid, 1.7 g (5.8 mmol) of 2-(2-bromopyridine-3-yl)benzo[d]thiazole according to Synthesis Example 11, 0.28 g (5 mol %) of tetrakis(triphenylphosphine)palladium (0), and 2.0 g (14.4 mmol) of potassium carbonate were dissolved in 30 mL of a solvent of tetrahydrofuran/H$_2$O mixed in a volume ratio of 4/1. The solution was reacted at 80° C. for 12 hours. The obtained reactant was extracted with ethyl acetate and treated under a reduced pressure to remove the solvent. The extract was separated through a column and dried, obtaining 2.28 g (Y=88%) of a white solid.

Example 8

Synthesis of a Compound of Chemical Formula 108

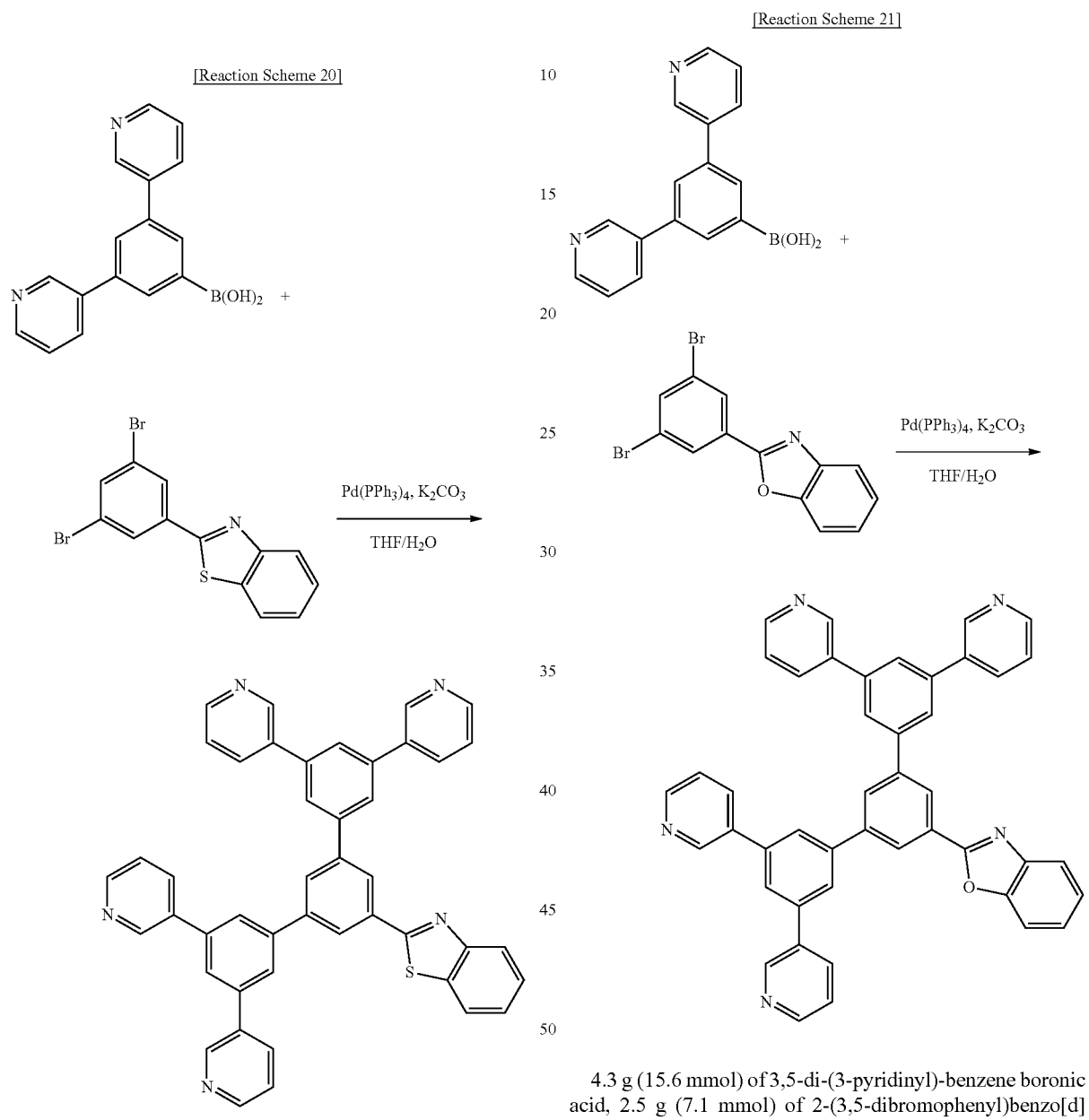

[Reaction Scheme 20]

[Reaction Scheme 21]

2.3 g (8.4 mmol) of 3,5-di-(3-pyridinyl)-benzene boronic acid, 1.5 g (4.0 mmol) of 2-(3,5-dibromophenyl)benzo[d]thiazole according to Synthesis Example 5, 0.46 g (10 mol %) of tetrakis(triphenylphosphine)palladium (0), and 3.3 g (23.9 mmol) of potassium carbonate were dissolved in 50 mL of a solvent of tetrahydrofuran/H$_2$O mixed in a volume ratio of 4/1. The solution was reacted at 80° C. for 12 hours. The obtained reactant was extracted with ethyl acetate and treated under a reduced pressure to remove the solvent. The extract was separated through a column and dried, obtaining 2.04 g (Y=75%) of a white solid.

Example 9

Synthesis of a Compound of Chemical Formula 110

4.3 g (15.6 mmol) of 3,5-di-(3-pyridinyl)-benzene boronic acid, 2.5 g (7.1 mmol) of 2-(3,5-dibromophenyl)benzo[d]oxazole according to Synthesis Example 12, 0.82 g (10 mol %) of tetrakis(triphenylphosphine)palladium (0), and 5.9 g (42.7 mmol) of potassium carbonate were dissolved in 100 mL of a solvent of tetrahydrofuran/H$_2$O mixed in a volume ratio of 4/1. The solution was reacted at 80° C. for 12 hours. The obtained reactant was extracted with ethyl acetate and treated under a reduced pressure to remove the solvent. The extract was separated through a column and dried, obtaining 3.37 g (Y=72%) of a white solid.

The compounds according to Examples 1 to 9 were analyzed through $^1$H NMR (nuclear magnetic resonance spectroscopy). The results are respectively provided in FIGS. 6 to 14.

Comparative Example 1

2-(4-biphenylyl)-5-(4-t-butylphenyl)-1,3,4-oxadiazole (PBD)

2-(4-biphenylyl)-5-(4-t-butylphenyl)-1,3,4-oxadiazole (PBD), which is conventionally known to have an excellent charge transport capability, was prepared.

Example 10

Fabrication of an Organic Light Emitting Diode

A 15 $\Omega/cm^2$ (120 nm) ITO glass substrate (Corning Inc.) was prepared to have a size of 25 mm×25 mm×0.7 mm, and was respectively washed in isopropyl alcohol and pure water for 5 minutes, and was then cleaned again with UV and ozone.

Next, a 40 nm-thick N,N'-di(4-(N,N'-diphenyl-amino)-phenyl)-N,N'-diphenylbenzidine (DNTPD) hole injection layer (HIL) was formed on the substrate.

Then, N,N'-bis(naphthalen-1-yl)-N,N'-bis(phenyl)benzidine (NPB) was vacuum-deposited to form a 10 nm-thick hole transport layer (HTL) on the hole injection layer (HIL).

EB-46 and EB-512 (e-Ray Optoelectronics Technology Co., Ltd.) as a light emitting material were vacuum-deposited in a weight ratio of 94:6 to form a 40 nm-thick emission layer on the hole transport layer (HTL).

The compound according to Example 2 as an electron transport material was vacuum-deposited to form a 10 nm-thick electron transport layer (ETL) on the emission layer.

On the electron transport layer (ETL), LiF 0.5 nm/Al 100 nm were respectively and sequentially vacuum-deposited to form a cathode including LiF/Al, fabricating an organic light emitting diode of Example 10.

Example 11

Fabrication of an Organic Light Emitting Diode

An organic light emitting diode was fabricated according to the same method as in Example 10, except for using a compound according to Example 3 to form an electron transport layer (ETL).

Example 12

Fabrication of an Organic Light Emitting Diode

An organic light emitting diode was fabricated according to the same method as in Example 10, except for using a compound according to Example 4 to form an electron transport layer (ETL).

Example 13

Fabrication of an Organic Light Emitting Diode

An organic light emitting diode was fabricated according to the same method as in Example 10, except for using a compound according to Example 5 to form an electron transport layer (ETL).

Example 14

Fabrication of an Organic Light Emitting Diode

An organic light emitting diode was fabricated according to the same method as in Example 10, except for using a compound according to Example 7 to form an electron transport layer (ETL).

Example 15

Fabrication of an Organic Light Emitting Diode

An organic light emitting diode was fabricated according to the same method as in Example 10, except for using a compound according to Example 8 to form an electron transport layer (ETL).

Example 16

Fabrication of an Organic Light Emitting Diode

An organic light emitting diode was fabricated according to the same method as in Example 10, except for using a compound according to Example 9 to form an electron transport layer (ETL).

Comparative Example 2

Fabrication of an Organic Light Emitting Diode

An organic light emitting diode was fabricated according to the same method as in Example 10, except for using an electron transport material of $Alq_3$ to form an electron transport layer (ETL).

Property Measurement and Analysis

1) Driving Voltage, Luminance and Luminous Efficiency

The organic light emitting diodes of Examples 10 to 16 and Comparative Example 2 were measured regarding a driving voltage ($V_d$) required to produce luminance of 1000 nit, and current efficiency (cd/A) and electrical power efficiency (lm/W) at the same luminance. The results are shown in the following Table 1.

TABLE 1

| Devices | At 1000 cd/m² | | | | Max. | |
| --- | --- | --- | --- | --- | --- | --- |
| | $V_d$ (V) | cd/A | lm/W | $V_{on}$ | cd/A | lm/W |
| Comparative Example 2 | 7.40 | 4.68 | 1.99 | 3.60 | 4.72 | 2.88 |
| Example 10 | 6.20 | 5.19 | 2.63 | 3.20 | 5.35 | 3.25 |
| Example 11 | 7.20 | 5.29 | 2.31 | 3.80 | 5.32 | 2.77 |
| Example 12 | 6.40 | 5.00 | 2.45 | 3.00 | 5.32 | 3.34 |
| Example 13 | 7.40 | 4.99 | 2.12 | 3.20 | 5.32 | 3.37 |
| Example 14 | 6.40 | 5.80 | 2.85 | 3.00 | 5.88 | 3.51 |
| Example 15 | 7.20 | 5.56 | 2.43 | 3.40 | 5.66 | 3.54 |
| Example 16 | 6.00 | 6.04 | 3.16 | 3.20 | 6.32 | 4.14 |

Figure 15:
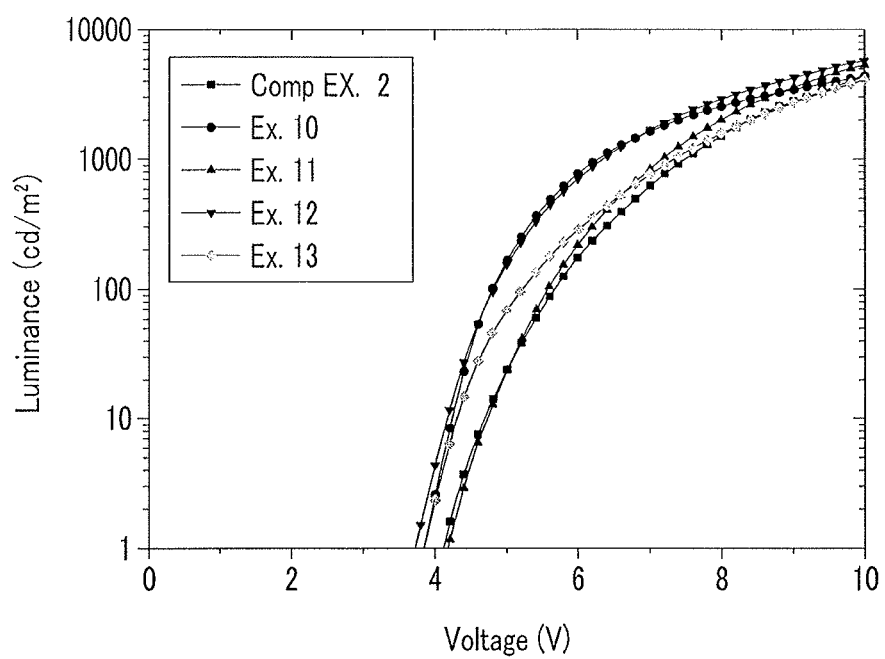
FIG. 15 illustrates a graph showing voltage-luminescence characteristics of organic light emitting diodes according to Examples 10 to 13 and Comparative Example 2.
Figure 16:
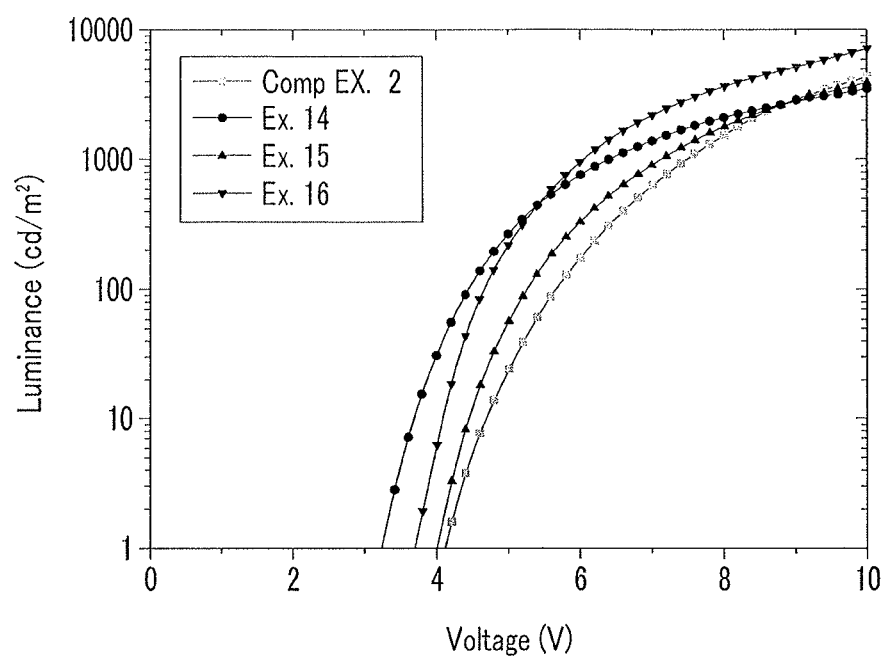
FIG. 16 illustrates a graph showing voltage-luminescence characteristics of organic light emitting diodes according to Examples 14 to 16 and Comparative Example 2.
Figure 17:
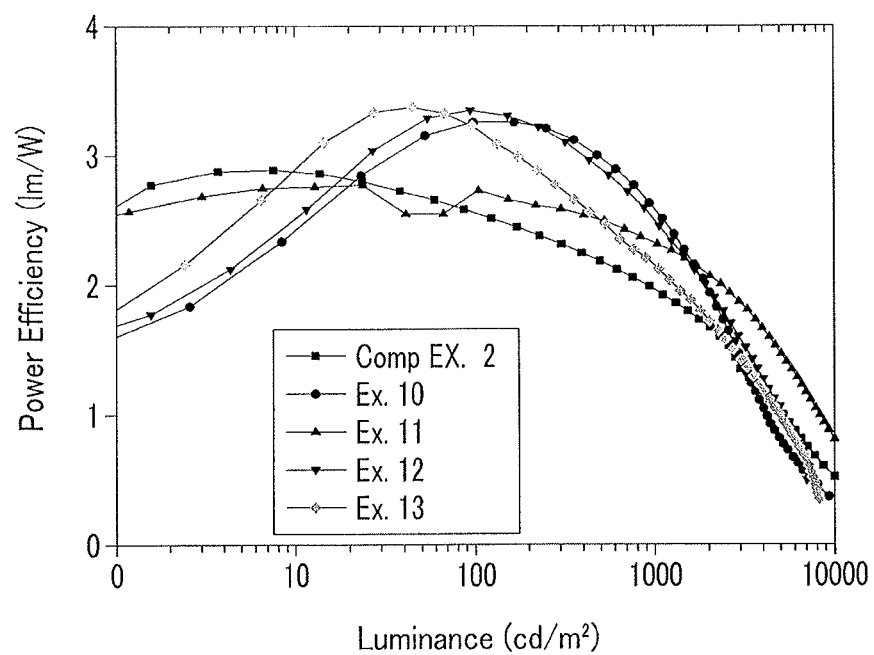
FIG. 17 illustrates a graph showing electrical power efficiency of the organic light emitting diodes according to Examples 10 to 13 and Comparative Example 2.
Figure 18:
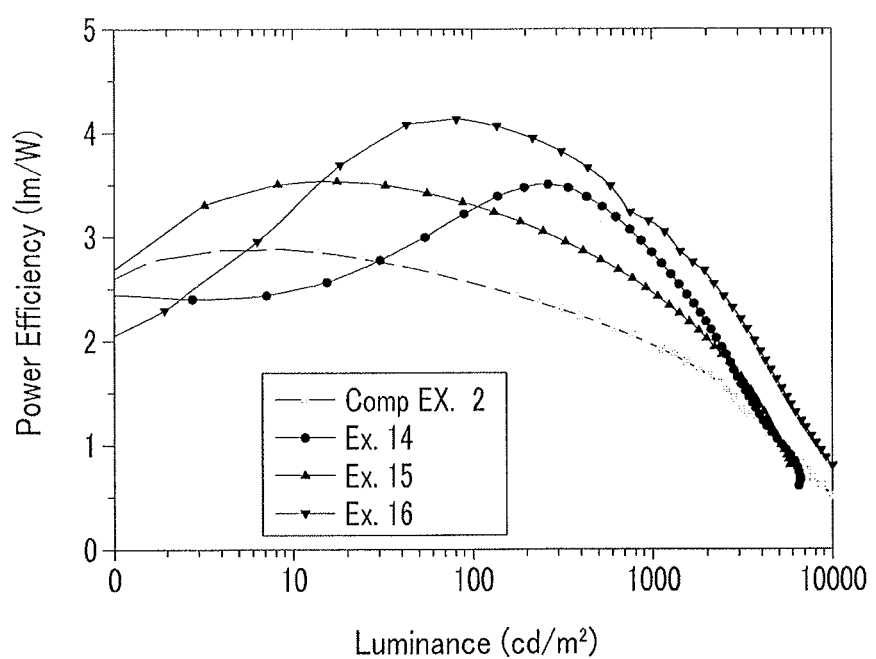
FIG. 18 illustrates a graph showing electrical power efficiency of the organic light emitting diodes according to Examples 14 to 16 and Comparative Example 2.

Referring to Table 1 and FIGS. 15 and 16, the organic light emitting diodes of Examples 10 to 16 generally had a sharply lower driving voltage than those of Comparative Example 2. In addition, referring to Table 1 and FIGS. 17 and 18, the organic light emitting diodes of Examples 10 to 16 generally had a sharply lower driving voltage but superbly high current efficiency and electrical power efficiency.

These measurement results of the organic light emitting diodes come from combination balance of holes and electrons in the emission layer. The compounds of Examples 10 to 16 exhibited excellent electron injection and transport characteristics compared with $Alq_3$, a general electron transport material.

2) Thermal Stability

Figure 19:
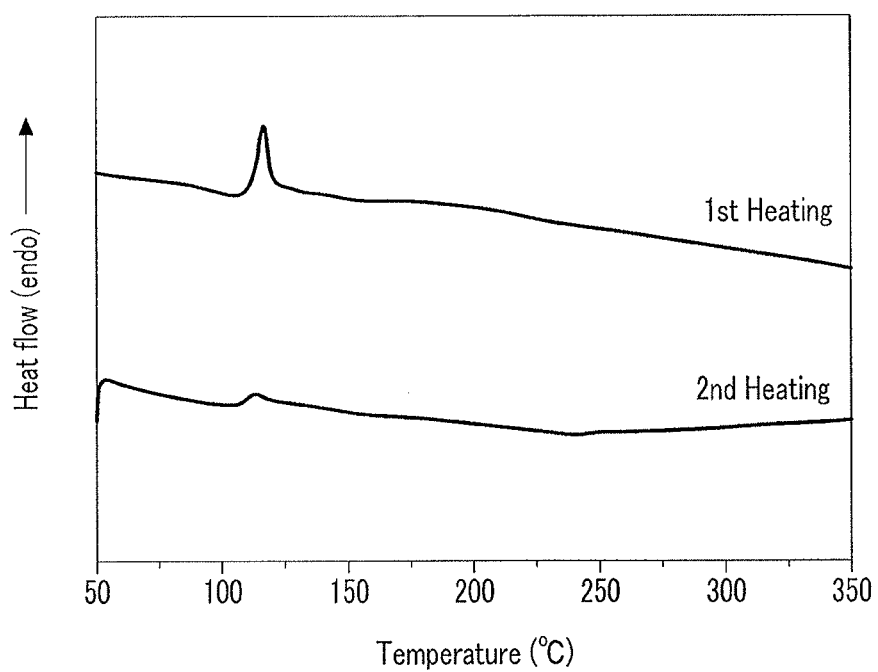
FIG. 19 illustrates a graph showing thermal properties of the compound according to Example 5.
Figure 20:
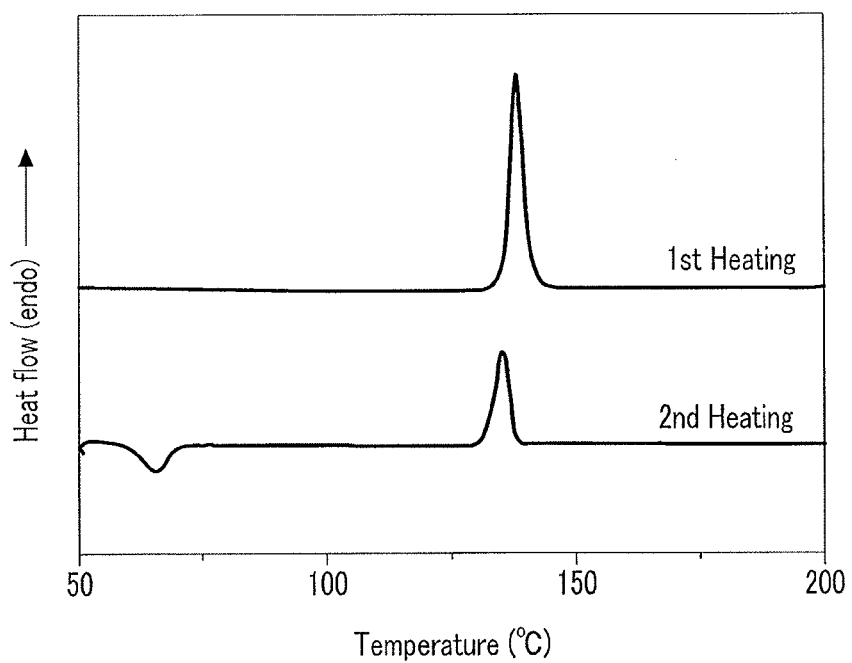
FIG. 20 illustrates a graph showing thermal properties of the compound according to Comparative Example 1.

The compounds according to Examples 1 to 9 were analyzed in a differential scanning calorimetry method (DSC), and then secondarily analyzed in the same method. The analysis results of the compounds according to Example 5 and Comparative Example 1 are shown in FIGS. 19 and 20. Referring to FIGS. 19 and 20, the compound of Example 5 had melting point peaks in the primary analysis, but no melting point peak in the secondary analysis. On the contrary, 2-(4-biphenylyl)-5-(4-t-butylphenyl)-1,3,4-oxadiazole (PBD) according to Comparative Example 1 had a melting point peak at 138° C. in both primary and secondary analyses and a crystallizing temperature at 65° C. in the secondary analysis. The compounds of Example 5 were identified to stably exist in an amorphous state, compared with the conventional material. Therefore, the organic light emitting diodes including the compound of the embodiments exhibited reduced influence of Joule heat generated during the operation, and thereby may have an improved life-span characteristic compared with a conventional organic light emitting diode.

By way of summation and review, both low molecular weight organic light emitting and polymer organic light emitting diodes have advantages of being self-light emitting and ultrathin, and having a high speed response, a wide viewing angle, high image quality, durability, a large driving temperature range, and the like. For example, they have good visibility due to the self-light emitting characteristic (compared with a conventional LCD (liquid crystal display)) and have an advantage of decreasing thickness and weight of LCD by up to a third (because they do not need a backlight). In addition, since they have a response speed that is 1,000 times faster per microsecond unit than an LCD, they can realize a perfect motion picture without an after-image. Based on these advantages, they have been developed to have 80 times the efficiency and more than 100 times the life-span since they were first introduced. Recently, these diodes have been used in larger displays, e.g., for a 40-inch organic light emitting diode panel.

These large displays should simultaneously have improved luminous efficiency and life-span. In order to increase the luminous efficiency, smooth combination between holes and electrons in an emission layer is desirable. However, an organic material may generally have slower electron mobility than hole mobility and may exhibit inefficient combination between holes and electrons.

In addition, devices may have a decreased life-span if the material therein is crystallized due to Joule heat generated when it is driven. 2-(4-biphenylyl)-5-(4-t-butylphenyl)-1,3,4-oxadiazole (PBD) with a rapid transfer speed may have a good lifespan, but may also lack thermal stability and may be crystallized when a device is driven. In addition, BCP and an aluminum mixed coordination complex (BAlq, bis(2-methyl-8-quinolinolate)-4-(phenylphenolate)aluminum) (which is excellent in lowering hole mobility) have excellent characteristic in lowering hole mobility but may deteriorate the electron injection characteristic and may be crystallized when a device is driven.

Accordingly, the embodiments provide a compound that increases electron injection and mobility from a cathode and simultaneously helps prevent movement of holes. The embodiments also provide a compound having high thermal stability and that suppresses crystallization when a device is driven.

The embodiments provide a compound that can act as a hole injection, hole transport, light emitting, or electron injection and/or transport material, and also as a light emitting host along with an appropriate dopant.

The embodiments also provide an organic photoelectric device including the compound for an organic photoelectric device, and having decreased driving voltage and increased life-span and efficiency.

The embodiments provide a compound for an organic photoelectric device that is largely asymmetric. The asymmetric structure may reinforce an amorphous characteristic and may thereby suppress crystallization, thus improving thermal stability of the compound for an organic photoelectric device. Accordingly, when an organic photoelectric device is driven, the compound may decrease the driving voltage and improve life-span and efficiency.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic photoelectric device, the compound being represented by the following Chemical Formula 112:

[Chemcial Formula 112]

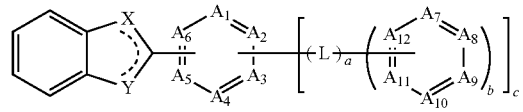

wherein, in Chemical Formula 112,
$A_1$ to $A_{12}$ are each independently selected from the group of $CR_1$ to $CR_{12}$ and N, provided that one or two of $A_7$ to $A_{12}$ are N, and $R_1$ to $R_6$ adjacent to each other optionally form a fused ring, and $R_7$ to $R_{12}$ adjacent to each other optionally form a fused ring,
X is selected from the group of O, S, Se, and $NR_{13}$, and Y is $CR_{14}$ or N, provided that when X is selected from the group of O, S, and Se, Y is N,
L is a substituted or unsubstituted C6 to C50 arylene,
a is 0 or 1, provided that when a is 0, $A_1$ to $A_6$ are each independently $CR_1$ to $CR_6$, and when a is 1, at least one of $A_1$ to $A_6$ is N,
b and c are each independently an integer of 1 to 3,
$R_1$ to $R_{14}$ are each independently selected from the group of hydrogen, a halogen, a nitrile, a cyano, a nitro, an amide, a carbonyl, an ester, a substituted or unsubstituted alkyl, a substituted or unsubstituted alkylene, a substituted or unsubstituted alkoxy, a substituted or unsubstituted alkenyl, a substituted or unsubstituted alkenylene, a substituted or unsubstituted alkynyl, a substituted or unsubstituted alkynylene, a substituted or unsubstituted cycloalkyl, a substituted or unsubstituted cycloalkylene, a substituted or unsubstituted aryl, a substituted or unsubstituted arylene, a substituted or unsubstituted arylamine, a substituted or unsubstituted heteroarylamine, a substituted or unsubstituted heterocycle, a substituted or unsubstituted amino, BRR', or SiRR'R", wherein R, R' and R" are the same or different, and each independently a substituted or unsubstituted alkyl, or a substituted or unsubstituted aryl, and at least one of $R_1$ to $R_{14}$ is a substituted or unsubstituted heterocycle, the substituted or unsubstituted heterocycle including one of a thiophenyl, a furanyl, a pyrrolyl, a thiazolyl, an oxazolyl, an oxadiazolyl, a triazolyl, a pyridinyl, a pyridazinyl, a quinolinyl, an isoquinolinine, an acridyl, an imidazopyridinyl, and an imidazopyrimidinyl.

2. The compound as claimed in claim 1, wherein in Chemical Formula 112:
one of $R_7$ to $R_{12}$ is substituted with a substituent selected from the group of an amine-substituted alkyl, an amine-substituted cycloalkyl, an amine substituted aryl, and an amine-substituted heterocycle, and
one of $R_1$ to $R_6$ is substituted with a substituent selected from the group of a nitrile, a nitro, an amide, a carbonyl, and a substituted or unsubstituted heterocycle.

3. The compound as claimed in claim 1, wherein the compound is represented by the following Chemical Formula 113:

[Chemical Formula 113]

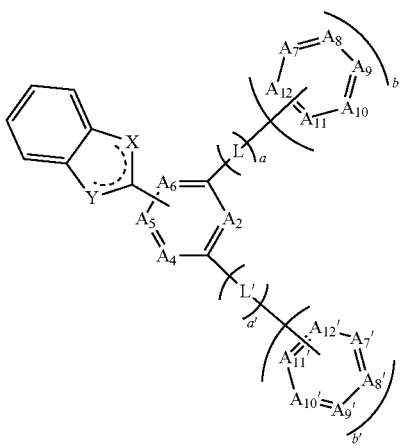

wherein, in Chemical Formula 113, $A_2$, $A_4$ to $A_{12}$ and $A_7'$ to $A_{12}'$ are each independently selected from the group of $CR_2$, $CR_4$ to $CR_{12}$, $CR_7'$ to $CR_{12}'$ and N, provided at least one of $A_7$ to $A_{12}$ is N, and at least one of $A_7'$ to $A_{12}'$ is N, wherein $R_4$ to $R_6$ adjacent to each other optionally form a fused ring, $R_7$ to $R_{12}$ adjacent to each other optionally form a fused ring, and $R_7'$ to $R_{12}'$ adjacent to each other optionally form a fused ring, X is selected from the group of O, S, Se, and $NR_{13}$, and Y is $CR_{14}$ or N, provided that when X is selected from the group of O, S, and Se, Y is N, L and L' are each independently a substituted or unsubstituted C6 to C50 arylene, a and a' are each independently 0 or 1, provided that when a and a' are each independently 0, $A_2$, $A_4$ to $A_6$ are each independently $CR_2$ and $CR_4$ to $CR_6$, and when a and a' are each independently 1, at least one of A, and $A_4$ to $A_6$ is N, b and b' are each independently an integer of 1 to 3, and $R_2$, $R_4$ to $R_{14}$, and $R_7'$ to $R_{12}'$ are each independently hydrogen, a halogen, a nitrile, a cyano, a nitro, an amide, a carbonyl, an ester, a substituted or unsubstituted alkyl, a substituted or unsubstituted alkylene, a substituted or unsubstituted alkoxy, a substituted or unsubstituted alkenyl, a substituted or unsubstituted alkenylene, a substituted or unsubstituted alkynyl, a substituted or unsubstituted alkynylene, a substituted or unsubstituted cycloalkyl, a substituted or unsubstituted cycloalkylene, a substituted or unsubstituted aryl, a substituted or unsubstituted arylene, a substituted or unsubstituted arylamine, a substituted or unsubstituted heteroarylamine, a substituted or unsubstituted heterocycle, a substituted or unsubstituted amino, BRR', or SiRR'R", wherein R, R' and R" are the same or different, and each independently a substituted or unsubstituted alkyl, or a substituted or unsubstituted aryl.

4. The compound as claimed in claim 1, wherein, in Chemical Formula 112, at least one of $R_1$ to $R_{14}$ is a substituted or unsubstituted arylamine, the substituted or unsubstituted arylamine including one of a diphenyl amine, a dinaphthyl amine, a dibiphenyl amine, a phenyl naphthyl amine, a phenyl diphenyl amine, a ditolyl amine, a phenyl tolyl amine, a carbazolyl, and a triphenyl amine.

* * * * *